(12) United States Patent
Turner et al.

(10) Patent No.: US 7,951,361 B2
(45) Date of Patent: *May 31, 2011

(54) BACTERIAL VACCINE

(75) Inventors: Arthur Keith Turner, Cambridge (GB); Judith Greenwood, Cambridge (GB); Jonathan Clive Stephens, Cambridge (GB); Juliet Claire Beavis, Cambridge (GB); Michael James Darsley, Cambridge (GB)

(73) Assignee: Acambis Research Limited, Cambridge (GB)

( * ) Notice: Subject to any disclaimer, the term of this patent is extended or adjusted under 35 U.S.C. 154(b) by 1579 days.

This patent is subject to a terminal disclaimer.

(21) Appl. No.: 10/489,242

(22) PCT Filed: Sep. 11, 2002

(86) PCT No.: PCT/GB02/04123
§ 371 (c)(1), (2), (4) Date: Aug. 5, 2004

(87) PCT Pub. No.: WO03/022306
PCT Pub. Date: Mar. 20, 2003

(65) Prior Publication Data
US 2004/0253710 A1    Dec. 16, 2004

(30) Foreign Application Priority Data
Sep. 11, 2001 (GB) .................. 0121998.9

(51) Int. Cl.
*A61K 39/02* (2006.01)
*A61K 39/108* (2006.01)
*A61K 48/00* (2006.01)
*A01N 63/00* (2006.01)
*A01N 65/00* (2006.01)

(52) U.S. Cl. .............. 424/93.1; 424/93.2; 424/93.4; 424/241.1; 424/257.1

(58) Field of Classification Search .......... None
See application file for complete search history.

(56) References Cited

U.S. PATENT DOCUMENTS

| | | | |
|---|---|---|---|
| 4,935,364 A | 6/1990 | Kaper et al. | |
| 6,019,982 A | 2/2000 | Clements et al. | |
| 6,902,906 B1 * | 6/2005 | Chatfield | 435/41 |
| 7,118,758 B1 * | 10/2006 | Wolf et al. | 424/257.1 |
| 7,332,172 B2 * | 2/2008 | Wolf et al. | 424/241.1 |
| 7,399,474 B2 * | 7/2008 | Altboum et al. | 424/190.1 |
| 7,404,961 B2 * | 7/2008 | Cassels et al. | 424/257.1 |
| 2005/0054075 A1 | 3/2005 | Turner et al. | |
| 2009/0136567 A1 * | 5/2009 | Savarino et al. | 424/463 |

FOREIGN PATENT DOCUMENTS

| | | |
|---|---|---|
| WO | WO 92/14487 | 9/1992 |
| WO | WO 92/15689 | 9/1992 |
| WO | WO 99/49026 | 9/1999 |
| WO | 99/61634 | 12/1999 |
| WO | 00/37106 | 6/2000 |
| WO | WO 00/37106 | 6/2000 |
| WO | WO 03/022307 | 3/2003 |

OTHER PUBLICATIONS

McKenzie et al, Infection and Immunity, 2006, 74/2:994-1000.*
Aitken et al. "Recombinant enterotoxins as vaccines against *Escherichia coli*-mediated diarrhoea" Vaccine 11:227-233 (1993).
Altboum et al. "Attenuated *Shigella flexneri2a* ΔguaBA strain CVD 1204 expressing enterotoxigenic *Escherichia coli* (ETEC) CS2 and CS3 fimbriae as a live mucosal vaccine against *Shigella* and ETEC infection" Infect. Immun. 69:3150-3158 (2001).
Altboum et al. "Genetic characterization and immunogenicity of coli surface antigen 4 from enterotoxigenic *Escherichia coli* when it is expressed in a *Shigella* live-vector strain" Infect. Immun. 71:1352-1360 (2003).
Burkardt et al. "Relationship of group P1 plasmids revealed by heteroduplex experiments: RP1, RP4, R68 and RK2 are identical" J. Gen. Microbiol. 114:341-348 (1979).
Chang et al. "Construction and characterization of amplifiable multicopy DNA cloning vehicles derived from the P15A cryptic miniplasmid" J. Bacteriol. 134:1141-1156 (1978).
Chong et al. "LT(R192G), a non-toxic mutant of the heat-labile enterotoxin of *Escherichia coli*, elicits enhanced humoral and cellular immune responses associated with protection against lethal oral challenge with *Salmonella* spp." Vaccine 16:732-740 (1998).
Cieplak et al. "Site-directed mutagenic alteration of potential active-site residues of the A subunit of *Escherichia coli* heat-labile enterotoxin" J. Biol. Chem. 270:30545-30550 (1995).
Clements "Construction of a nontoxic fusion peptide for immunization against *Escherichia coli* strains that produce heat-labile and heat-stable enterotoxins" Infect. Immun. 58:1159-1166 (1990).
Cravioto "Role of transmissible plasmids in enterotoxin production" Ph.D. Thesis pp. 37-39, 91-97, 114-115, 120-124, 234-236, 240 and 262 University of London, London United Kingdom (1980).
de Haan et al. "The nucleotide sequence of a regulatory gene present on a plasmid in an enterotoxigenic *Escherichia coli* strain of serotype O167:H5" FEMS Microbiol. Lett. 83:341-346 (1991).
Donnenberg et al. "Construction of an *eae* deletion mutant of enteropathogenic *Escherichia coli* by using a positive-selection suicide vector" Infect. Immun. 59:4310-4317 (1991).
Dunstan et al. "Use of in vivo-regulated promoters to deliver antigens from attenuated *Salmonella enterica* var. Typhimurium" Infect. Immun. 67:5133-5141 (1999).

(Continued)

*Primary Examiner* — N. M Minnifield
(74) *Attorney, Agent, or Firm* — Nixon & Vanderhye, P.C.

(57) ABSTRACT

A bacterial cell which expresses three or more coli surface (CS) antigens and methods of making such a cell. The cell is useful in making vaccines against diarrhea.

15 Claims, 27 Drawing Sheets

OTHER PUBLICATIONS

Duthy et al. "CS5 pilus biosynthesis genes form enterotoxigenic *Escherichia coli* O115:H40" J. Bacteriol. 181:5847-5851 (1999).

Duthy et al. "Characterization of the CsfC and CsfD proteins involved in the biogenesis of CS5 pili from enterotoxigenic *Escherichia coli*" Microbial. Pathogen. 31:115-129 (2001).

Everest et al. "Expression of LacZ from the *htrA, nirB* and *groE* promoters in a *Salmonella* vaccine strain: Influence of growth in a mammalian cells" FEMS Microbiology Lett. 126:97-102 (1995).

Gerdes et al. "Unique type of plasmid maintenance function: Postsegregational killing of plasmid-free cells" Proc. Natl. Acad. Sci. USA 83:3116-3120 (1986).

Gerdes et al. "The *hok* killer gene family in gram-negative bacteria" The New Biologist 2:946-956 (1990).

Jalajakumari et al. "Genes for biosynthesis and assembly of CS3 pili of CFA/II enterotoxigenic *Escherichia coli*: Novel regulation of pilus production by bypassing an amber codon" Mol. Microbiol. 3:1685-1695 (1989).

Kolter et al. "Trans-complementation-dependent replication of a low molecular weight origin fragment from plasmid R6K" Cell 15:1199-1208 (1978).

Marron et al. "Molecular analysis of the CSO operon of enterotoxigenic *Escherichia coli* reveals that CsoA is the adhesin of CS1 fimbriae and that the accessory genes are interchangeable with those of the cfa operon" Microbiol. 141:2849-2859 (1995).

Miller et al. "Synthesis of cholera toxin is positively regulated at the transcriptional level by *toxR*" Proc. Natl. Acad. Sci. USA 81:3471-3475 (1984).

Milton et al. "Flagellin A is essential for the virulence of *Vibrio anguillarum*" J. Bacteriol. 178:1310-1319 (1996).

Roberts et al. "The *parDE* operon of the broad-host-range plasmid RK2 specifies growth inhibition associated with plasmid loss" J. Mol. Biol. 237:35-51 (1994).

Savelkoul et al. "Expression of CFA/I fimbriae is positively regulated" Microbial Pathogen. 8:91-99 (1990).

Scotland et al. "Properties of wild-type strains of enterotoxigenic *Escherichia coli* which produce colonization factor antigen II, and belong to serogroups other than O6" J. Gen. Microbiol. 131:2327-2333 (1985).

Scott et al. "CooB is required for assembly but not transport of CS1 pilin" Mol. Microbiol. 6:293-300 (1992).

Simon et al. "A broad host range mobilization system for in vivo genetic engineering: Transposon mutagenesis in gram negative bacteria" Biotech. 1:784-791 (1983).

Summers et al. "Multimer resolution systems of ColE1 and ColK: Localisation of the crossover site" Mol. Gen. Genet. 201:334-338 (1985).

Turner et al. "Construction and characterization of generitcally defined *aro omp* mutants of enterotoxigenic *Escherichia coli* and preliminary studies of safety and immunogenicity in humans" Infect. Immun. 69:4969-4979 (2001).

Valdivia et al. "Fluorescence-based isolation of bacterial genes expressed within host cells" Science 277:2007-2011 (1997).

Willshaw et al. "Cloning of genes encoding coli-surface (CS) antigens in enterotoxigenic *Escherichia coli*" FEMS Microbiol. Lett. 49:473-478 (1988).

Willshaw et al. "Plasmid-encoded production of coli-surface associated antigen 1 (CS1) in a strain of *Escherichia coli* serotype O139.H28" Microbial Pathogen. 9:1-11 (1990).

Wolf et al. "The CS6 colonization factor of human enterotoxigenic *Escherichia coli* contains two heterologous major subunits" FEMS Microbiol. Lett. 148:35-42 (1997).

Wolf "Occurrence, distribution, and associations of O and H serogroups, colonization fator antigens, and toxins of enterotoxigenic *Escherichia coli*" Clin. Microbiol. Rev. 10:569-584 (1997).

Daley et al. "Genetically modified enterotoxigenic *Escherichia coli* vaccines induce mucosal immune responses without inflammation" Gut 56:1550-1556 (Nov. 2007), published online gut.bmj.com on Jun. 12, 2007.

Froehlich et al, "Genes for CS2 Pili of Enterotoxigenic *Escherichia coli* and Their Interchangeability with Those for CS1 Pili". Infection and Immunity, vol. 63, No. 12, 1995, pp. 4849-4856.

Hibberd et al, "Positive regulation of colonization factor antigen I (CFA/I) production by enterotoxigenic *Escherichia coli* producing the colonization factors CS5, CS6, CS7, CS17, PCF09, PCF0159: H4 and PCF0166", Journal of General Microbiology, vol. 137, No. 8, 1991, pp. 1963-1970.

Peruski et al, "Characterization of enterotoxigenic *Escherichia coli* factors", Abstracts of the General Meeting of the American Society for, vol. 98, 1998, p. 224.

Qadri et al, "Safety and immunogenicity of an oral, inactivated enterotoxigenic *Escherichia coli* plus cholera toxin B subunit vaccine in Bangladeshi adults and children", Vaccine, Butterworth Scientific, Guildford, GB, vol. 18, No. 24, Jun. 2000, pp. 2704-2712.

Echeverria et al. "Plasmids coding for colonization factor antigens I and II, heat-labile enterotoxin, and heat-stable enterotoxin A2 in *Escherichia coli*" Infect. Immun. 51:626-630 (1986).

Gaastra & Svennerholm "Colonization factors of human enterotoxigenic *Escherichia coli* (ETEC)" Trends Microbiol. 4:444-452 (1996).

Girón et al. "Prevalence and association of the longus pilus structural gene (*IngA*) with colonization factor antigens, enterotoxin types, and serotypes of enterotoxigenic *Escherichia coli*" Infect. Immun. 63:4195-4198 (1995).

Gutiérrez-Cázarez et al. "Identification of enterotoxigenic *Escherichia coli* harboring longus type IV pilus gene by DNA amplification" J. Clin. Microbiol. 38:1767-1771 (2000).

Kaper et al. "A recombinant live oral cholera vaccine" Bio/Technol. 2:345-349 (1984).

Levine et al. "Colonization factor antigens I and II and type 1 somatic pili in enterotoxigenic *Escherichia coli*: Relation to enterotoxin" Infect. Immun. 39:889-897 (1983).

McConnell et al. "Plasmids coding for colonization factor antigen I and heat-stable enterotoxin production isolated from enterotoxigenic *Escherichia coli*: Comparison of their properties" Infect. Immun. 32:927-936 (1981).

Murray et al. "CFA/I-ST plasmids: Comparison of enterotoxigenic *Escherichia coli* (ETEC) of serogroups O25, O63, O78, and O128 and mobilization from an R factor-containing epidemic ETEC isolate" J. Bacterial. 153:566-570 (1983).

Oyofo et al. "Toxins and colonization factor antigens of enterotoxigenic *Escherichia coli* among residents of Jakarta, Indonesia" Am. J. Trop. Med. Hyg. 65:120-124 (2001).

Reis et al. "Transfer of a CFA/I-ST plasmid promoted by a conjugative plasmid in a strain of *Escherichia coli* of serotype Oi28ac:H12" Infect. Immun. 29:140-143 (1980).

Sommerfelt et al. "Mechanism of spontaneous loss of heat-stable toxin (STa) production in enterotoxigenic *Escherichia coli*" APMIS 97:436-440 (1989).

Thomas et al. "In strains of *Escherichia coli* O167 a single plasmid encodes for the coli surface antigens CS5 and CS6 of putative colonization factor PCF8775, heat-stable enterotoxin, and colicin Ia". Infect. Immun. 55:1929-1931 (1987).

Qadri et al. "Prevalence of toxin types and colonization factors in enterotoxigenic *Escherichia coli* isolated during a 2-year period from diarrheal patients in Bangladesh" J. Clin. Microbiol. 38:27-31 (2000).

Wolf "Occurrence, distribution, and associations of O and H serogroups, colonization factor antigens, and toxins of enterotoxigenic *Escherichia coli*" 10:569-584 (1997).

* cited by examiner

B.

A.

C.

D.

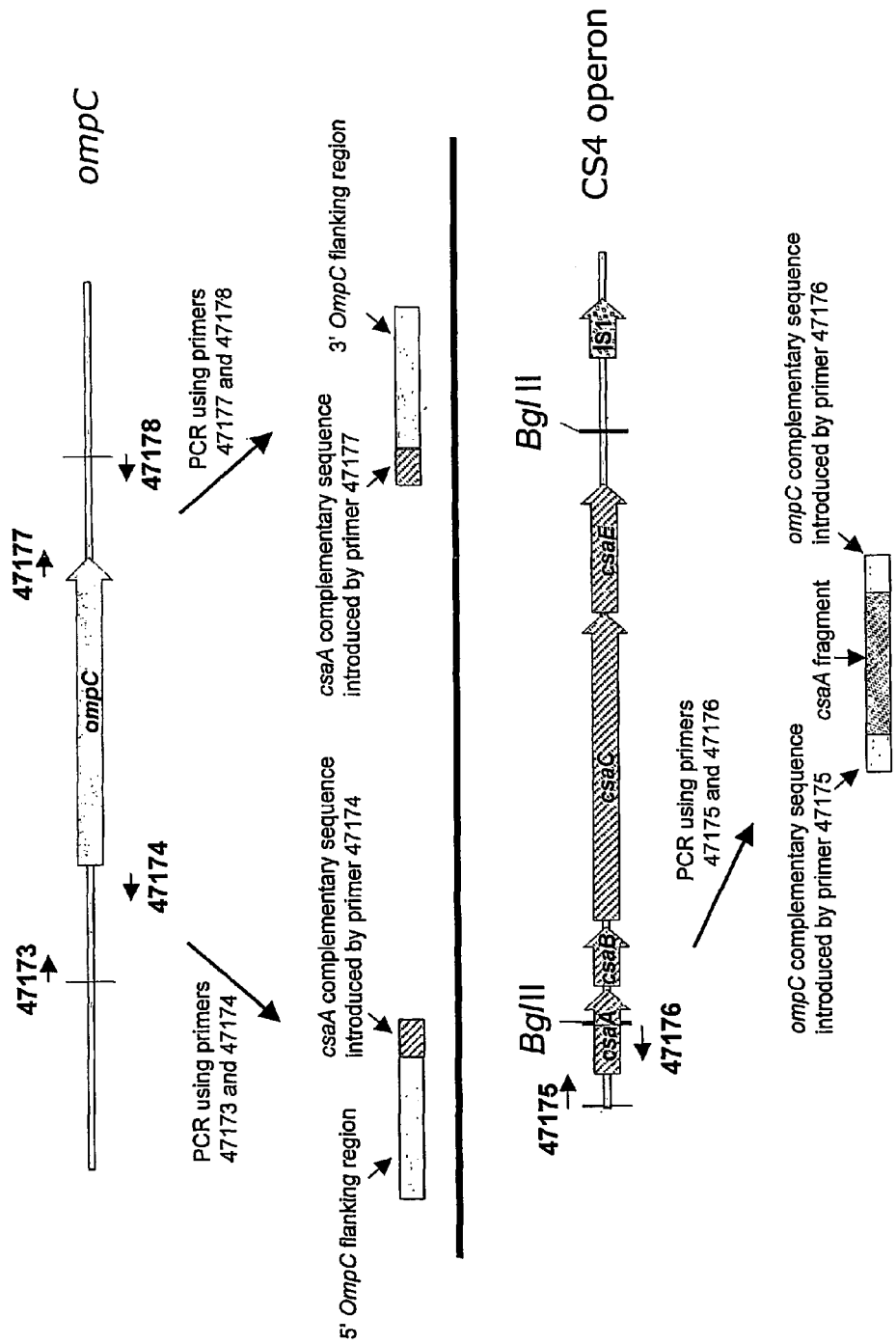
Figure 3A  Stage 1

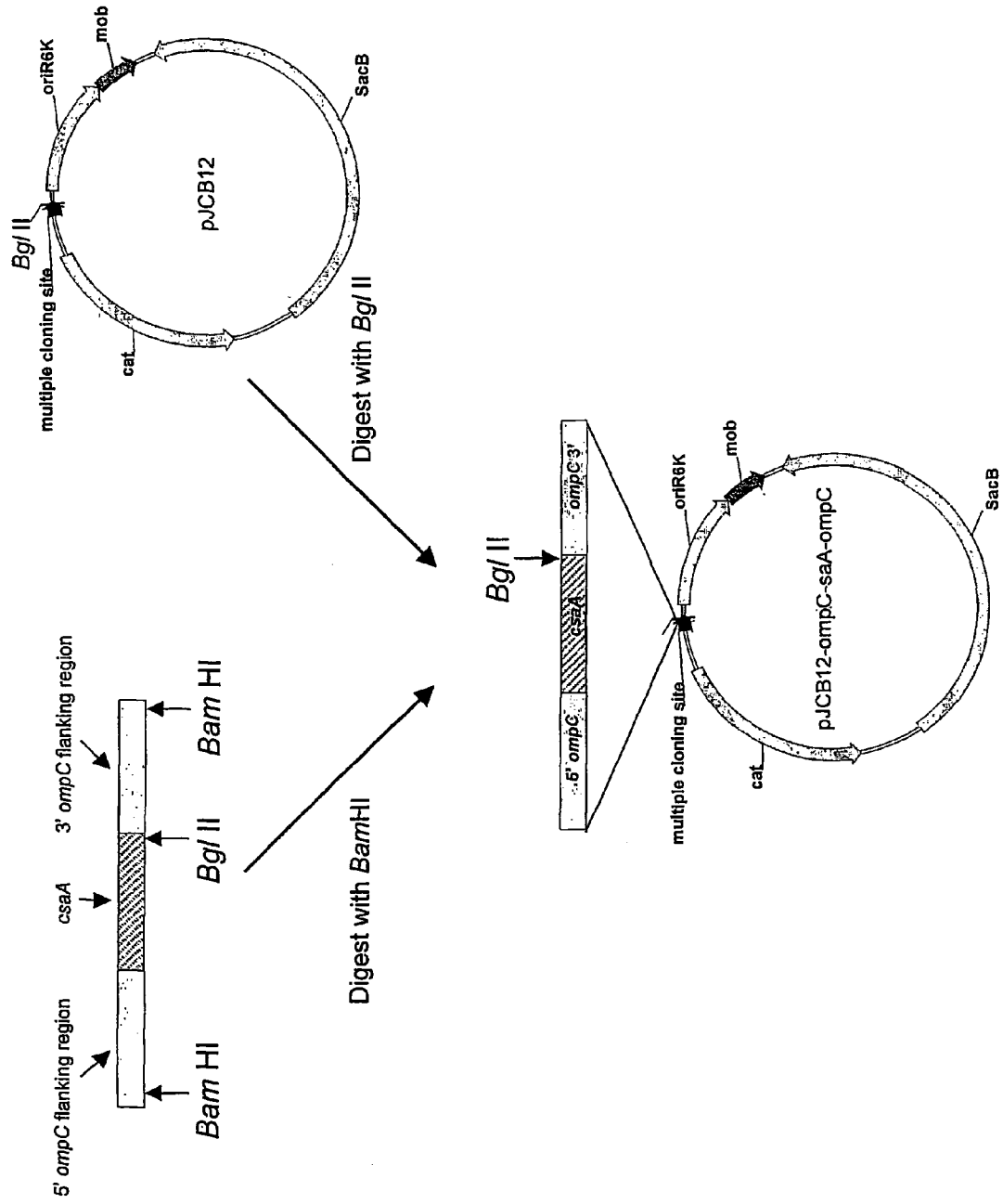
Figure 3A    Stage 4

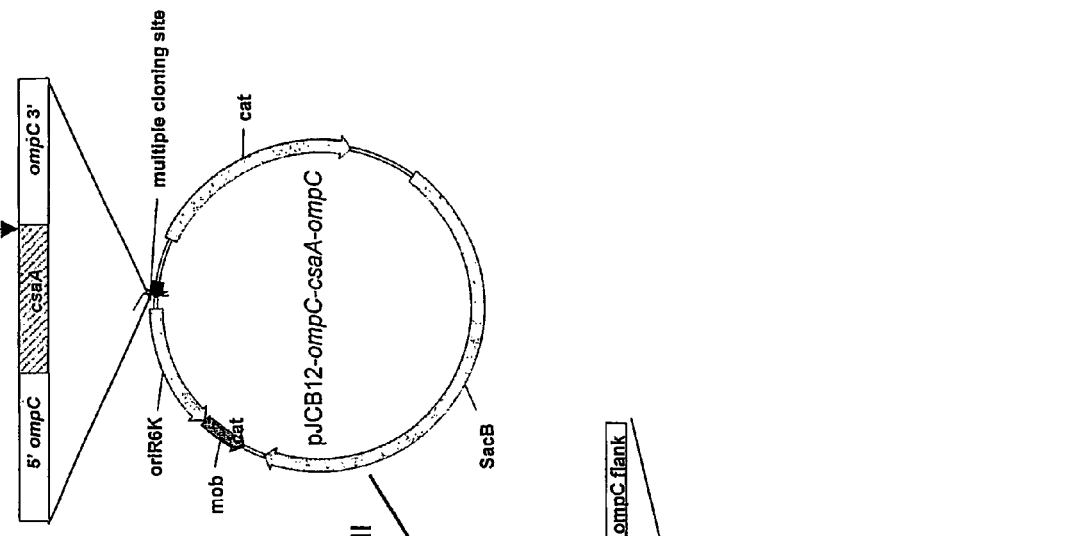
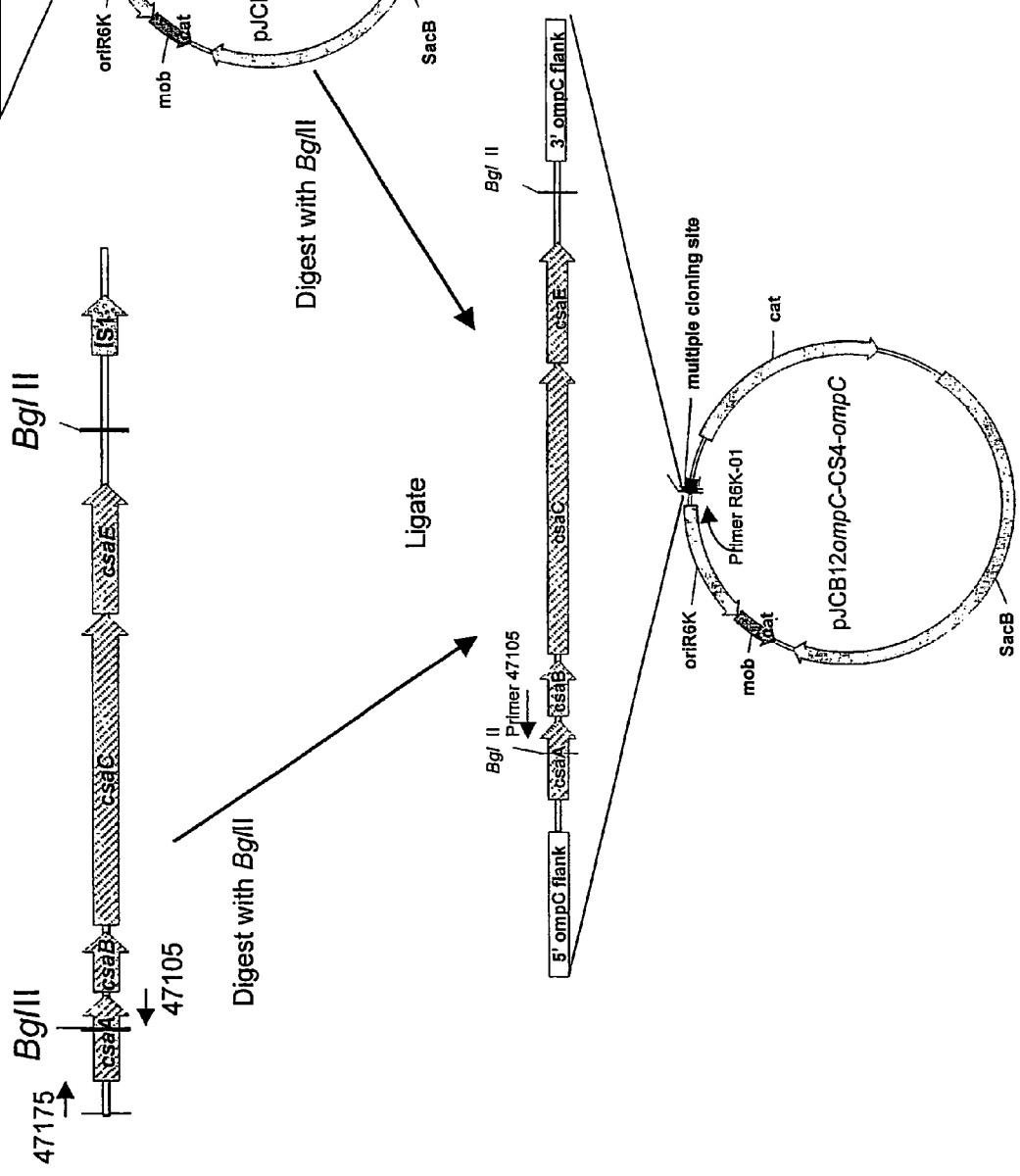
Figure 3A Stage 5

Figure 3B 47173  5'- GAC|GGATCC|GAATGCGAGGCATCCGGTTG-3'  } Amplification of 5' ompC flanking region + addition of csaA overlap sequence 47174  3'-CGTTTATTTCCGTATATTGTCTGAATAACTCCTT-5'
47175         5'- TATAACAGAGCTTATTGAGGAATATCGGTGTC-3'  } Amplification of csaA +addition of 5' and 3' ompC overlap sequences 47176  3'-ATACGCCGAGATTAG|TCTAGA|GCTGTGTTGGT-5'
47177         5'-TCTAATCAGATCT|CGACAACCAGTTCACTCGTG-3'  } Amplification of 3' ompC flanking region + addition of csaA overlap sequence 47178  3'-GGGCGGACTACGCGAAATTG|CCTAGG|TGG-5'

ACAM2006 - bile salts

ACAM2006 + bile salts

ACAM2009 - bile salts

ACAM2009 + bile salts

ACAM2009-pCS5 - bile salts

ACAM2009-pCS5 + bile salts

CS5
CS4
CS6

Figure 10
Fig 10B
Fig 10A

Step 1

Step 2

BACTERIAL VACCINE

This application is the US national phase of international application PCT/GB02/04123 filed 11 Sep. 2002 which designated the U.S. and claims benefit of GB 0121998.9, dated 11 Sep. 2001, the entire content of which is hereby incorporated by reference.

FIELD OF THE INVENTION

The invention relates to bacterial cells, useful for vaccines, in particular vaccines against diarrhoea.

BACKGROUND OF THE INVENTION

In general, the purpose of a vaccine is to induce an immune response in the recipient, thus providing protection against subsequent challenge with a pathogen. This may be achieved by inoculation with a live attenuated strain of the pathogen, ie. a strain having reduced virulence such that it does not cause the disease caused by the virulent pathogen while still stimulating a broad immune response.

Enterotoxigenic *E. coli* (ETEC) strains are a major cause of travellers diarrhoea and of morbidity and death of children in endemic areas. Virulence is associated with expression of fimbrial colonisation factor antigens (CFAs) which mediate adhesion to the intestine and with secretion of toxins (heat stable toxin (ST), heat labile toxin (LT) and EAST toxin) which are responsible for the loss of fluid characteristic of the disease. Protection against ETEC disease is associated with antibody-mediated neutralisation of the toxins and with a humoral immune response against the CFAs.

SUMMARY OF THE INVENTION

There are several types of CPA associated with virulent strains of ETEC but CFA/I, CFA/II and CFA/IV are the major types, associated with approximately 70% of clinical isolates. CFA/I is a single fimbrial antigen, whereas CFA/II and CFA/IV are each complexes composed of two different types of *coli* surface (CS) antigen. CFA/II is composed of CS3 with either CS1 or CS2. CFA/IV is composed of CS6 with either CS4 or CS5.

CFA expression in wild-type ETEC appears to be restricted so that native ETEC strains express only one type of CFA and a maximum of two types of CS antigen. Thus, native CFA/II ETEC cells are generally either CS1/CS3 or CS2/CS3 expressing strains. Similarly, native CFA/IV ETEC cells are generally either CS4/CS6 or CS5/CS6 expressing strains. CS1 and CS2 have not been found in the same wild type strain (34) and likewise CS4 and CS5 are never expressed together in naturally occurring strains (WO92/01703, (34)).

An effective vaccine against ETEC must immunise against CFA/I, CFA/II and CFA/IV strains as a minimum. Thus, ETEC vaccines have traditionally required a minimum of 5 bacterial strains—one strain expressing CFA/I, one strain expressing CS1/CS3, one strain expressing CS2/CS3, one strain expressing CS4/CS6 and one strain expressing CS5/CS6. However, the present inventors have now devised a method for producing a bacterial cell which is not so restricted in its CS antigen expression. Accordingly, the present invention provides a bacterial cell which expresses three or more *coli* surface (CS) antigens. The invention also provides a method for making such a cell, comprising introducing a polynucleotide encoding a heterologous CS antigen into a bacterial cell.

A bacterial cell according to the invention can be used to manufacture a vaccine against ETEC disease. Thus, the invention provides a vaccine against diarrhoea comprising a cell of the invention and a pharmaceutically acceptable carrier or diluent. Since the present cell avoids the previous limitations on cellular CS antigen expression, the invention provides for the first time, a vaccine against diarrhoea comprising bacterial cells which together express all of CFA/I, CS1, CS2, CS3, CS4, CS5 and CS6, wherein the vaccine comprises fewer than 5 bacterial strains. The invention additionally provides a method of vaccinating a mammal against diarrhoea comprising administering to the mammal a cell or vaccine of the invention.

BRIEF DESCRIPTION OF THE FIGURES

FIG. 3B Features of primers used in construction of pJCB12-ompC-CS4-ompC (SEQ ID NOS: 17 to 22). Forward primers are written 5'-3' in bold. Reverse primers are written 3' to 5' in normal font. Restriction sites are boxed. Additional nucleotides to introduce complementary sequence for overlap extension PCR are underlined.

FIG. 10 SDS PAGE analysis of CFA/I and CS antigen expression in strains WS2252A, ACAM2010 and ACAM2010-pCS4:
(A) Staining with Simply Blue Safe Stain (Invitrogen)
(B) Western Blot.

BRIEF DESCRIPTION OF THE SEQUENCES

Figure 1A:
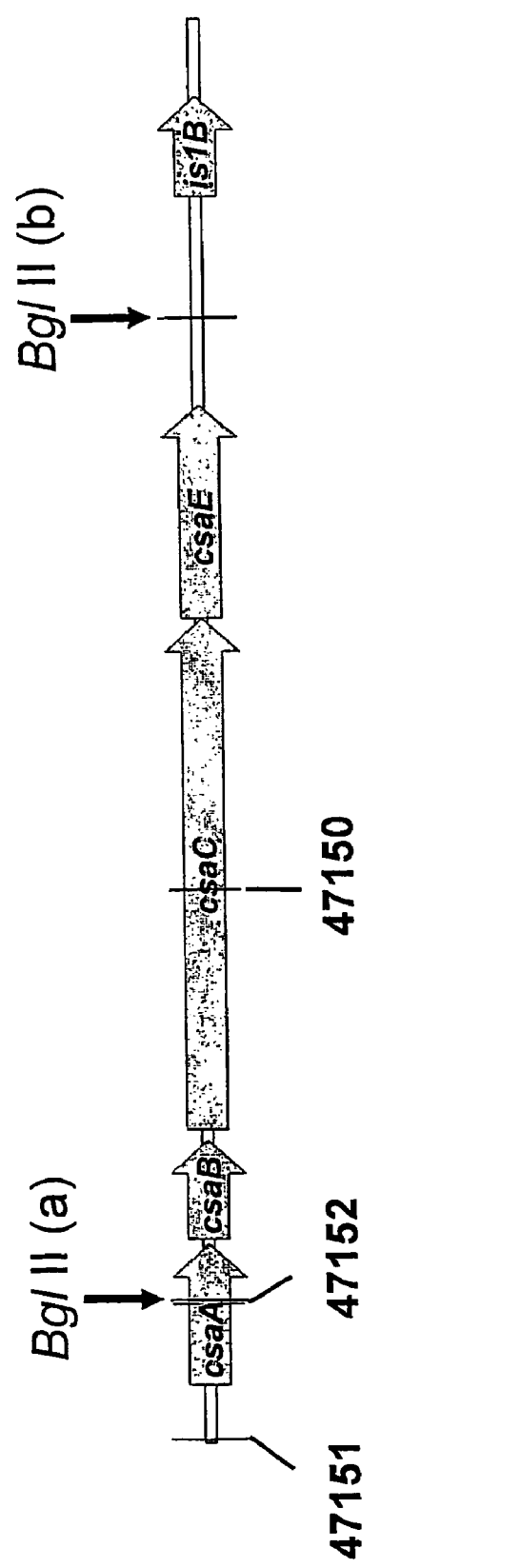
FIG. 1A Structure of the CS4 operon.
Figure 1:
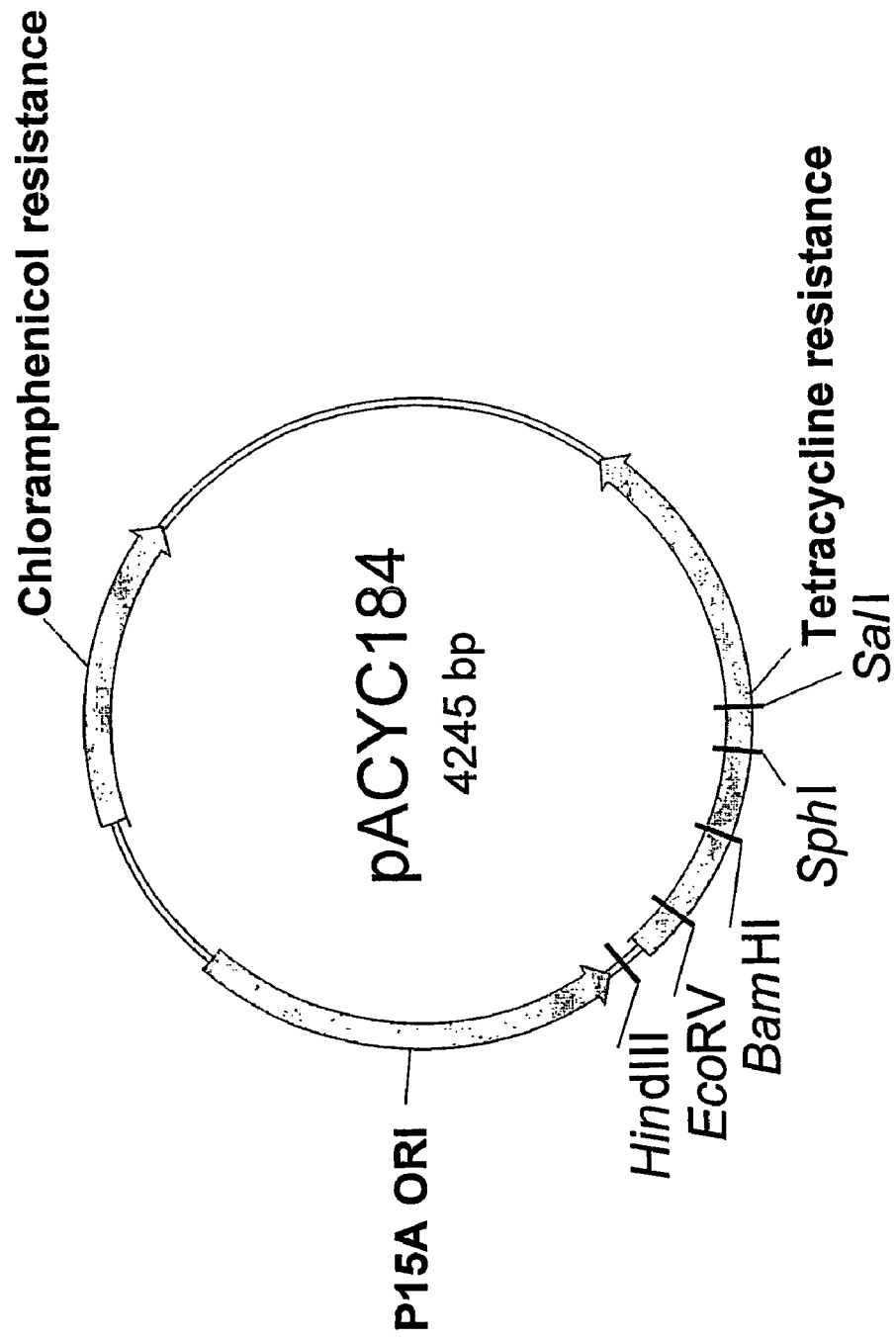
FIG. 1B Map of plasmid pACYC184.
FIG. 1C Map of plasmid pACYC-csaA.
FIG. 1D Map of plasmid pACYC-CS4.

SEQ ID NO:1 is nucleotide sequence encoding cooA of the CS1 operon as under GenBank accession number M58550.

SEQ ID NO:2 is nucleotide sequence encoding cooB of the CS1 operon as under Genbank accession number X62495.

SEQ ID NO:3 is nucleotide sequence encoding cooC and cooD of the CS1 operon as under GenBank accession number X76908.

SEQ ID NO:4 is nucleotide sequence encoding cfaD as under GenBank accession number M55609.

SEQ ID NO:5 is nucleotide sequence encoding cotB, cotA, cotC and cotD of the CS2 operon as under GenBank accession number Z47800.

SEQ ID NO:6 is nucleotide sequence encoding ms as under GenBank accession number J04166.

SEQ ID NO:7 is nucleotide sequence of the CS3 operon as under GenBank accession number X16944.

SEQ ID NO:8 is nucleotide sequence encoding csaA, csaB, csaC, csaE and IS1 of the CS4 operon as under GenBank accession number AF296132.

SEQ ID NO:9 is nucleotide sequence encoding csfA, csfB, csfC, csfE, csfF and csfD of the CS5 operon as under GenBank accession number AJ224079.

SEQ ID NO:10 is nucleotide sequence encoding csvR as under GenBank accession number X60106.

SEQ ID NO:11 is nucleotide sequence encoding cssA, cssB, cssC and cssD of the CS6 operon as under GenBank accession number U04844.

DETAILED DESCRIPTION OF THE INVENTION

A cell of the invention may be derived from any bacterial cell which is capable of expressing an ETEC CS antigen on its surface. In general, the cell is derived from a bacterium that infects a mammalian host by the oral route. The cell may derive from or be descended from a bacterium that invades and grows within eukaryotic cells and/or colonises mucosal surfaces. In general, the cell is gram negative but in some embodiments gram positive bacteria may be used. The bacterium is generally a pathogen.

The bacterial cell used may be from the genus *Escherichia, Salmonella, Shigella* or *Vibrio*. Preferably the cell of the invention is an *E. coli* cell. The present cell may be produced from an ETEC or a non-ETEC *E. coli* strain which does not itself express any ETEC CS antigens.

Preferably the present cell is derived or descended from an ETEC strain which endogenously expresses an ETEC CS antigen, such as CS1, CS2, CS3, CS4, CS5 or CS6. The present cell may for example, be produced from a wild-type ETEC isolate. Alternatively, the present cell may be produced from an ETEC strain which is itself derived from a wild-type or native ETEC strain. For example, the present cell may be descended from a strain in which a particular toxin gene or genes has been mutated or deleted, or which comprises a further attenuating mutation, or which expresses a further heterologous antigen as described below. A wild-type ETEC strain can be isolated from a human clinical sample using standard techniques. An example of a standard ETEC strain is H10407, deposited at the ATCC under catalogue #35401.

A cell of the invention may, for example, be produced from one of ETEC strains ACM2005, ACM2002, ACM2003, ACM2004, ACAM2007, ACAM2008, ACAM 2009 or ACAM2012 listed in Tables 1 and 2. Each of the strains has been deposited by Acambis Research Limited of Peterhouse Technology Park, 100 Fulbourn Road, Cambridge, CB1 9PT, United Kingdom with the European Collection of Cell Cultures (ECACC), CAMR, Salisbury, Wiltshire SP4 0JG, United Kingdom in accordance with the Budapest Treaty. Accession numbers for the deposited strains are given in the Tables. Deposits 01090302 to 01090306 were deposited on 3 Sep. 2001. Deposits 02082964 to 02082968 were deposited on 29 Aug. 2002. Further information about strain characteristics is given in Table 1.

PTL003 (ACM2005, deposit No. 01090302) (Ref 4, 31) was derived from ETEC strain E1392/75-2A (a) (CS1/CS3, ST minus, LT minus) by targeted deletion of three further attenuating genes (aroC, ompC and ompF) (Table 1). PTL003 has already been tested in two clinical trials and has been shown to be safe and immunogenic.

Strains with deposit nos. 01090303-01090306 were described in UK Patent Application 0121998.9. Both these and the strains with deposit nos. 02082964 to 02082968 are described in the International patent application, claiming priority from UK patent application 0121998.9, and filed by Acambis Research Limited on the same day as the present International application. The contents of that application are hereby incorporated by reference. Each of the strains has been made toxin negative by specific removal of the known toxin genes.

A cell according to the invention may express any combination of ETEC CS antigens provided that the cell expresses three or more ETEC CS antigens. A large number of CS antigens have been identified, the most prevalent being CS1, CS2, CS3 (the components of CFA/II) and CS4, CS5 and CS6 (the components of CFA/IV). Additional antigens include CS17, CS7, CS9, CS14, CS12, PCFO159, PCFO166. However CFA/I (GenBank accession no M55661) is not a CS antigen for the purposes of this document.

Preferably a cell of the invention expresses at least one CS antigen selected from ETEC CS1, CS2, CS3, CS4, CS5, CS6. Thus in one embodiment, the present cell may express three or more CS antigens wherein the CS antigen is selected from CS 1, CS2, CS3, CS4, CS5 and CS6. Such a cell may express three, four, five or six of the listed CS antigens. A cell may express the CS antigens in any combination. It is particularly preferred that a cell of the invention expresses one of the following combinations of antigens:

CS1, CS2 and CS3
CS4, CS5 and CS6
CS4, CS1 and CS3
CS1, CS5 and CS6

Thus a cell of the invention may comprise a mixture of CFA protein, for example, a mixture of CFA/II and CFA/IV proteins.

Bacterial cells according to the invention include ACAM 2006-pCS4 (CS4, CS5, CS6), ACAM 2006-CS4 (CS4, CS5, CS6), ACAM2012-pCS4 (CS4, CS5, CS6), ACAM2012-CS4 (CS4, CS5, CS6), ACAM 2007-pCS1 (CS1, CS2, CS3), ACAM 2009-pCS5 (CS4, CS5, CS6), PTL003-pCS4 (CS 1, CS3, CS4) and ACAM2006-pCS1 (CS1, CS5, CS6).

Strain ACAM2012-CS4 was deposited as ACAM2013 on 29 Aug. 2002 by Acambis Research Limited of Peterhouse Technology Park, 100 Fulbourn Road, Cambridge, CB 1 9PT, United Kingdom with the European Collection of Cell Cultures (ECACC), CAMR, Salisbury, Wiltshire, SP4 0JG, United Kingdom, in accordance with the Budapest Treaty. The strain was given Accession No. 02082969 (Table 2).

In general, a bacterial cell according to the invention expresses a CS antigen on its surface, typically assembled into fimbriae or pili. A candidate cell can be tested for expression of a particular ETEC CS antigen by methods known in the art and described in the Examples herein. For example, in one embodiment a suspension of candidate cells is heated to extract CS antigens and centrifuged. The supernatant is then isolated, subjected to gel electrophoresis and analysed by Western blotting using antigen-specific antibodies or direct protein staining. Typically a strain known to express the particular antigen is included as a positive control for comparative purposes. A negative control may also be included. Suitable methods are known to those skilled in the art. Preferably the level of expression of a CS antigen in a cell of the invention is effective to induce an immune response in a host subject to which the cell has been administered, e.g. as a component of an immunogenic composition such as a vaccine.

Typically in a wild-type ETEC strain, a CS antigen is expressed from an operon of genes. Usually an operon includes genes for one or two structural proteins, a chaperone and an usher protein. The chaperone and usher proteins generally facilitate transport of the structural protein to the surface of the bacterium for assembly into fimbriae. An operon may be located on the bacterial chromosome (as in the case of CS4 and CS2 in some strains) or on a low copy number plasmid (as in the case of CS1, CS3, CS5 and CS6). In addition, each operon is associated with a regulatory gene, the product of which controls the expression of the operon genes. However, this regulatory gene may be located some distance from the operon itself.

Figure 5A:
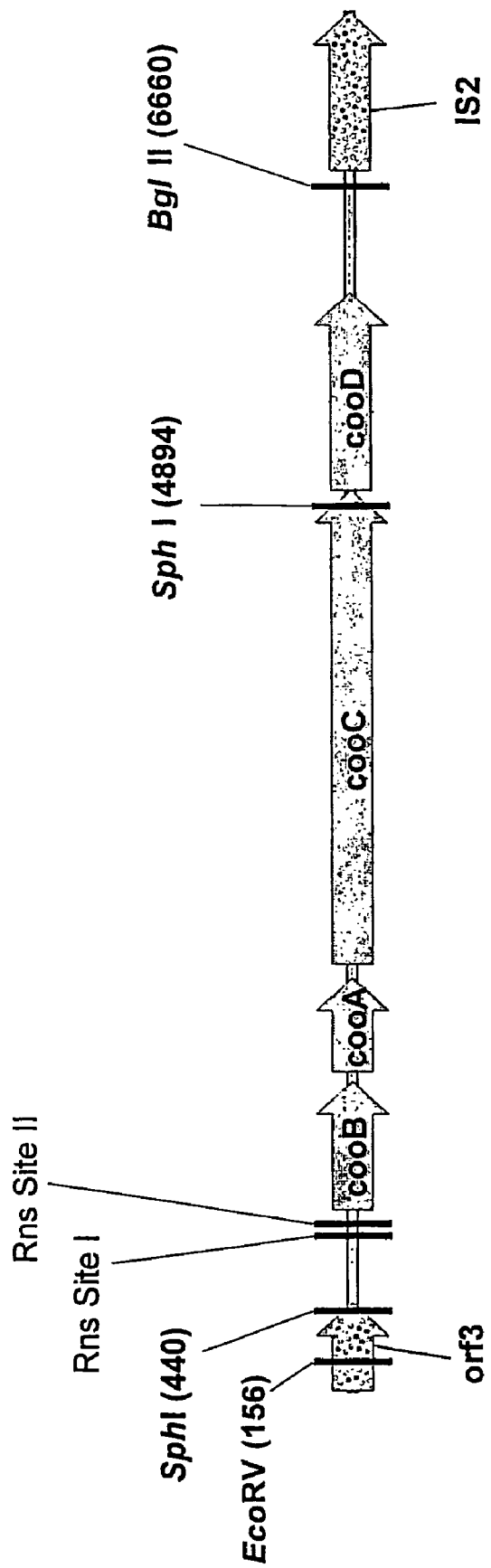
FIG. 5A Structure of the CS1 operon.

The CS1 operon (27) is illustrated in FIG. 5A and consists of four genes cooB, cooA, cooC and cooD (Genbank M 58550, X62495 and X76908). The major pilin protein is encoded by cooA, with cooC and cooD encoding transport functions. cooB is required for assembly. Expression of the operon genes is regulated by a further gene cfaD (GenBank M55609).

The CS2 operon (17) consists of four genes, cotA, cotB, cotC, cotD (GenBank Z 47800) with cotA encoding the major pilin protein. Transport functions are encoded by cotC and cotD. Expression of these genes is regulated by another separate gene rns (GenBank J04166).

The sequence of the CS3 operon (20) may be found at GenBank X16944. The operon include cstA, which encodes a chaperone protein, cstB which encodes a protein with an usher function and cstH which encodes structural protein.

The structure of the CS4 operon, which consists of four genes csaA, csaB, csaC, csaE (Genbank AF296132) is shown in FIG. 1A. csaA encodes a chaperone, csaB encodes a major subunit protein, csaC encodes an usher protein and csaE encodes a fimbrial tip protein. Expression of the CS4 genes is regulated by the cfaD gene (GenBank M55609).

Figure 7A:
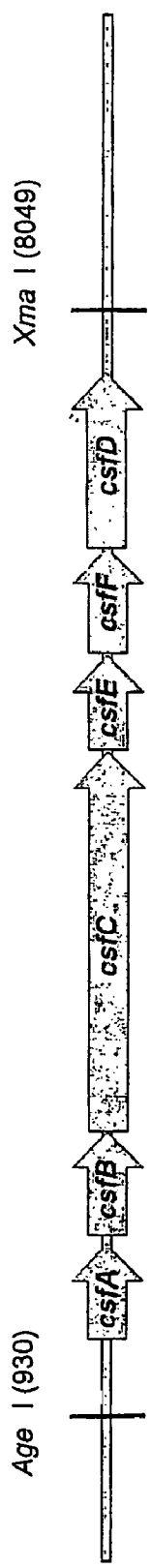
FIG. 7A Structure of the CS5 operon.

The CS5 operon (15)(Genbank AJ 224079) consists of six genes, csfA, csfB, csfC, csfE, csfF and csfD. csfA encodes a major structural protein, csfC encodes a transport protein and csfD encodes a minor structural protein. The operon is illustrated in FIG. 7A. Regulation of the CS5 operon genes is dependent on the presence of bile salts. The gene involved may be csvR (GenBank X60106).

The sequence of the CS6 operon (33, 35) is available at GenBank U04844. The operon includes the cssA and cssB genes which encode structural proteins and the cssC and cssD genes which encode transport proteins.

The sequences of the above operons and genes, specified above by GenBank accession number are also presented in the present sequence listing, as described in the "Brief Description of the Sequences".

Typically, a cell of the invention expresses sufficient genes, including structural, transport and regulatory genes, to enable expression of a given ETEC CS antigen on the bacterial surface. Usually, the antigen is assembled on the surface in fimbriae or pili. Thus, for a given CS antigen, the present cell expresses a structural gene or genes and if necessary, one or more genes, the products of which will aid correct transport to and assembly on the bacterial surface of the structural protein.

Any of the genes referred to above, structural, transport or regulatory, may be useful in the present invention. In one embodiment, an antigenic structural, transport or regulatory protein expressed by a cell of the invention may be encoded by:

(i) a DNA molecule comprising the nucleotide sequence of a gene specified above by GenBank accession number or included in the present sequence listing;

(ii) a DNA molecule which hybridises to the complement of the nucleotide sequence in (a); or (iii) a DNA molecule which encodes the same amino acid sequence as the DNA molecule of (a) or (b) but which is a degenerate form of the DNA molecule of (a) or (b).

A homologue of the polynucleotide sequence in (a) may be used in the invention. Typically, a homologue has at least 40% sequence identity to the corresponding specified sequence, preferably at least 60 or 80% and more preferably at least 90%, 95% or 99% sequence identity. Such sequence identity may exist over a region of at least 15, preferably at least 30, for instance at least 40, 60 or 100 or more contiguous nucleotides.

Methods of measuring polynucleotide homology are well known in the art. For example, the UWGCG Package providing the BESTFIT program can be used to calculate homology, e.g. on its default settings (Devereux et al (1984) Nucleic Acids Research 12, p 387-395). The PILEUP and BLAST algorithms can also be used to calculate homology or line up sequences (typically on their default settings), for example as described in Altschul (1993) J Mol Evol 36: 290-300 or Altschul et al (1990) J Mol Biol 215: 403-10.

A homologue typically hybridises with the corresponding specified sequence at a level significantly above background. The signal level generated by the interaction between the homologue and the specified sequence is typically at least 10 fold, preferably at least 100 fold, as intense as background hybridisation. The intensity of interaction may be measured, for example, by radiolabelling the probe, e.g. with $^{32}P$. Selective hybridisation is typically achieved using conditions of medium to high stringency, for example 0.03M sodium chloride and 0.003M sodium citrate at from about 50° C. to about 60° C.

The homologue may differ from the corresponding specified sequence by at least 1, 2, 5, 10 or more substitutions, deletions or insertions over a region of at least 30, for instance at least 40, 60 or 100 or more contiguous nucleotides, of the homologue. Thus, the homologue may differ from the corresponding specified sequence by at least 1, 2, 5, 10, 30 or more substitutions, deletions or insertions.

A homologue structural gene may be tested by expressing the gene in a suitable host and testing for cross reactivity with antibody specific to the particular antigen. A homologue transport or regulatory gene may be tested for the ability to complement the activity of the endogenous transport or regulatory gene in a bacterial cell.

A transport gene may be endogenous to the structural gene or genes with which it functions. Thus the present cell may comprise both the structural gene or genes and one or more of the transport genes of a given CS operon. In a preferred embodiment, a cell of the invention comprises a complete operon for a given CS antigen.

In a further embodiment, a cell of the invention may comprise less than the whole operon for a given CS antigen. For example, a cell of the invention may comprise the structural gene or genes for a given CS antigen, without one or more of the endogenous transport genes. In such a cell, one or more heterologous transport genes function to transport the structural protein to the surface of the cell. Thus, for example, structural CS1 gene products may be transported to the surface by the action of the transport genes of CS2 (cot C and cot D) and vice versa (17). Thus, a cell according to the invention may comprise an incomplete operon for a given CS antigen, provided that the antigen is expressed on the bacterial surface. For example, the cell may express the structural gene or genes of a particular operon, accompanied by one or more heterologous but complementary transport genes.

It is generally preferred that the present cell expresses a CS antigen stably; a cell exhibiting stable antigen expression is a better candidate for an ETEC vaccine. As described above, in native ETEC isolates, the CS2 and CS4 operons are generally located on the bacterial chromosome and the CS1, CS3, CS5 and CS6 operons are generally carried on low copy number plasmids. Thus, in the absence of specific selection mechanisms, endogenous CS genes are generally stably maintained and expressed over many generations. The present cell generally comprises one or more heterologous polynucleotide sequences encoding one or more CS antigens. Such heterologous polynucleotide sequences may be present in the cell on a plasmid or may be located, as a result of an insertion event, in the bacterial chromosome.

Where a heterologous polynucleotide sequence is carried on and expressed from a plasmid, the plasmid is preferably stably maintained. Stable maintenance is also desirable for ETEC CS bearing native plasmids—this may become an issue where, for example, a native plasmid is manipulated for attenuation purposes as described below. Methods for enhancing plasmid stability are discussed below.

Preferably a heterologous polynucleotide encoding a CS antigen is positioned in the bacterial chromosome, for example by a recombination event. A chromosomal location generally provides more stable expression than a plasmid location and would also result in a heterologous operon being present at a copy number similar to that occurring in wild-type strains. Where the cell has been obtained by introduction of a heterologous CS antigen encoding polynucleotide into an ETEC strain which endogenously expresses a CS antigen, chromosomal placement also helps to prevent "overloading" with the additional antigenic protein and to minimise interference with regulation of expression of the endogenous antigenic proteins.

In a wild type ETEC strain, regulation of expression of a CS operon is often effected by a gene which is at some distance from the structural gene or genes. In the present cell, expression of a heterologous CS antigen may be regulated by a regulatory gene native to the cell, a homologue thereof, or a by a heterologous regulatory gene. Thus, where the present cell is obtained by introduction of a heterologous polynucleotide into an E. coli strain which endogenously expresses an ETEC CS antigen, expression of the heterologous sequence may be regulated by a regulatory gene associated with the endogenous CS operon. Without wishing to be bound by theory, it is proposed that host specific regulatory proteins are able to interact with the genes that have been introduced artificially and changed in mode of regulation. Thus, for example, when CS4 genes are introduced into a CS5/CS6 expressing E. coli strain, without the native CS4 regulatory gene cfaD, expression of the CS4 genes may be regulated by the endogenous CS5 regulatory gene, which is dependent on the presence of bile salts. However, if a rns regulator (a homologue of cfaD) is also introduced to this cell, expression of the CS4 gene becomes bile salt independent. Conversely, when CS5 genes are introduced into a CS4/CS6 strain, without the native regulatory gene, expression of the CS5 genes may be regulated by the CS4 regulatory gene cfaD.

In one embodiment it may be preferable for CS antigen expression in the present cell to be bile salt independent. For example, this may be advantageous if a cell of the invention is to be "preloaded" with CS antigen, in preparation for vaccine use, since animal product free medium may be used to induce CS antigen expression.

A cell according to the invention has not been isolated in nature. Accordingly, the present cell is generally obtainable by introducing a polynucleotide (e.g. DNA) encoding a heterologous ETEC CS antigen into a suitable bacterial host cell.

Suitable host strains (or starter strains) from which the present cell may be produced have been described above. Preferably the host strain is an ETEC strain which endogenously expresses an ETEC CS antigen. In particular the host strain may express CFA/II (includes CS1/CS3 and CS2/CS3) or CFA/IV (includes CS4/CS6 or CS5/CS6). In one embodiment the host strain is selected from deposited strains ACM2005, ACM2003, ACM2002, ACM2004, ACAM2007, ACAM2008, ACAM2009 or ACAM2012 listed in Tables 1 and 2 or descendents of these cells. A descendent is any cell derived from the deposited cell. A descendent may include a cell with one or more further attenuating mutations, such as those described herein. A descendent may include a cell engineered to express a heterologous antigen, also as described herein.

In general the polynucleotide introduced into the host strain comprises one or more structural genes for a CS antigen. Preferably the polynucleotide includes the structural gene or genes for at least one antigen selected from ETEC CS1, CS2; CS3, CS4, CS5 and CS6. GenBank accession numbers for these gene sequences are given above and in Table 5. Sequences corresponding to those entered under the accession numbers are included in the present sequence listing.

The process for making the present cell may also comprise the step of introducing into a cell a polynucleotide comprising one or more transport (typically chaperone or usher) genes. In one preferred embodiment, the method comprises introducing to a suitable cell a polynucleotide comprising one or more structural genes for an ETEC CS antigen and one or more complementary transport genes. Alternatively the structural genes and the transport genes may be present on separate polynucleotides. Preferably a method is used which comprises introducing a polynucleotide comprising a heterologous ETEC CS operon. In a further embodiment, transport genes, endogenous to an ETEC host strain may act on an antigen, including a heterologous antigen, in the cell, aiding its progression to the cell surface.

As already described, regulation of expression of a heterologous ETEC CS antigen in the present cell may be carried out by a regulatory gene endogenous to or already present in the host strain. Alternatively or additionally, the method of deriving the present cell may comprise the step of introducing into a cell a polynucleotide comprising a suitable regulatory gene. A regulatory gene when introduced in this way may be present on the same or a different polynucleotide to the structural gene or genes and/or any transport genes which are being introduced. Typically the regulatory gene will be one which regulates expression of the subject ETEC CS antigen in a native ETEC strain or a homologue thereof. Therefore in one embodiment the present process comprises introducing to a suitable cell a polynucleotide comprising a heterologous ETEC CS operon together with its native regulatory gene.

A polynucleotide which is to be introduced into a cell according to the present invention may take any suitable form. Typically the polynucleotide is a plasmid vector. In general, the polynucleotide bears a selectable marker.

The polynucleotide may comprise one or more expression control elements, such as a promoter, enhancer or transcription terminator sequence, operably linked to a gene or genes which need to be expressed. For example, a suitable plasmid expression vector may be used. Suitable vectors are known in the art.

Preferably a polynucleotide, introduced into a cell in accordance with the invention, is to be inserted in the bacterial cell chromosome, for example, by homologous recombination. Methods for causing chromosomal insertion are known in the art. For instance, the polynucleotide may be introduced on a suitable suicide vector. For example, suicide vector pJCB12 described herein may be used.

Methods for introducing foreign DNA into prokaryotic cells are known in the art. Examples of suitable methods include conjugation and electroporation. Transformant colonies may be screened and selected for correct uptake of the heterologous nucleic acid using standard screening and selection procedures. Selected transformants may be tested for surface expression of a given ETEC CS antigen using the screening procedures described above.

In a preferred embodiment the present method comprises:
(i) introducing a polynucleotide encoding ETEC CS4 antigen into a CS5/CS6 ETEC cell; or
(ii) introducing a polynucleotide encoding ETEC CS1 antigen into an CS2/CS3 ETEC cell; or
(iii) introducing a polynucleotide encoding ETEC CS5 antigen into a CS4/CS6 ETEC cell; or
(iv) introducing a polynucleotide encoding ETEC CS4 antigen into a CS1/CS3 ETEC cell.

It is generally preferred that a cell of the invention is attenuated with respect to a wild type ETEC cell. Thus, the present cell typically has reduced virulence, such that it does not cause ETEC associated disease such as diarrhoea, but is nevertheless capable of stimulating an immune response. This is particularly so when the cell is for use in a vaccine to combat ETEC associated disease such as diarrhoea. Use of an attenuated cell in such vaccine generally results in a lower probability of a vaccinated subject experiencing side-effects, such as diarrhoea symptoms.

A cell of the invention may be attenuated in a number of ways, generally by some kind of mutation. For example, toxicity may be reduced by use of a cell which does not express the ETEC associated toxins or does not express these toxins in a functional or toxic form. Alternatively, or additionally, attenuation may arise by mutation of a further bacterial gene, typically to cause its inactivation or deletion (e.g. by replacement).

Colonisation of a host small intestine by ETEC cells is accompanied by the secretion of enterotoxins. Two types of enterotoxins identified in ETEC strains are the heat labile toxin (LT) and the heat stable toxin (ST). LT is highly homologous in structure to the cholera toxin, a multisubunit protein of the form $AB_5$. The A sub-unit is the active component in the toxin, which functions to increase the activity of adenylate cyclase. This is delivered into host cells by the B subunits, which bind to gangliosides on the cell surface. ST is a small (19 amino acids) non-immunogenic polypeptide that has guanylate cyclase stimulating activity. In addition, it has been demonstrated recently that a large proportion of ETEC strains also produce EAST1, a heat stable toxin, similar in size and mode of action to ST but different in sequence, which was originally identified in enteroaggregative E. coli strains.

Thus, in one embodiment a cell of the invention generally does not express functional ETEC toxins, such as LT, ST and EAST1. Such a cell may for example be referred to as a toxin-minus strain. GenBank accession numbers for these toxins are given in Table 5.

Attenuation may arise because the cell is derived or produced from a non-ETEC bacterial cell which does not naturally or endogenously express one or more of the ETEC toxins. Alternatively, the cell may derive from an ETEC cell which is attenuated with respect to the ETEC toxins. Such an ETEC strain may arise as a result of spontaneous mutation, for example a deletion event. Alternatively, or additionally, a toxin-minus strain may be produced using genetic engineering or molecular biology techniques.

Clinical isolates obtained from a long term epidemiological study carried out by scientists at the US NAMRU3 facility in Cairo are listed in Table 3. A number of these isolates are toxin-minus with respect to at least one of the toxins referred to above. Some of these isolates have been used to produce further attenuated strains as described below.

An example of a spontaneous toxin minus strain is E1392/75-2A (CFA/II, ST minus, LT minus) (10) (Table 1). Examples of ETEC strains which have been manipulated to ensure specific removal of all known toxin genes are those with accession numbers 01090304, 1090305, 01090306 (derived from strains H, E, and J in Table 3 respectively) and 02082964, 02082965, 02082966 and 02082968 as described above and shown in Tables 1 and 2. Deposited strain 01090302 is also a toxin minus strain.

A bacterial cell of the invention may be attenuated due to mutation of a further gene. The attenuation may, for example, be brought about by deleting or inactivating one or more of the following genes: aroA, aroC, aroD, aroE, pur, htrA, ompC, ompF, ompR, cya, crp, phoP, phoQ, surA, rfaY, dksA, hupA, invE and clpB. Preferred combinations of genes include:
at least one aro gene (e.g. aroA, aroC, aroD or aroE) and at least one omp gene (e.g. ompC, ompF or ompR);
at least one aro gene (e.g. aroA, aroC, aroD or aroE) and the htrA gene;
aroC, ompF and ompC.

For example strains PTL002 and PTL003 (Accession number 01090302) were derived from strain E1392/75-2A above by mutation of aroC/ompR and aroC/ompC/ompF respectively.

Furthermore, it is generally preferred that any antibiotic resistance genes are removed from a bacterial cell of the invention before use in a vaccine. Bacteria isolated from the wild often contain antibiotic resistance genes, such as resistance genes against ampicillin, streptomycin, sulphmethoxazole, kanamycin, trimetheprim and tetracycline. These genes can be removed using the suicide vector and methods described herein or by methods known to those skilled in the art.

As noted above, attenuation of the present bacterial cell may arise from one or more mutations in the bacterial genome. A mutation(s) which prevents expression of an enterotoxin or other gene generally deletes or inactivates the gene. Generally there is a complete knock-out of the function of the gene. This may be achieved either by abolishing synthesis of any polypeptide at all from the gene or by making a mutation that results in synthesis of non-functional polypeptide. In order to abolish synthesis of polypeptide, either the entire gene or its 5'-end may be deleted. A deletion or insertion within the coding sequence of a gene may be used to create a gene that synthesises only non-functional polypeptide (e.g. polypeptide that contains only the N-terminal sequence of the wild-type protein). In the case of a toxin gene, the mutation may render the gene product non-toxic.

A mutation is generally a non-reverting mutation. This is a mutation that shows essentially no reversion back to the wild-type for example when the bacterium is used as a vaccine. Such mutations include insertions and deletions. Insertions and deletions are preferably large, typically at least 10 nucleotides in length up to the length of the entire gene or coding sequence, for example from 10 to 600 nucleotides. Preferably, the whole coding sequence or whole gene is deleted.

The mutations are typically site-directed. They may be specific or selective to the toxin gene or other gene. For example, in the case of deleting or inactivating the ST gene in a CFA/I or CS5/CS6 strain, the mutation must specifically target the ST gene without deleting or inactivating the (closely-linked) CFA/I gene, CS5 gene or CS6 gene.

A mutation may arise from use of a suicide vector. In particular, the pJCB12 suicide vector may be used. This vector is described in UK Patent Application No. 0121998.9, and also in the International patent application claiming priority from that UK application and filed by Acambis Research on the same day as this International application. The contents of that International application are hereby incorporated by reference. The vector allows specific and reliable targeting, and is typically less than 5 kb in size (for example from 2.5 to 5 kb or 2.5 to 4 kb).

An attenuating mutation may be introduced using a suicide vector or by other methods known to those skilled in the art (26). Appropriate known methods include cloning the DNA sequence of the wild-type gene into a vector, e.g. a plasmid, and inserting a selectable marker into the cloned DNA sequence or deleting a part of the DNA sequence, resulting in its inactivation. A deletion may be introduced by, for example, cutting the DNA sequence using restriction enzymes that cut at two points in or just outside the coding sequence and ligating together the two ends in the remaining sequence. Alternatively, and more usually now, a mutant allele in which the flanking regions of a target gene are amplified separately and linked directly together in a separate overlap PCR reaction, with omission of the intervening target sequence, can be constructed (31). A plasmid carrying the mutated DNA sequence can be transformed into the bacterium by known techniques such as electroporation and conjugation. It is then possible by suitable selection to identify a mutant wherein the inactivated DNA sequence has recombined into the chromosome of the bacterium and the wild-type DNA sequence has been rendered non-functional by homologous recombination.

In another embodiment of the invention, the present cell further expresses an antigen that is not expressed by the native bacterium (a "heterologous antigen"), in addition to an ETEC CS antigen. This is particularly useful where the cell is to be used in a vaccine, since the presence of additional antigens may enhance the immune response generated. In the case that the bacterium is an ETEC bacterium, the antigen may be from another strain of ETEC, so that the vaccine provides protection against the other strain. Furthermore, the bacterium may be engineered to express more than one such heterologous antigen, in which case the heterologous antigens may be from the same or different strains.

The heterologous antigen may be a complete protein, a part of a protein containing an epitope or a fusion protein. Useful antigens include ETEC non-toxic components or non-toxic mutants of *E. coli* LT (e.g. the B subunit and mutants of the A subunit, accession numbers for which are given in Table 5), and LT-ST fusion proteins (1, 7-9)

The DNA encoding a heterologous antigen may be expressed from a promoter that is active in vivo. A promoter may be a strong promoter, such as the tac promoter or a derivative thereof. Promoters that have been shown to work well are the nirB promoter (6, 16), the htrA promoter (16), the pagC promoter (13) and the ssaH promoter (32). For expression of derivatives of LT, CT or ST, the wild-type promoters could be used.

As noted, it is preferred that a plasmid expressing a heterologous antigen is stably maintained in the present cell. In order to prevent loss of a plasmid expressing a heterologous antigen or of a native plasmid, an element may be added to the plasmid which enhances its stability.

There are a number of "toxin/antitoxin" plasmid stability determining systems known, for example parDE (25) from plasmid RP4 (2), and hok/sok (also known as parB from plasmid R1 or pndAB from plasmid R483 (18, 19)) which could be used to improve plasmid stability. These systems encode two functions: firstly a toxic entity that would kill cells in which it is expressed, which has a long biological half-life, and secondly an antitoxic entity that prevents this killing but has a short biological half-life. In the event that a plasmid encoding these functions is segregated during division the daughter cell which does not contain the plasmid exhausts its supply of antitoxin and is killed by the more persistent toxin moiety. Thus, only cells that continue to harbour the plasmid are maintained in the growing population.

Another system that may be used to enhance the stability of a plasmid in accordance with the invention is a multimer resolution system. Multimer resolution systems confer stability by resolving plasmid multimers into single plasmid copies, hence decreasing the chance of plasmid free daughter cells being generated by random segregation at cell division. A number of site-specific recombination systems which act to resolve plasmid multimers into monomers have been identified. In accordance with such a system, the plasmid to be stabilised contains a recognition site for a site-specific recombinase and the host cell contains a DNA sequence encoding a site-specific recombinase. The recombinase acts on the recognition site and thereby directs proper segregation of the plasmid during cell division. The recombinase may be encoded on the plasmid to be stabilised or in the chromosome of the host cell.

The recombinase is generally a resolvase. Examples of resolvases which may be used in the invention include the Cre recombinase of plasmid P1, the *E. coli* XerC (ArgR) protein, the D protein recombinase of plasmid F, the ParA recombinases of plasmids RP4 and RK2, the site-specific recombinase of plasmid R1, resolvases encoded by the Tn3-like transposable genetic elements and the Rsd resolvase from the *Salmonella dublin* virulence plasmid.

The recognition elements which may be used in the present invention include those for the above recombinases. Any recognition element recognised by the site-specific recombinase employed may be used. Suitable recognition elements include those sites recognised by the XerC site-specific recombinase, such as the cer site of plasmid ColE1 and the similar ckr site of plasmid ColK (29), the psi site of plasmid pSC101 and the cer like site of plasmid pHS-2 from *Shigella flexneri*. Other recognition elements which may be used include the crs site from the *Salmonella dublin* virulence plasmid, the loxP site of plasmid P1, the rfs site of the F plasmid and the res site of the Tn3-like transposable genetic element In a particularly preferred embodiment of the invention, the recombinase, is the Rsd resolvase which acts via the crs recognition element. The Rsd/crs system is described in detail in WO 02/28423.

A cell according to the invention is suitable for use in the manufacture of a composition or medicament to target bacterial infection.

Typically the bacterium is ETEC. For example, compositions including the present cell may be used against ETEC associated disease, such as diarrhoea. In general, the composition comprises at least one cell strain of the invention and a pharmaceutically acceptable carrier or diluent. The composition may also comprise one or more other bacterial strains or components.

A suitable cell for inclusion in the composition may be any of those described herein. In general the composition is capable of generating an immune response in an individual to at least the three or more CS antigens expressed in the cell. This capability can be tested by immunisation studies. For example, the composition may be administered to an animal such as a human and tests may be made for generation of an antibody or T-cell response specific for the three or more CS antigens. Antiserum generated following administration of a composition to an animal can be evaluated for ability to specifically bind either the cell expressing the CS antigens or purified CS antigen. Subsequently the animal may be challenged with an ETEC strain to evaluate whether there is a protective immune response.

Preferably, an immunogenic composition can generate an immune response against at least CFA/I, CFA/II and CFA/IV strains. Thus the immunogenic composition preferably comprises one or more bacterial strains according to the invention such that each of the above antigens is represented. The composition may comprise one or more other strains. In one embodiment, the composition of the invention comprises:
  (i) a strain which expresses CS 1, CS2 and CS3
  (ii) a strain which expresses CS4, CS5 and CS6; and
  (iii) a strain which expresses CFA/I.

Examples of CFA/I strains include ACM2001 and ACAM2010 listed in Table 2.

In a preferred embodiment, the immunogenic composition is a vaccine. For example a vaccine against an ETEC associated disease such as diarrhoea. The vaccine is generally a live attenuated vaccine, comprising one or more live attenuated bacterial strains, at least one of which is a cell strain according to the invention.

Traditionally, due to the restricted expression of CS antigens by ETEC cells, an effective vaccine has had to include a minimum of 5 bacterial strains. However, by providing the present cells, the present invention now provides an anti-ETEC vaccine which may comprise fewer than 5 strains—for example 3 or 4 strains.

The present composition or vaccine may be formulated using known techniques for formulating attenuated bacterial compositions or vaccines. The composition or vaccine is advantageously presented for oral administration, for example as a dried stabilised powder for reconstitution in a suitable buffer prior to administration. Reconstitution is advantageously effected in a buffer at a suitable pH to ensure the viability of the bacteria. In order to protect the attenuated bacteria and the composition or vaccine from gastric acidity, a sodium bicarbonate preparation is advantageously administered with each administration of the vaccine. Alternatively the composition or vaccine is presented in a lyophilised encapsulated form.

The composition or vaccine may be used in the treatment, such as the vaccination, of a mammalian host, particularly a human host. An infection caused by a microorganism, especially a pathogen, may therefore be targeted or prevented by administering an effective dose of a vaccine prepared according to the invention. The dosage employed may ultimately be at the discretion of the physician, but will be dependent on various factors including the size and weight of the host and the type of composition or vaccine formulated. However, a dosage comprising the oral administration of from $10^7$ to $10^{11}$, e.g. from $10^8$ to $10^{10}$, bacteria per dose may be convenient for a 70 kg adult human host.

EXAMPLES

The following Examples serve to illustrate the invention.
Unless otherwise indicated, the methods used are standard biochemistry and molecular biology techniques (2, 26).
Materials and Methods
Strains This work was carried out using a number of clinical isolates of ETEC. Strain E1392/75-2A (9) was provided by the National Collection of Type Cultures and Pathogenic Fungi, Central Public Health Laboratories, Colindale, UK. This is a spontaneous toxin-loss variant of Strain E1392, originally isolated in Hong Kong. Attenuating deletions were introduced into the aroC, ompC and ompF genes at Acambis, UK to create vaccine strain PTL003 (Deposited strain 01090302, Tables 1 and 2) (31). The other wild-type strains were isolated at Naval Medical Research Unit 3 (NAMRU3), Cairo, Egypt from patients with diarrhoea. Toxin genes were deleted from these strains and attenuating deletions were introduced into the aroC, ompC and ompF genes at Acambis, UK (UK Patent application 0121998.9). The strains used in the Examples, their genotypes/phenotypes and where appropriate, the accession numbers for deposited strains are described in Tables 1 and 2.

The Examples also use three laboratory strains of *E. coli* which carry the pir gene on the chromosome. These are SY327λpir (23), SM10λpir (28) and DH5αλpir (P Barrow, Institute for Animal Health, Compton).
Growth of Strains All media used for maintenance and growth of strains during vaccine development were made from certified animal-free components. Basic LB media was composed of 10 g/l soy peptone, 5 g/l yeast extract and 10 g/l NaCl. Agar (15 g/l) and antibiotics were added as required. CFA agar was used for analysis of vaccine strains and was composed of 10 g/l agar, 10 g/l soy peptone, 1.5 g/l yeast extract, 0.005% $MgSO_4$, 0.0005% $MnCl_2$ and 0.15% bile salts.

Preparation of CS Proteins by Heat Extraction

Strains were grown overnight in LB media, with antibiotics as required, at 37° C. with shaking. A 10 µl aliquot was then spread onto a 15 ml CFA-agar plate containing antibiotics where appropriate. The plate was incubated overnight at 37° C. until a confluent lawn was achieved. The bacteria were then scraped off the plate into 0.5 ml PBS. 10 µl of this cell suspension was added to 1 ml PBS and the $OD_{600}$ was measured ($OD_{600}$ of $1=1\times10^9$ cells/ml). An aliquot of cell suspension containing $10^9$ cells was centrifuged at 13000 rpm for 5 min and the pellet was resuspended in 10 µl PBS. The sample was heated at 65° C. for 10 min and then centrifuged at 13000 rpm for 5 min. The supernatant was retained and added to 10 µl 2× Novex Tris-Gly sample buffer (Invitrogen) containing 2 µl 1M DTT. Samples were heated at 95° C. for 5 min and then analysed by SDS-PAGE on 14% Novex Tris-Gly gels (Invitrogen) followed by direct staining with SimplyBlue SafeStain (Invitrogen) or by immunoblotting.

Detection of Proteins by Western Blot

Samples were electrophoresed on 14% Novex Tris-Gly gels at 125V until the dye front was about 0.5 cm from the bottom of the gel. SeeBlue Plus2 markers (Invitrogen) were used as molecular weight standards. Transfer onto 0.45 µm nitrocellulose membrane (LC2001, Invitrogen) was performed for 1 h at 25V according to the manufacturer's instructions (XCell II Blot Module EI 9051 instruction manual, Invitrogen). After transfer, the membrane was blocked for 1 h using PBST (Sigma P-3813, 0.01M Phosphate-buffered saline (0.138M NaCl, 0.0027M KCl) with 0.05% Tween pH7.4) and 5% Marvel dried milk powder. The membrane was washed four times (10 min each) in PBST containing 1% Marvel. The blot was incubated with primary antibody in PBST/1% Marvel for 1 hour and then washed four times as before. The blot was incubated with secondary antibody (anti-rabbit HRP conjugate, Sigma A4914) in PBST/1% Marvel for 1 h and then washed four times as before and twice in PBST alone. The blot was developed using the Pierce Super Signal West Pico reagent according to the manufacturer's instructions and exposed to X-ray film for various time periods.

PCR Reactions

Except where otherwise described, two types of PCR reactions were formed: reactions to amplify DNA fragments for cloning and reactions for screening and analysis of plasmids/strains. To obtain fragments for cloning, the high fidelity enzyme Pfu Turbo (Stratagene) was used according to the protocols set out in the Instruction Manual #039001b. For screening clones, and cloning the rns gene, Taq polymerase (Invitrogen, Catalogue number 10342-020) was employed according to the manufacturer's instructions.

Oligonucleotides

The sequences of the oligonucleotides, for example the primers, used in the Examples are given in Table 4.

Example 1

Production of a CS4, CS5, CS6 Strain (CS4 Expressed in a CS5/CS6 Strain)

1.1 Cloning the CS4 Operon

Figure 1C:
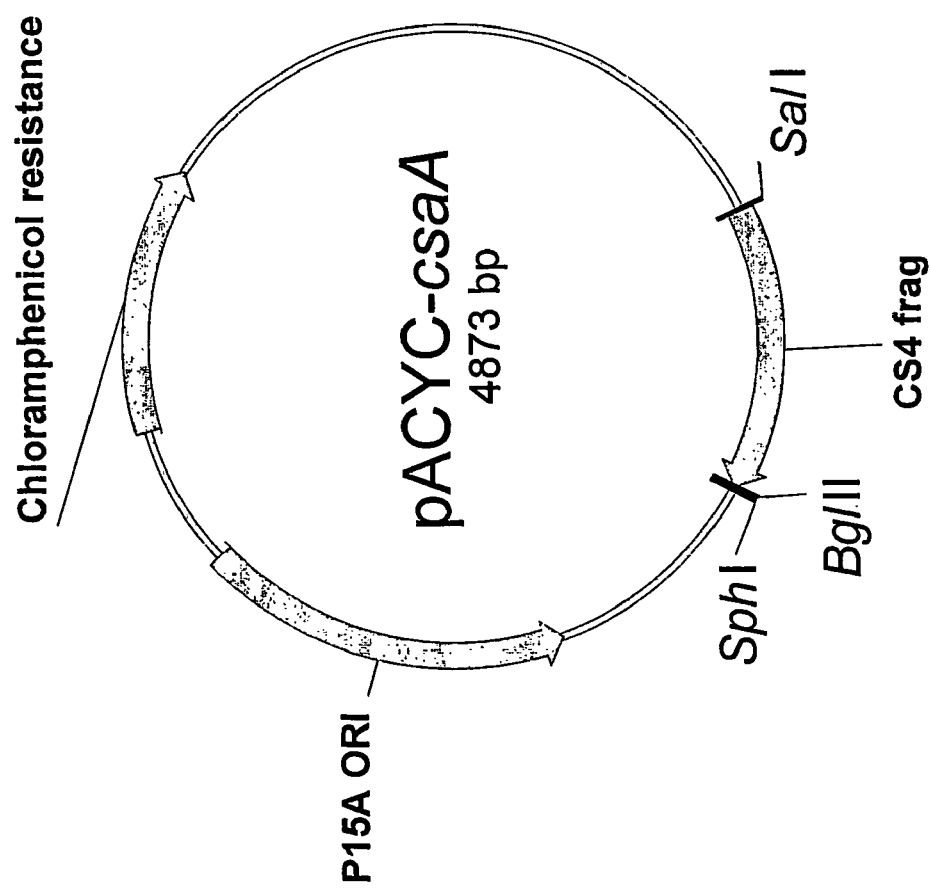

The sequence of the CS4 operon has been published in Genbank (Reference number AF296132). Computer-aided restriction analysis of this sequence (using the VectorNTi program Version 7, Informax) revealed two BglII sites, one (site (a)) in the first gene of the operon (csaA) and one (site (b)) downstream of the last gene in the operon (csaE) (FIG. 1A). Thus the major part of the operon could be cloned by restriction digestion using these BglII sites, avoiding any PCR-related errors. However, it was necessary to clone the 5' region of the operon by PCR amplification since there were no suitable restriction sites that would permit direct cloning. Two PCR primers (Primer 47151 and Primer 47152) were used to amplify the csaA gene up to and including the BglII site, using chromosomal DNA from Strain WS2252-A (CS4/CS6, Table 1) as template. The forward primer, Primer 47151, introduced a SalI restriction site upstream of the csaA gene, whilst the reverse primer, Primer 47152, introduced an SphI site downstream of the BglII site. These sites were used to clone the 723 bp PCR product into the stable, low-copy number vector pACYC184 ((5); supplied by NEB, FIG. 1B) which was also digested with SalI and SphI. This vector was named pACYC-csaA (FIG. 1C). In this construct, site (a) in FIG. 1A is preserved and can be used for cloning the large fragment from the CS4 operon (between the (a) and (b) sites).

Figure 1D:
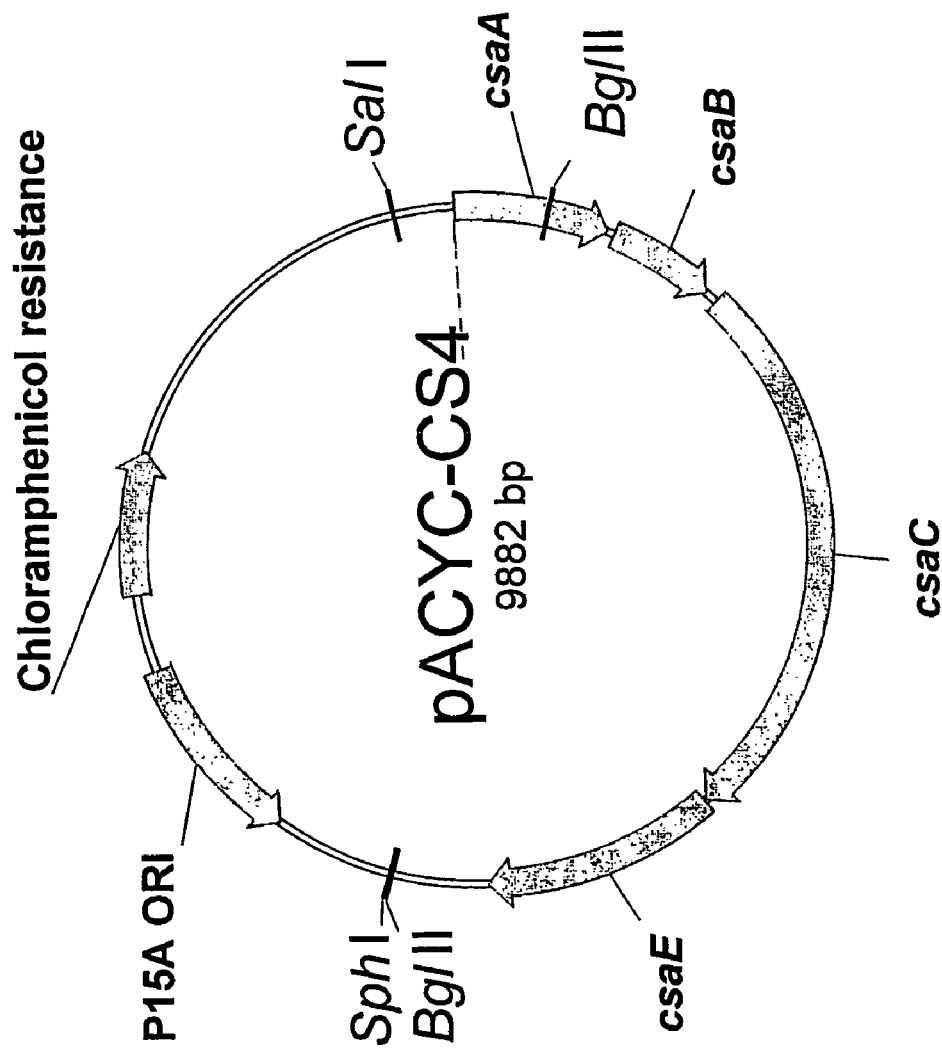

Thus, another portion of chromosomal DNA from Strain WS2252-A was digested with BglII and subjected to agarose gel electrophoresis. DNA fragments of approximately 5 kb were isolated from the gel using a QIAquick gel extraction kit and were ligated into pACYC-csaA that had been digested with BglII and treated with Calf Intestinal Phosphatase (CIP). Ligation mixture was used to transform E. coli XL10 Gold KanR and transformed colonies were selected on agar plates containing chloramphenicol. Colonies with plasmids containing the 3' region of the CS4 operon in the correct orientation were detected by PCR using Primer 47151 and Primer 47150 that binds within csaC (FIG. 1A). Correct plasmids containing the complete CS4 operon were named pACYC-CS4 (FIG. 1D).

1.2 Expression of CS4

1.2.1 Expression of CS4 from the Plasmid pACYC-CS4

The plasmid pACYC-CS4 was used to transform two strains: 'Strain K' is a derivative of a CS4/CS6 strain that has spontaneously lost its CS4 gene such that it expresses CS6 only; ACAM2006 is an attenuated, toxin-minus derivative of WS2773-E, a CS5/CS6 ETEC strain. The strains were designated Strain K-pCS4 and ACAM2006-pCS4 respectively and were maintained on chloramphenicol.

CS proteins were purified by heat extraction from Strain K-pCS4 and ACAM2006-pCS4 as described in the "Materials and Methods". For comparison, Strain WS-2252A, a CS4/CS6 strain, and ACAM2006 were similarly analysed. After heating for 5 min at 95° C., the samples were analysed by electrophoresis on 14% Tris-Gly polyacrylamide gels (Novex). Bands were visualised by staining with SimplyBlue SafeStain (Invitrogen) (FIG. 2A) or by Western Blot using CS4-specific antibodies (FIG. 2B) as described in the "Materials and Methods".

CS4 antigen was clearly detected in the control strain, WS-2252A, and also in Strain K-pCS4 indicating that the cloned operon was intact and functioning. However, CS4 was not detected in either ACAM2006 or in ACAM2006-pCS4. It seemed likely that this disparity was due to the presence of different regulatory mechanisms in Strains K and ACAM2006. The cfaD gene product, a protein that is present in Strain K but not in ACAM2006, normally regulates the CS4 operon. Expression of the CS5 operon is poorly understood. The csvR gene has been isolated from another CS5/CS6 strain and is 87% homologous to cfaD. The protein product is able functionally to replace activity of cfaD to mediate CFA/I expression, however, it's role in expression of CS5 is unclear (11, 14). CS5 biosynthesis also differs from expression of CS1, CS2, CS3, CS4 and CS6 in that bile-salts are necessary for production of fimbriae. It was speculated that it might be necessary to add bile salts to the CFA agar used for growth of ACAM2006-pCS4 in order to stimulate expression of the CS4 operon. CS proteins were purified by heat extraction from Strains ACAM2006, ACAM2009 (an attenuated derivative of WS2252A) and ACAM2006-pCS4 as described in the "Materials and Methods". Samples were analysed by electrophoresis on 14% Tris-Gly polyacrylamide gels (Invitrogen) and bands were visualised by staining with SimplyBlue SafeStain (Invitrogen) or by Western blot using CFA/IV specific antibodies as described in the "Materials and Methods". In the presence of bile salts good quantities of CS4 and CS5 were detected in the CFA preparation from ACAM2006-pCS4 (FIGS. 2C and D) indicating that a regulator protein present in ACAM2006, possibly csvR, can activate the CS4 operon and induce expression. CS6 was also detected in ACAM2006-pCS4. Although the levels of this antigen are low they are similar to those seen in CS5/CS6 strains such as ACAM2006. Hence we demonstrated that it was possible to express all three CFA/IV CS proteins within a single strain.

Figure 2:
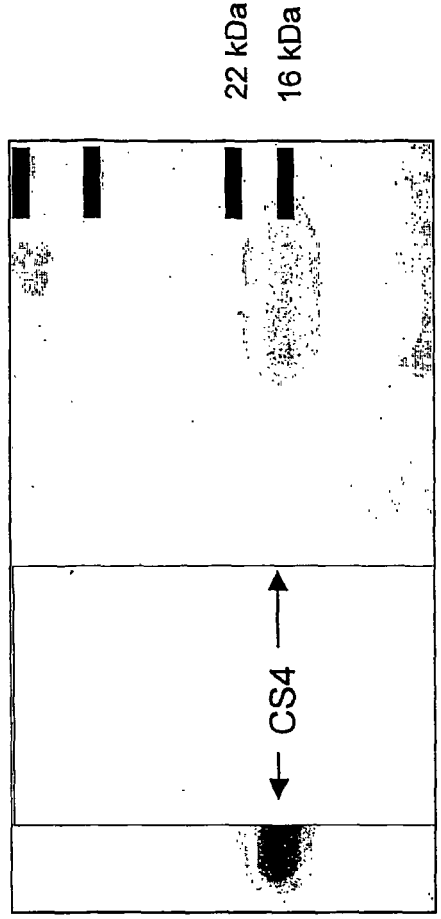
FIG. 2A SDS PAGE analysis of CS antigen expression in strains WS-2252A, ACAM2006, ACAM2006-pCS4 and Strain K-pCS4. Staining is with Simply Blue Safe Stain (Invitrogen).
FIG. 2B SDS PAGE analysis of CS antigen expression in strains WS-2252A, ACAM2006, ACAM2006-pCS4 and Strain K-pCS4, using Western Blotting.
FIG. 2C SDS PAGE analysis of the effect of bile salts on CS antigen expression in strains ACAM2006, ACAM2009 and ACAM2006-pCS4. Staining is with Simply Blue Safe Stain (Invitrogen).
FIG. 2D SDS PAGE analysis of the effect of bile salts on CS antigen expression in strains ACAM2006, ACAM2009 and ACAM2006-pCS4, using Western Blotting.
FIG. 2E SDS PAGE analysis of CS antigen expression in the absence of bile salts in strain ACAM2006-pCS4 transformed with pGEM-rns. Staining is with Simply Blue Safe Stain (Invitrogen).
Figure 2:
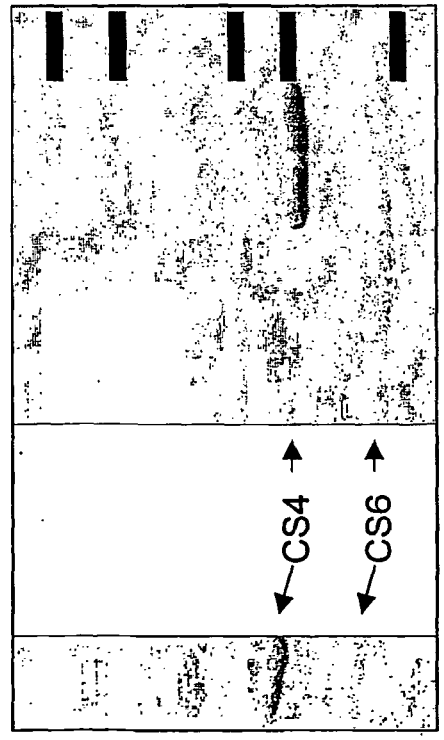
Figure 2:
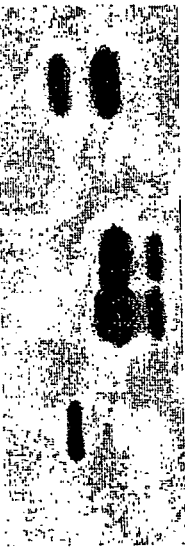
Figure 2:
Figure 2E:
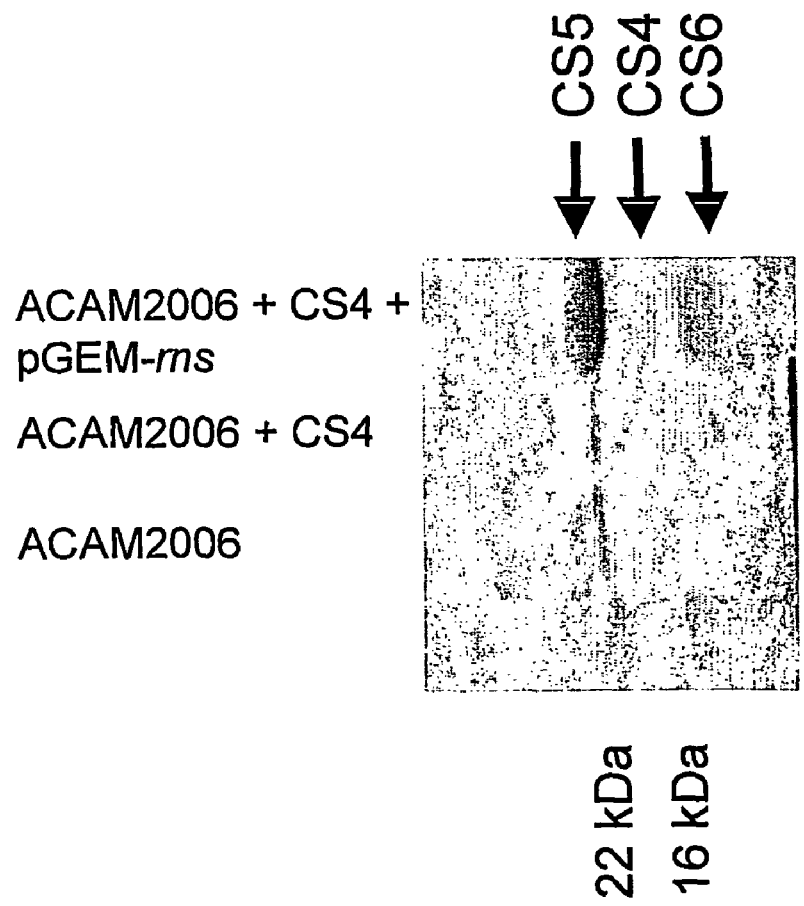

Bile-salt dependent regulation should work well in vivo in a vaccine strain where expression of CS proteins is expected to mimic that seen in a natural infection However, it may be possible to change the pattern of regulation by introduction of a different regulator such as rns or cfaD (rns is homologous to cfaD). To investigate this an rns gene was isolated from strain E1392-2A by PCR using primers RNS-03 and RNS-04. The PCR product was amplified using Taq polymerase that leaves an 'A' overhang and permits the use of cloning vector pGEM-T Easy (Promega) for cloning. The PCR construct was cloned into the vector according to the supplier's instructions to create plasmid pGEM-rns. This plasmid was introduced into ACAM2006-pCS4 by electroporation and selection on media containing ampicillin and chloramphenicol. CS proteins were prepared from cells grown in CFA media without bile salts and samples were analysed by SDS-PAGE on 14% Tris-Gly gels (Novex) stained with Simply Blue Safe Stain (Invitrogen). Expression of CS4, CS5 and CS6 that was not dependent on the presence of bile salts, was observed (FIG. 2E). However, the amount of CS5 in the cells had a deleterious effect on the level of CS4 in the cell compared with induction by bile salts in the absence of rns (as seen in FIGS. 2C and 2D). Using a low copy number plasmid for expression of rns may have reduced this effect. Thus, regulation of the CS proteins in the vaccine strains could be altered by introduction of different regulator proteins.

1.2.2 Chromosomal Expression

CS4 and CS2 operons are normally found on the chromosome in wild-type strains and the other CS operons are located on low copy number plasmids. To overcome plasmid stability problems and to create a strain suitable for use as a vaccine, it was desirable to insert the CS4 operon into the chromosome of ACAM2006. This would also result in the operon being present at a similar copy number to that seen in wild-type strains and it was hoped that this would prevent 'over-loading' with the additional CS protein. Excessive CS4 protein expression could cause attenuation of the strain and/or interfere with expression of the endogenous CS proteins.

1.2.2.1 Construction of Targeting Vector

Figure 3A:
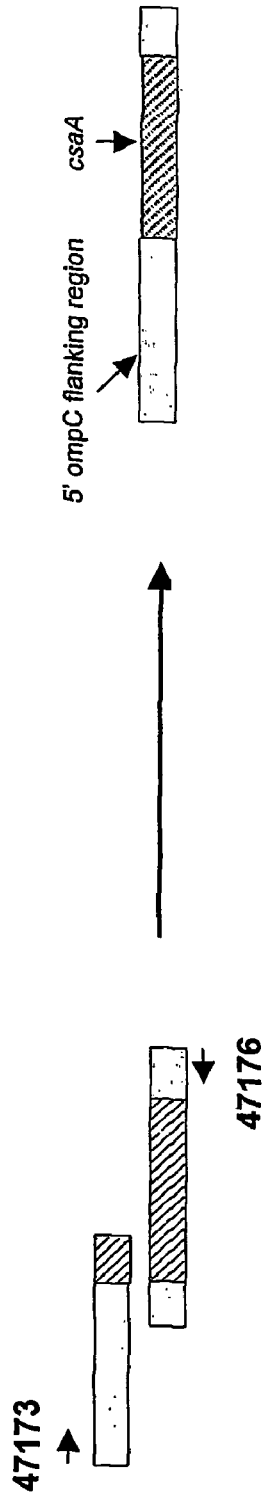
FIG. 3A Stages 1 to 5 in the construction of pJCB12-ompC-CS4-ompC, and features of the primers used.
Figure 3A:
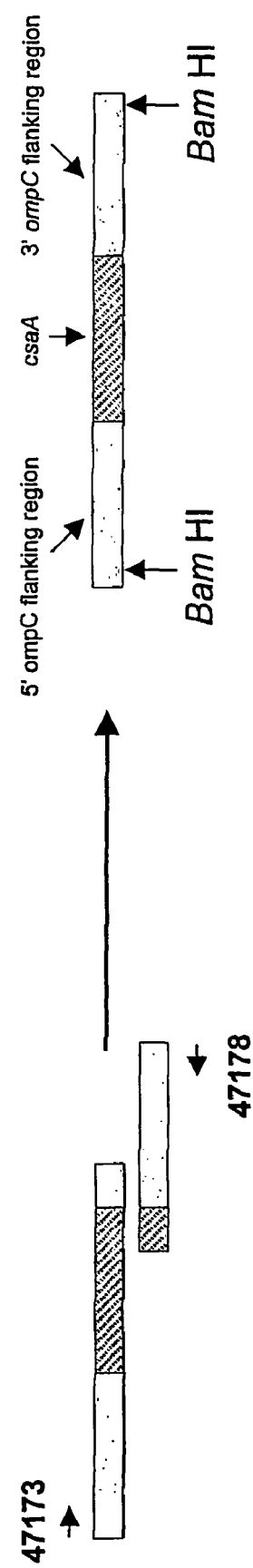
Figure 12:
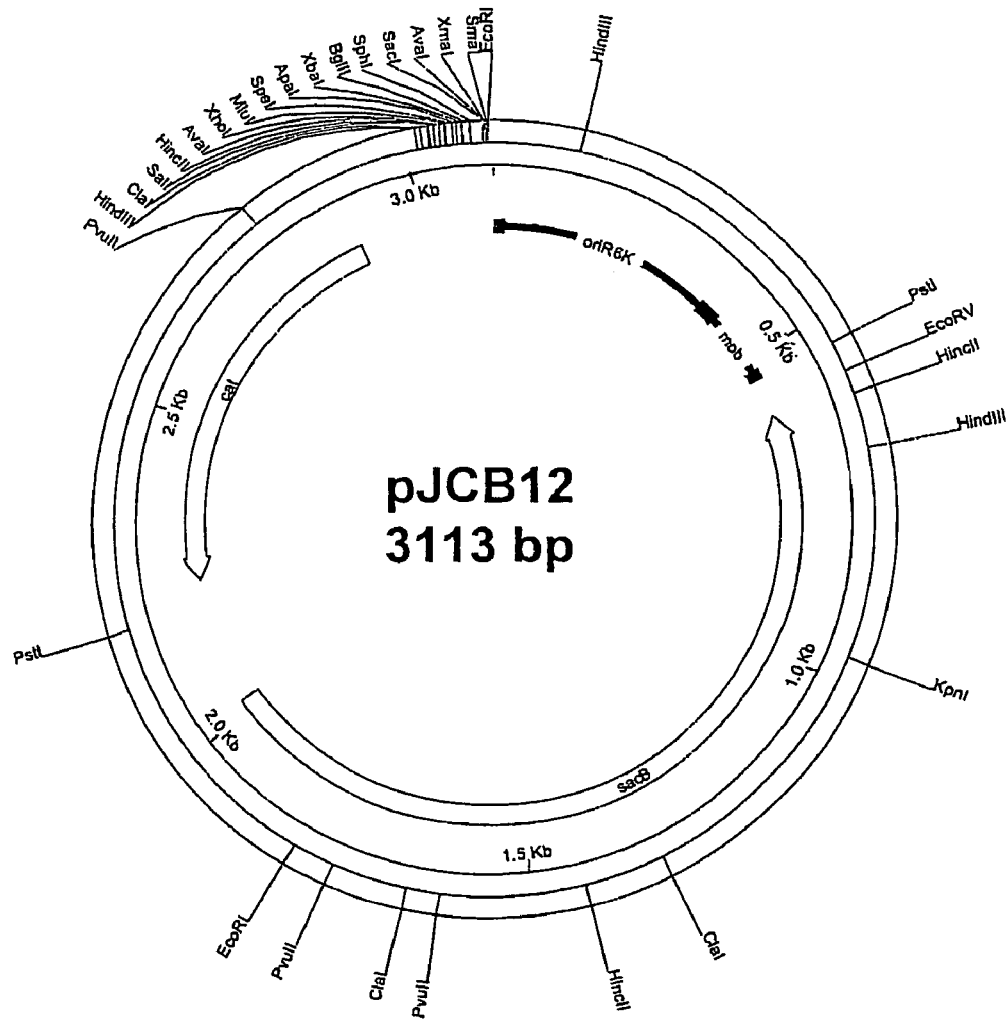
FIG. 12 Map of suicide vector plasmid pJCB12.

The cloning strategy for chromosomal insertion is described in detail in FIG. 3. The suicide vector pJCB12 (FIG. 12) was used for introducing the operon into the chromosome. This plasmid contains the R6K origin and can only be propagated in strains containing λpir (21). In this case pJCB12 and its derivatives were propagated in *E. coli* strain DH5λpir. It was decided to insert the operon into the ompC locus of ACAM2006. Since the ompC gene itself had already been deleted from this strain, its 5' and 3' flanking regions were used to target the CS4 operon into the correct site.

The first stage of the cloning strategy involved individually amplifying the 5' and 3' ompC flanking regions and the csaA gene by PCR (Stage 1, FIG. 3A). Primers 47173 and 47174 were used to amplify the upstream flanking region of the ompC gene and primers 47177 and 47178 were used to amplify the downstream region of the ompC gene. ACAM2006 chromosomal DNA was used as the template. A 721bp fragment including the 5' region of the CS4 operon, up to and including the BglII site in the csaA gene was amplified, using primers 47175 and 47176 and WS-2252A chromosomal DNA as template. Primers 47174 and 47175 contained extended sequences such that the 3' sequence of the upstream-ompC flanking region PCR product and the 5' end of the csaA PCR product contained complementary sequences. This allowed the two fragments to be joined together by overlap extension PCR using primers 47173 and 47176 (Stage 2, FIG. 3A). Similarly, primers 47176 and 47177 contained extended sequences such that the 3' sequence of the csaA PCR product and the 5' sequence of the downstream-ompC flanking region PCR product contained complementary sequences. This allowed the ompC-csaA fragment to be fused to the downstream-ompC flanking region by overlap extension PCR using primers 47173 and 47178 (Stage 3, FIG. 3A).

The ompC-csaA-ompC fragment contained BamHI sites at the 5' and 3' ends, introduced by the primers 47173 and 47178. These sites were used to clone the ompC-csaA-ompC fragment into the BglII site of pJCB12, destroying both the BamHI and BglII recognition sequences (Stage 4, FIG. 3A). This plasmid was called pJCB12-ompC-csaA-ompC. This meant that the BglII site in the csaA gene was now unique and could be used for cloning the remainder of the CS4 operon. Therefore, the remaining 3' region of the CS4 operon was excised from pACYC-CS4 by digestion with BglII and inserted into the BglII restriction site inside the csaA gene (Stage 5, FIG. 3A). Recombinant plasmids with the csaBCE fragment in the correct orientation were identified by PCR screening using oligos 47105 and RGK01. This completed construction of the suicide vector for targeting the CS4 operon into the ompC locus and the plasmid was designated pJCB12-ompC-CS4-ompC.

1.2.2.2 Insertion of the CS4 Operon into the Chromosome pJCB12-ompC-CS4-ompC was used to transform the conjugation-competent, tetracycline sensitive *E. coli* strain SM10λpir (23). ACAM2006 was made tetracycline-resistant by transformation with plasmid pACYC184 (5). Strain SM10λpir-pJCB12-ompC-CS4-ompC was conjugated with ACAM2006-TetR by cross-streaking on LB agar plates. A 2 cm square area was densely streaked with one strain and then over-streaked with the other strain in a perpendicular direction. After overnight growth at 37° C. the cells were scraped off and spread onto agar plates containing chloramphenicol and tetracycline. Transconjugants in which pJCB12-ompC-CS4-ompC had been inserted into the chromosome of ACAM2006-TetR formed colonies, whereas neither of the parent strains were able to grow on this combination of antibiotics. Homologous recombination of the CS4 operon into the correct site (ie the ompC locus) was confirmed by PCR using oligos 4732 and 47105.

Having targeted the CS4 operon into the ompC locus it was necessary to select clones where the vector sequences had been excised, but the CS4 operon had remained in the chromosome. pJCB12 contains the sucrase gene which confers toxicity to cells grown on sucrose, hence correctly targeted transconjugants were grown in medium containing 5% sucrose to select for loss of the suicide vector. Only strains in which the suicide vector had been excised were able to grow. Excision of the vector sequence would mean that the chloramphenicol resistance gene was also lost, therefore sucrose-resistant colonies were further screened to check that they were sensitive to chloramphenicol. Chloramphenicol-sensitive, sucrose-resistant colonies were screened by PCR to identify clones in which the CS4 operon had been retained in the ompC locus (primers 4732 and 47105). A strain in which the CS4 operon was correctly inserted was selected and designated ACAM2006-CS4.

1.2.2.3 Expression of CS4 from the Chromosomal Locus

Figure 4:
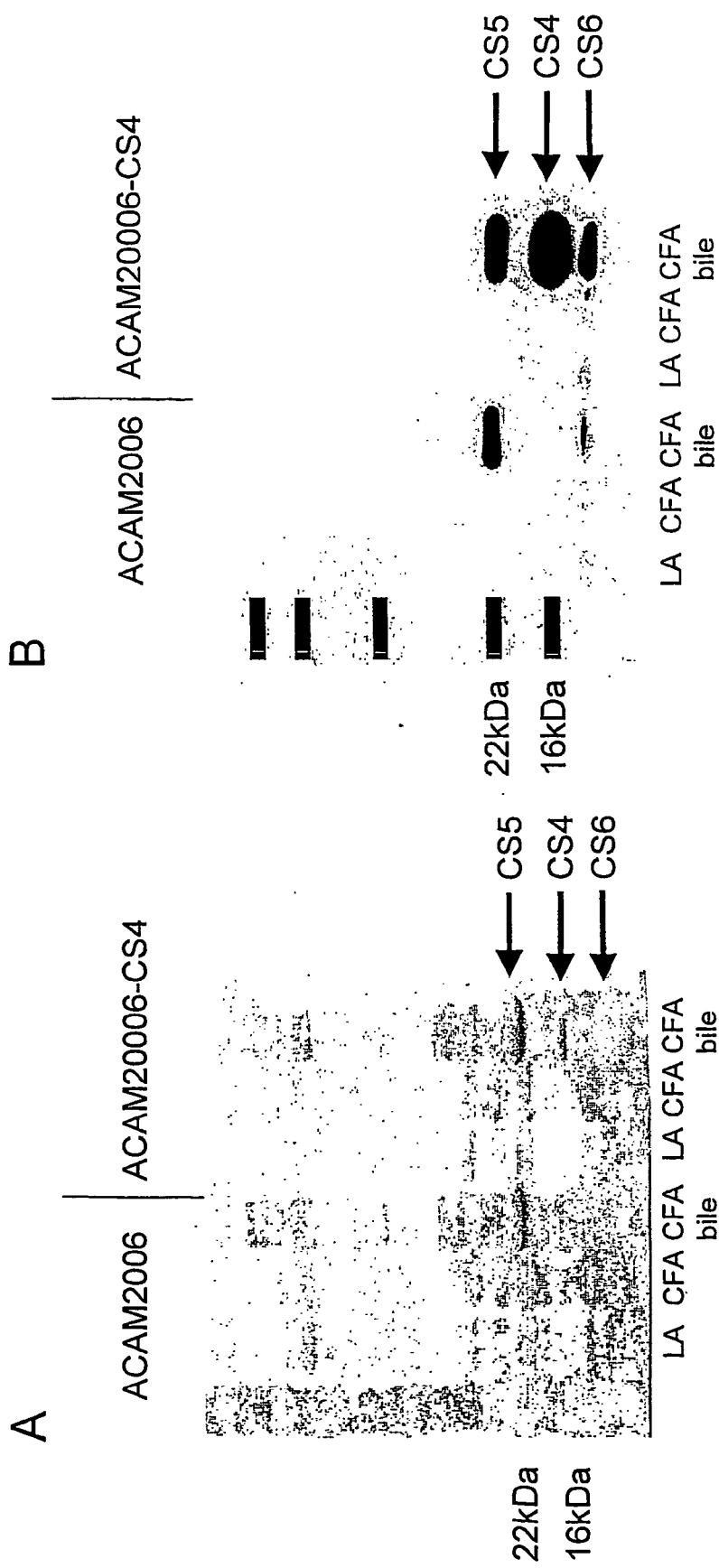
FIG. 4 SDS-PAGE analysis of CS antigen expression in strains ACAM2006 and ACAM2006-CS4 showing the effects of bile salts.
(A) Staining is with Simply Blue Safe Stain (Invitrogen)
(B) Western Blot.

ACAM2006-CS4 was grown overnight on plates containing LB agar, CFA agar or CFA agar plus 0.15% bile salts. CS proteins were prepared by heat-extraction as described in the "Materials and Methods". Similar preparations were made from ACAM2006 for comparison. Samples were analysed by SDS-PAGE on 14% Tris-Gly polyacrylamide gels (Novex) Bands were visualised by staining with SimplyBlue SafeStain (Invitrogen) or by Western Blot (FIGS. 4A & B). Blots were stained with rabbit CS4, CS5 and CS6-specific antibodies and an anti-rabbit HRP conjugate (Sigma A4914) as described in the "Materials and Methods".

Low levels of CS6 were detected from ACAM2006 and ACAM2006-CS4 when the stains were grown either with or without bile salts, although slightly higher levels were detected when bile salts were present. CS5 was detected in both stains but only when bile salts were included in the agar. CS4 was present only in ACAM2006-CS4 and only in the presence of bile salts.

Thus a strain has been created in which CS4, CS5 and CS6 are all expressed at good levels. As seen with plasmid pACYC-CS4, control of CS4 expression has shifted to become bile-salt dependent, similar to that seen naturally for CS5 expression. This type of regulation should work well in a vaccine strain where CS proteins are induced in vivo. It may be possible, however, to change the pattern of regulation by introduction of a different regulator such as rns or cfaD (Section 1.2.1).

ACAM2006 and ACAM2006-CS4 carry a P2-like bacteriophage genome in the chromosome (Section 1.2.1). A large part of that genome was deleted from both strains to improve their suitability as components of a vaccine. This deletion did not affect expression of CS4, CS5 or CS6. The bacteriophage-deleted ACAM2006 strain is ACAM2012 (deposited strain with accession number 020282968). Strain ACAM2012-CS4 (ACAM2013) has been deposited with accession number 02082969, as described above.

Example 2

Production of a CS1, CS2, CS3 Strain (CS1 Expressed in a CS2/CS3 Strain)

2.1 Cloning of the CS1 Operon

Figure 5B:
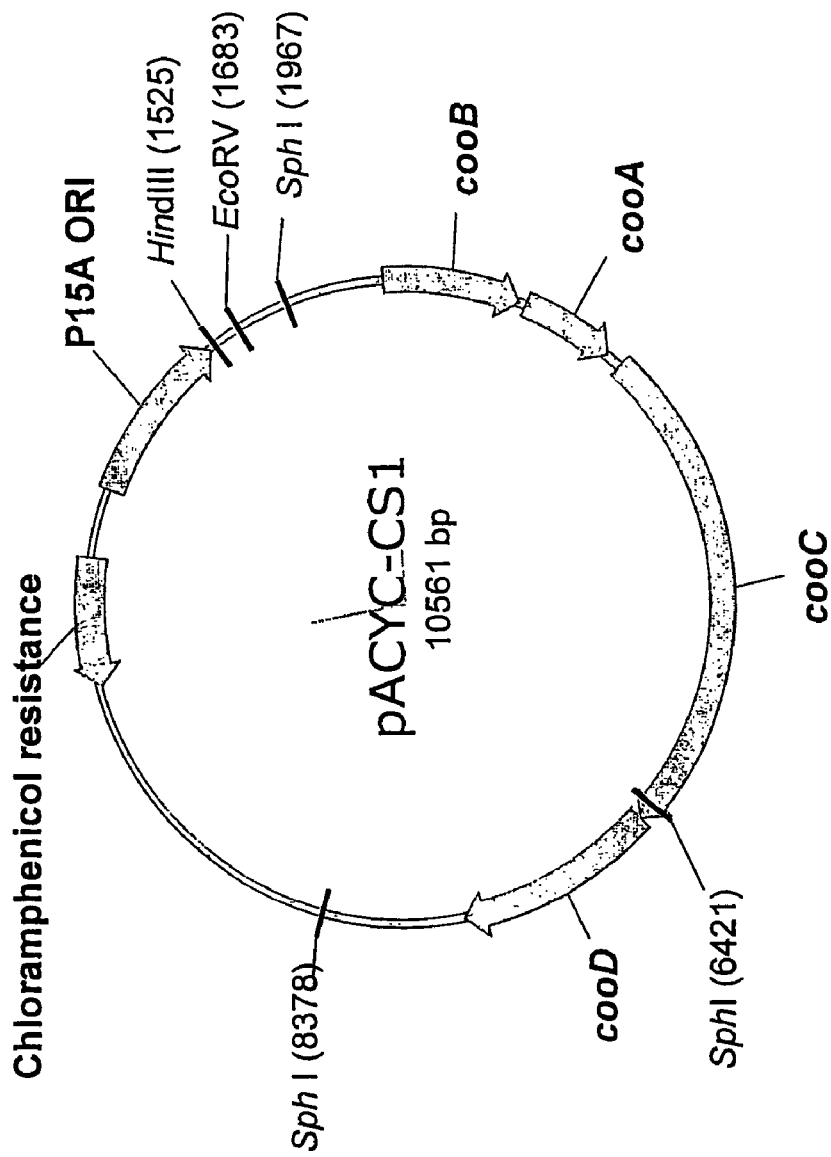
FIG. 5B Map of plasmid pACYC-CS1.

The genes of the CS1 operon of ETEC have been sequenced (Genbank Accession Numbers M58550, X62495, X76908). These sequences were compiled into the complete operon (cooB, cooA, cooC, cooD) and the restriction sites were analysed using the VectorNTi program Version 7 (Informax) (FIG. 5A). Two sites suitable for cloning the intact operon by restriction digestion were identified: EcoRV upstream of cooB, and BglII downstream of cooD. Plasmid DNA purified from the CS1/CS3 strain E1392/75-2A (Table 1) was digested with EcoRV and BglII and subjected to agarose gel electrophoresis. DNA fragments of approximately 6.6 kb were isolated from the gel using a QIAquick gel extraction kit. This was the correct size for the CS1 operon as predicted from the compiled Genbank sequences. The 6.6 kb fragments were ligated into the cloning vector pACYC184 ((5); Supplied by NEB, FIG. 1B) that had been digested with EcoRV and BamHI. Ligated colonies were used to transform E. coli K12 and colonies were selected on agar plates containing chloramphenicol. Correct constructs were identified by digestion with HindIII or HindIII/SphI. This construct was designated pACYC-CS1 (FIG. 5B).

2.2 Plasmid Expression

Figure 6:
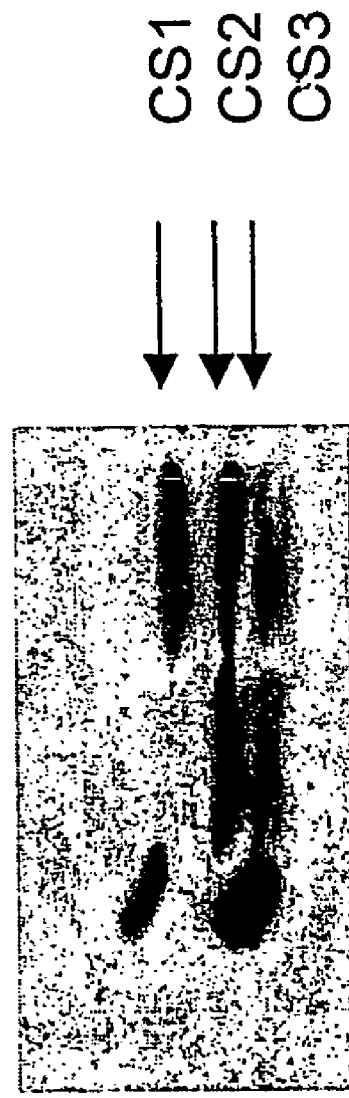
FIG. 6 SDS-PAGE analysis of CS antigen expression in strains PTL003, ACAM2007 and ACAM2007-pCS1, using Western Blotting.

Strain ACAM2007, an attenuated CS2/CS3 strain, was transformed with pACYC-CS1 by electroporation. This strain was designated ACAM2007-pCS1. Stains PTL003 (CS1/CS3), ACAM2007 and ACAM2007-pCS1 were spread onto CFA-agar plates and CFA proteins were prepared by heat-extraction as described in the "Materials and Methods". Samples were analysed by electrophoresis on 14% Tris-Gly polyacrylamide gels. In order to resolve the CS2 and CS3 proteins, which are approx 15.3 and 15.1 kDa respectively, 14 cm gels were utilised. CS proteins were detected by Western Blot, (FIG. 6) stained with rabbit CFA/II-specific antibodies (which recognise CS1, CS2 and CS3) and developed as described in the "Materials and Methods".

CS1 and CS3 were detected in PTL003, CS2 and CS3 were detected in ACAM2007 and CS1, CS2 and CS3 were detected in ACAM2007-pCS1. Therefore we had demonstrated that it is possible to express three CFA/II antigens in a single strain.

2.3 Chromosomal Insertion

A CS2/CS3 strain expressing CS1 may form a component of an ETEC vaccine even when the CS1 operon is carried on a stable plasmid, however for increased strain stability it would be desirable to insert the CS1 operon into the chromosome of the strain. A similar strategy to that described in Section 1.2.2 for the CS4/CS5/CS6 strain, or other technique known in the art, could be employed.

Example 3

Production of a CS4, CS5, CS6 Strain (CS5 Expressed in a CS4/CS6 Strain)

3.1 Cloning of the CS5 Operon

Figure 7B:
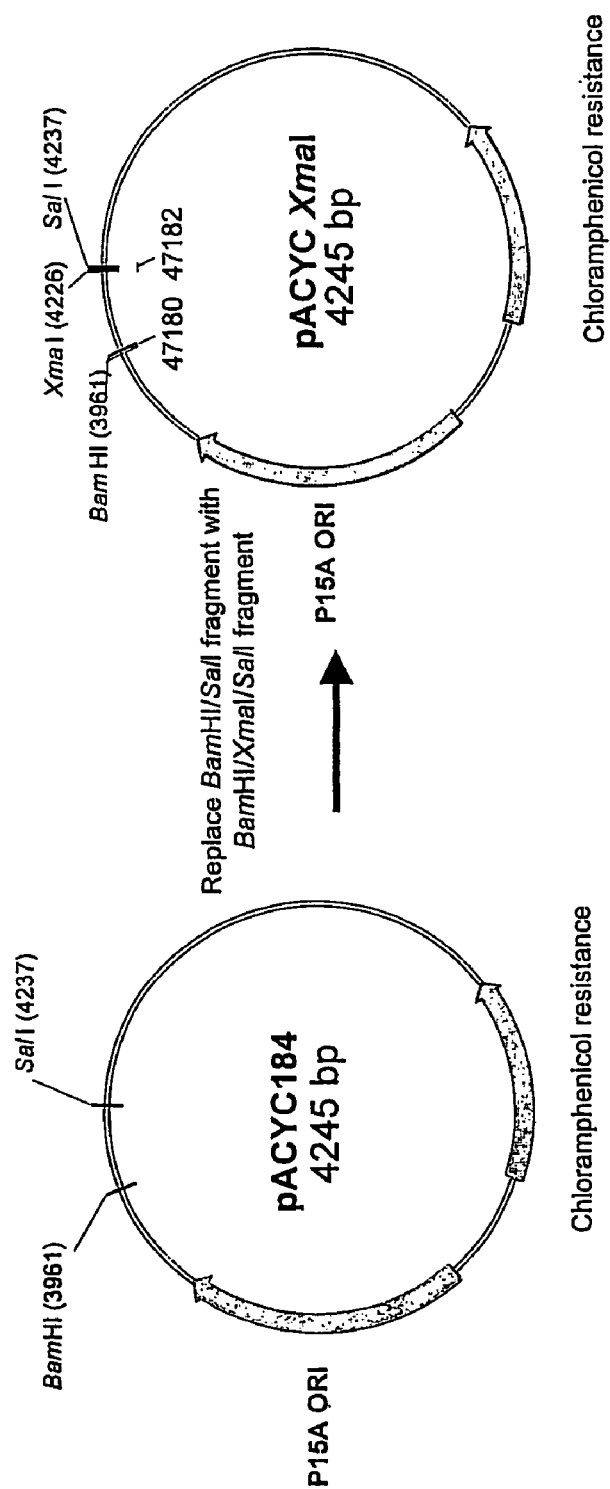
FIG. 7B Construction of plasmid pACYC-XmaI.

The sequence of the CS5 operon has been published (Genbank AJ224079). Computer aided restriction analysis of this sequence (using Vector NTi Version 7, Informax) revealed an AgeI site upstream of the first gene of the operon (csfA) and an XmaI site downstream of the last gene in the operon (csfD) (FIG. 7A). These sites were suitable for cloning the intact operon by restriction digestion, avoiding any PCR-related errors. The 'overhang' generated by digestion with AgeI is complementary to the XmaI overhang, hence the fragment could be cloned directly into XmaI-cut vector. However the vector pACYC184 did not contain an XmaI site and so required some modification (FIG. 7B). Approximately 276 bp of pACYC 184 from the unique BamHI site at position 3961 to the unique SalI site at position 4237 were amplified using Primer 47180 and Primer 47182. Both the BamHI and SalI sites were preserved, and Primer 47182 also introduced a new XmaI site 5' of the SalI site. The 295 bp PCR-amplified DNA fragment was digested with SalI and BamHI and was cloned into pACYC184 that had also been digested with SalI and BamHI, thus introducing a new and unique XmaI site into the vector. This vector was named pACYC-XmaI (FIG. 7B).

Figure 7C:
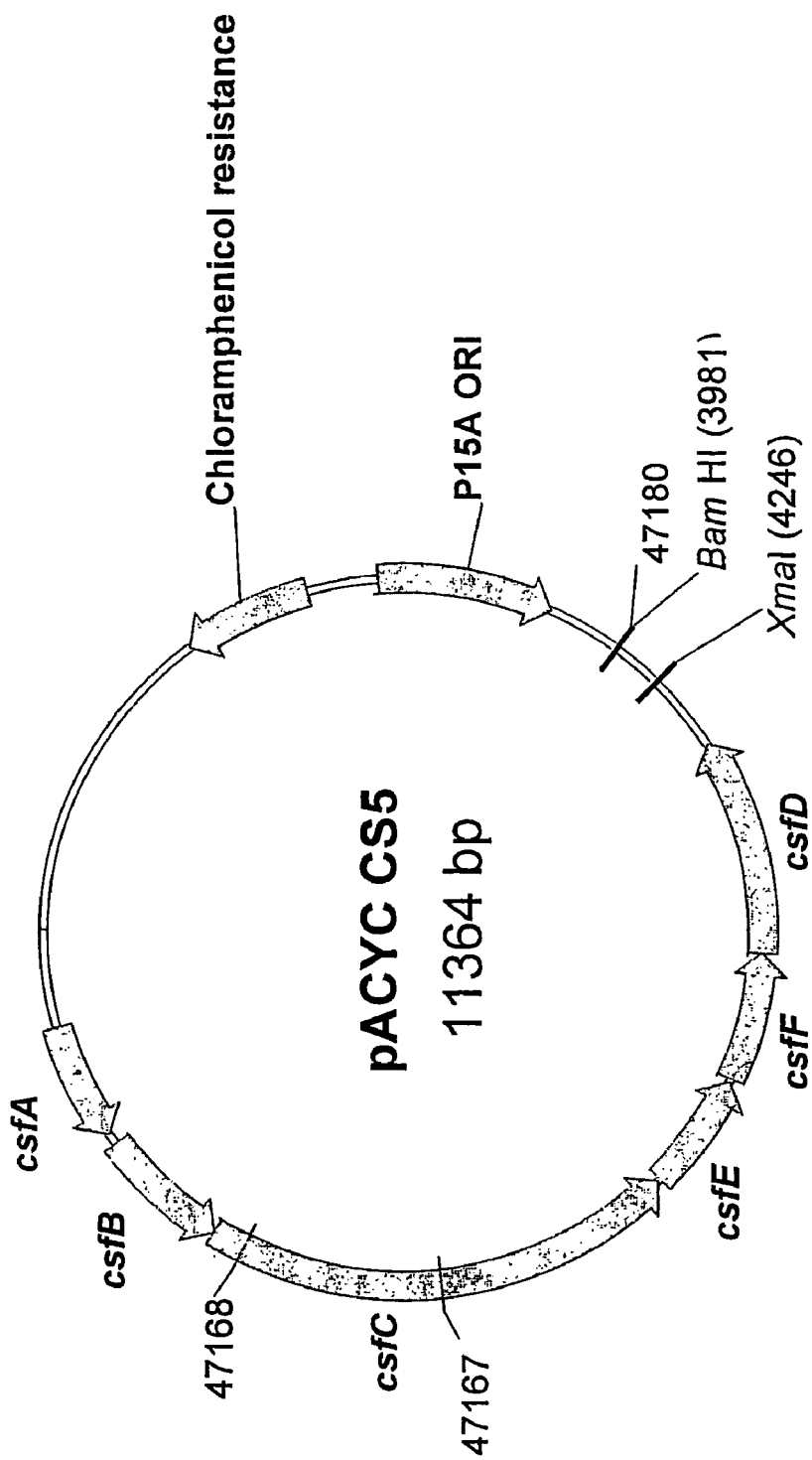
FIG. 7C Structure of plasmid pACYC-CS5.
Figure 8A:
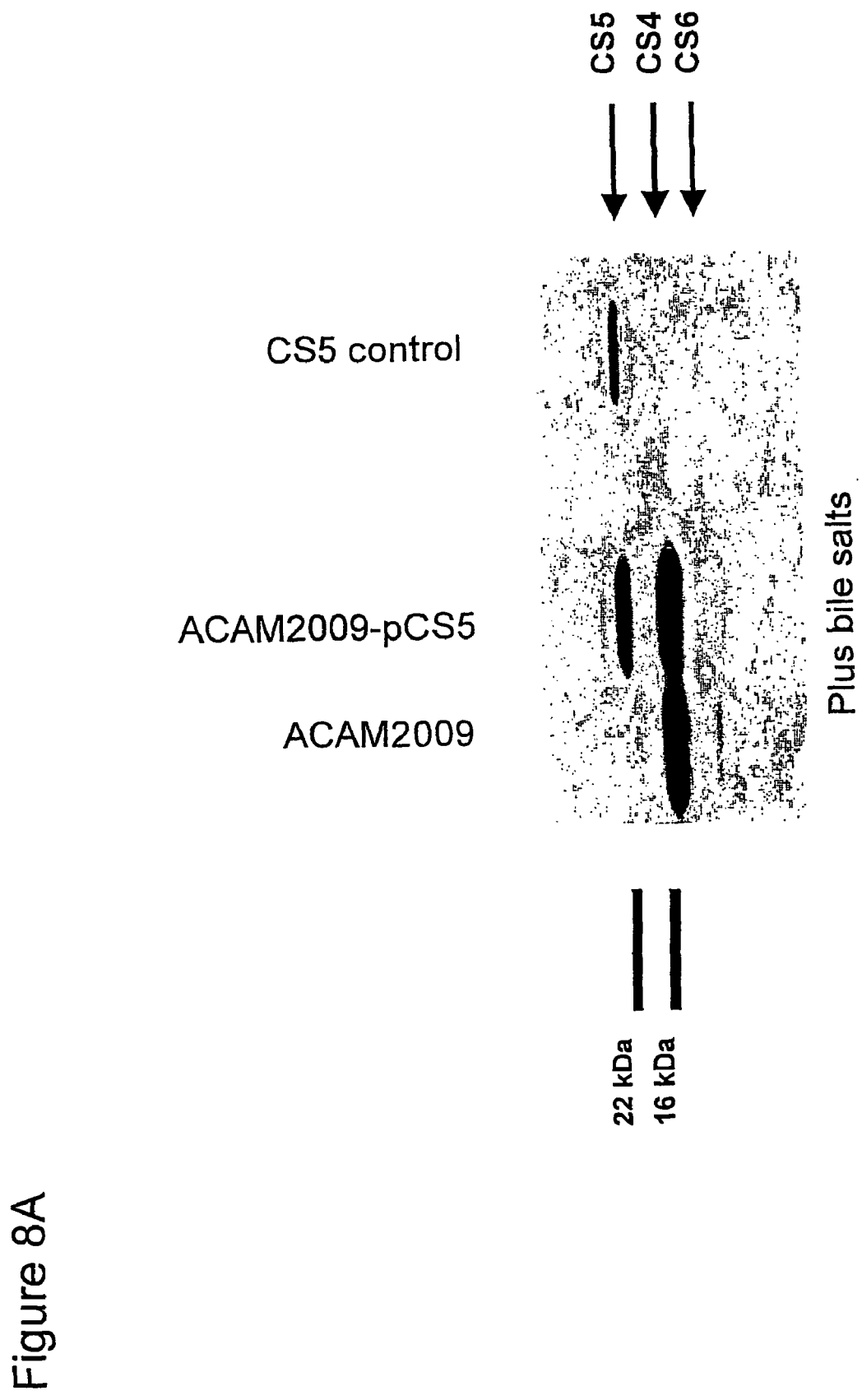
FIG. 8A SDS PAGE analysis of CS antigen expression in the presence of bile salts in strains ACAM2009 and ACAM2009-pCS5, using Western Blotting.
Figure 8B:
FIG. 8B SDS PAGE analysis of the effect of bile salts on CS antigen expression in strains ACAM2006, ACAM2009 and ACAM2009-pCS5, using Western Blotting.
Figure 9:
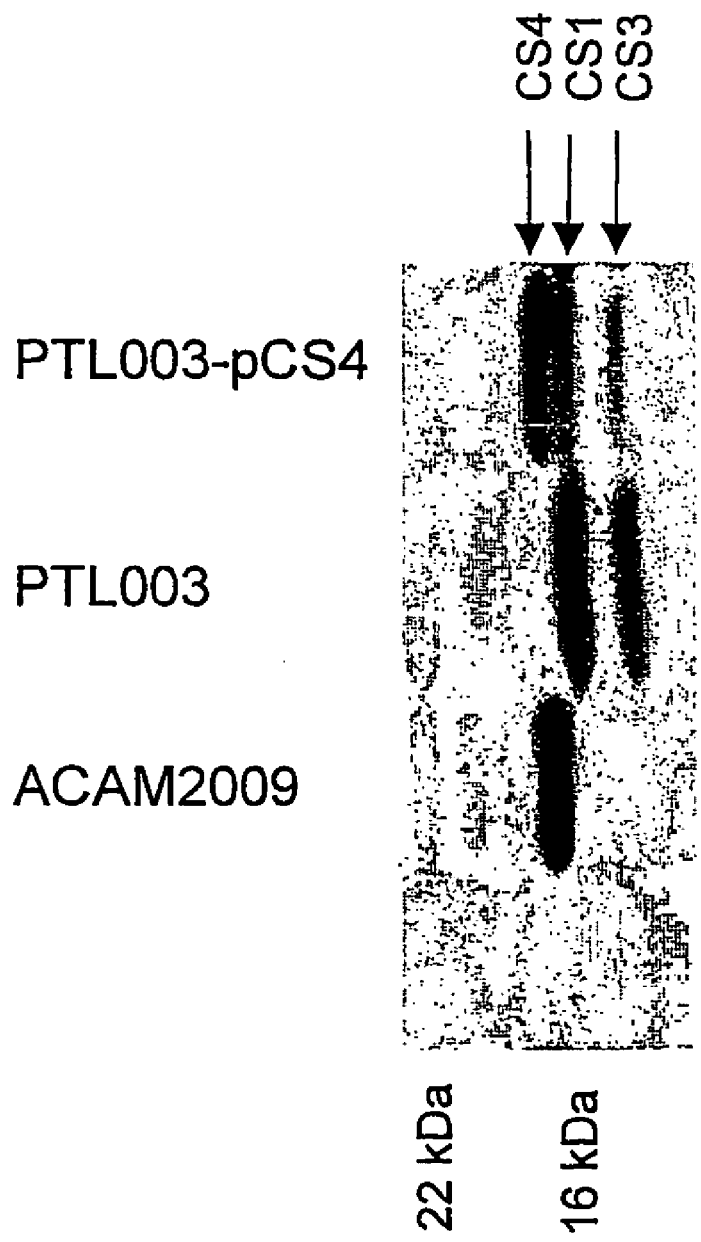
FIG. 9 SDS PAGE analysis of CS antigen expression in strains ACAM2009, PTL003 and PTL003-pCS4. Staining is with Simply Blue Safe Stain (Invitrogen).
Figure 11:
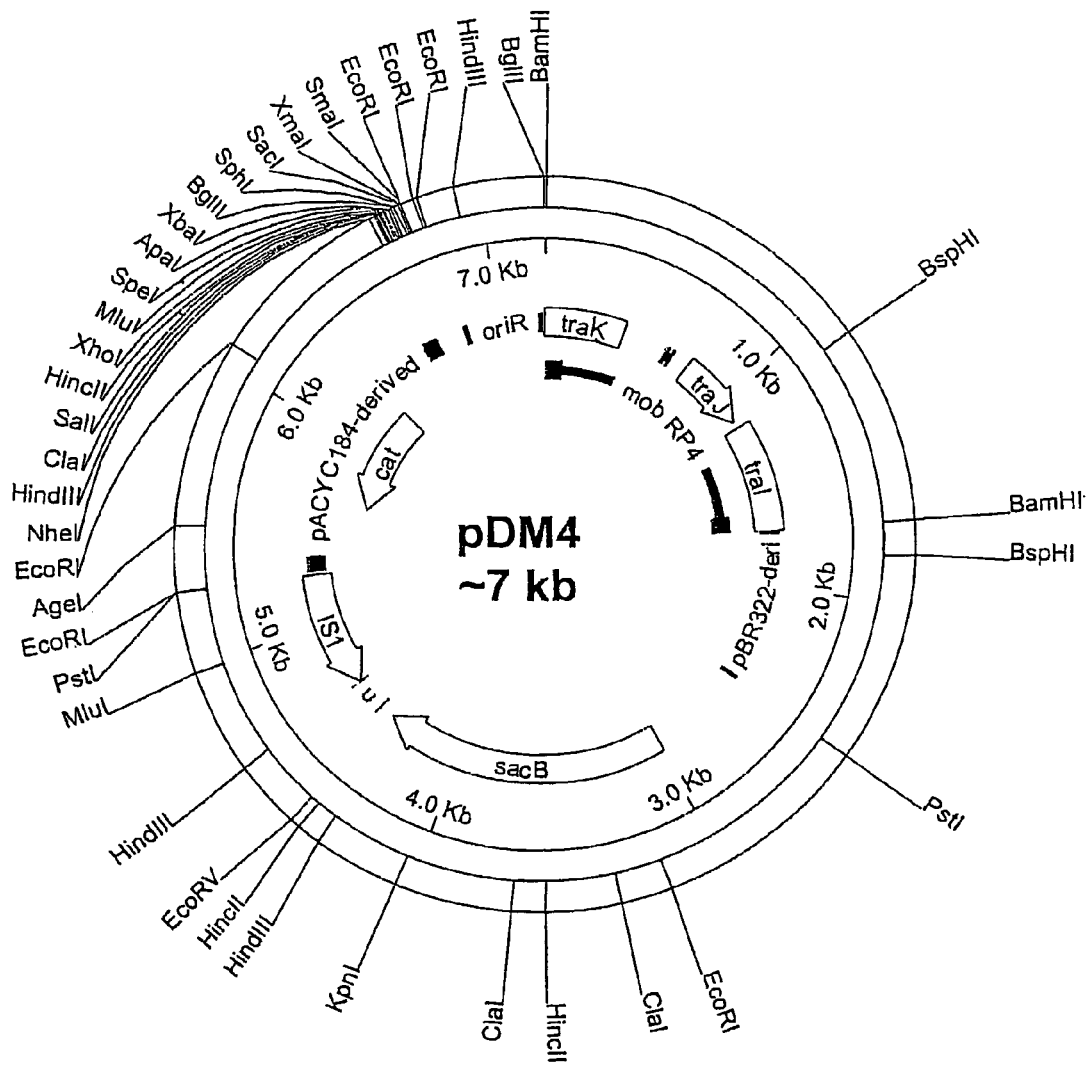
FIG. 11 Map of suicide vector plasmid pDM4. u=unknown sequence, unknown length.

Plasmid DNA was isolated from Strain WS2773-E (CS5/CS6) and a portion was digested with AgeI and XmaI and subjected to agarose gel electrophoresis. DNA fragments of approximately 7 kb were isolated from the gel using a QIAquick gel extraction kit (QIAgen) and were ligated into pACYC-XmaI that had also been digested with XmaI and treated with Calf Intestine Alkaline Phosphatase. Ligation mixture was used to transform *E. coli* XL10 Gold KanR and colonies were selected on agar plates containing chloramphenicol. Colonies were screened for plasmids containing the CS5 operon by PCR with Primers 47168 and 47167. The orientation was determined using primers 47180 and 47168. A correct plasmid was designated pACYC-CS5 (FIG. 7C).

3.2 Plasmid Expression

Strain ACAM2009, an attenuated CS4/CS6 strain, was transformed with pACYC-CS5 by electroporation and the strain was designated ACAM2009-pCS5.

Strains ACAM2009 and ACAM2009-pCS5 were spread onto CFA-agar plates containing 0.15% bile salts and CFA proteins were purified as described in the "Materials and Methods". Samples were analysed by SDS PAGE on 14% Tris-Gly gels (Novex) and bands were visualised by Western Blot (FIG. 8A). Blots were stained with rabbit CFA/IV-specific antibodies that detect CS4, CS5 and CS6 and anti-rabbit HRP conjugate (Sigma A4914). All three CS proteins (CS4, CS5 and CS6) were detected in Strain ACAM2009-pCS5 in the presence of bile salts. To determine whether bile salts were necessary for CS5 expression (as in natural CS5/CS6 strains) ACAM2006, ACAM2009 and ACAM2009-pCS5 were spread onto agar plates with or without bile salts and CFA proteins were purified as described in the "Materials and Methods". Samples were analysed by SDS-PAGE followed by Western blotting using CFA/IV-specific antibodies (FIG. 8B). As expected, in ACAM2006 CS5 was expressed only when bile salts were present in the media, whereas in ACAM2009 CS4 was present both with and without bile salts in the media. In ACAM2009-pCS5 both CS4 and CS5 were present independently of the presence of bile salts in the CFA agar. Presumably the cfaD regulator that is present in ACAM2009 and controls expression of CS4 in a bile-salt independent manner is also able to regulate expression of CS5.

3.3 Chromosomal Insertion

A CS4/CS6 strain expressing CS5 may form a component of an ETEC vaccine even when the CS5 operon is carried on a stable plasmid, however for increased strain stability it would be desirable to insert the CS5 operon into the chromosome of the strain. A similar strategy to that described in Section 1.2.2 or other technique known in the art could be employed.

Example 4

Other Strain Combinations

We wished to know if expression of CS proteins in the strains is restricted by CFA-type, for example would it be possible to express CFA/II proteins within a CFA/IV strain? To investigate this, plasmids carrying cloned CS operons were used to transform ETEC strains of different CFA types.

4.1 CFA/II and CFA/IV Co-Expression pACYC-CS4 (Section 1.1) was used to transform PTL003 (an attenuated CS1/CS3 strain, Table 1) to create PTL003-pCS4. PTL003, PTL003-pCS4 and ACAM2009 (an attenuated CS4/CS6 strain) were spread onto CFA-agar plates and CS proteins were purified as described in the "Materials and Methods". Samples were analysed by electrophoresis on 14% Tris-Gly gels (Novex) and bands were visualised by staining with SimplyBlue SafeStain (Invitrogen) (FIG. 9). CS1 and CS3 were detected in PTL003 and CS4 was detected in ACAM2009. In PTL003-pCS4 CS1, CS3 and CS4 were present. This indicated that it is possible to express CFA/II and CFA/IV antigens in a single strain.

4.2 Reference Example: CFA/I and CFA/IV Co-Expression

In order to test if multiple expression of CS proteins in a single strain is restricted by CFA type, pACYC-CS4 (Section 1.1) was used to transform strain ACAM2010 (an attenuated CFA/I strain) to create ACAM2010-pCS4. ACAM2010, ACAM2010-pCS4 and WS-2252A (CS4/CS6) were spread onto CFA-agar plates and CFA proteins were purified as described in the "Materials and Methods". Samples were analysed by electrophoresis on 14% Tris-Gly gels (Novex) and bands were visualised by staining with SimplyBlue SafeStain (Invitrogen) or by Western Blot using CS4 and CFA/I-specific rabbit antibodies (FIG. 10). CFA/I was detected in ACAM2010 and CS4 was detected in WS-2252A. In strain ACAM2010-pCS4 both CFA/I and CS4 were present. This indicated that it is possible to express to different types of CFA antigen in a single strain.

Example 5

Introduction of Multiple Genetic Mutations into Bacterial Vaccine Strains

This section describes the generation of a novel suicide vector plasmid, pJCB12, and its use for the introduction of mutations into chromosomal or plasmid encoded gene loci. Production and use of pJCB12 is described in UK Patent Application 0121998.9 and in the International patent application claiming priority from UK Patent Application 0121998.9, and filed by Acambis Research Limited on the same day as the present International application. The contents of that International application are incorporated by reference.

Suicide vector plasmids such as pDM4 (24), pJCB12, pCVD442 (12) and others can be used to introduce defined genetic constructs into specific targets in the bacterial genome. Plasmid pJCB12 is a new, optimised suicide vector based on the previously constructed suicide vector pDM4. The defined genetic construct to be introduced into the bacterial genome may be a deletion mutation of a specific gene, or a more complex structure such as, for example, an insertion of a gene within another and expressed from a chosen promoter from within the construct. Generally, the extremities of the constructs will consist of nucleotide sequences derived from the region of the genome to be targeted.

Suicide vectors pDM4 and pJCB12 possess a number of key components (see FIGS. 11 and 12):

An origin of replication which directs replication of the vector in some strains of bacteria but not in others, oriR6K. oriR6K is the origin of replication derived from the naturally occurring plasmid R6K. This origin requires the R6K pir gene for replication, which is absent from the suicide vectors. Three laboratory *E. coli* strains are available that carry the pir gene on their chromosome, which are SY327λpir, SM10λpir, and DH5αλpir. All three of these strains may be used to propagate pDM4, pJCB12 and their derivatives.

A transfer origin that directs conjugative transfer of the vector from one bacterial strain to another, mobRP4. mobRP4 is the transfer origin from the naturally occurring plasmid RP4. This allows the conjugative transfer of pDM4 and pJCB12 and their derivatives to recipient bacterial strains. In order to function, mobRP4 requires the genes encoding the RP4 transfer functions to be present in the donor bacterial cell. Laboratory *E. coli* strain SM10λpir carries these genes on its chromosome, and so this strain can be used as a donor strain for pDM4, pJCB12 and their derivatives.

A gene encoding a product that is toxic to bacterial cells when the cells are grown under defined conditions, sacB. sacB codes for levansucrase which produces a product that is toxic to Gram-negative bacteria when grown on sucrose.

A selectable marker, cat. cat codes for chloramphenicol acetyltransferase and confers resistance to the antibacterial chloramphenicol.

A multiple cloning site (MCS), i.e. a site into which defined genetic constructs may be cloned for introduction into a recipient bacterial cell.

Suicide vector pJCB12 is a modified version of pDM4 in which much of the intergenic and non-functional DNA has been removed. Therefore, there is much less opportunity for incorrect targeting using this suicide vector. Whereas pDM4 is approximately 7 kb in size, pJCB12 is only 3 kb but retains all the key components. In particular, the mobRP4 region of pJCB12 is merely 0.15 kb, and the IS1-like nucleotide sequences have been removed from the sacB region. These modifications are particularly advantageous when manipulating ETEC strains which generally harbour many plasmids that could act as undesirable targets of homologous recombination with components of the suicide vector. In addition, the smaller size of pJCB12 allows easier in vitro manipulation and construction of derivatives because smaller DNA molecules ligate together and transform into $E.\ coli$ hosts more efficiently, improving the chances of obtaining derivatives of the correct construction. The smaller size also allows greater efficiency when introducing the constructs into recipient bacteria by transformation rather than by conjugation.

Laboratory $E.\ coli$ strain SM10λpir can be used to transfer pJCB12 and its derivatives to recipient bacterial strains by conjugation because it has the tra functions from plasmid RP4 inserted into its chromosome. However, strain SM10λpir shows relatively low transformation frequencies. For this reason, strain DH5αλpir would normally be used for the construction of pJCB12 derivatives, and once derivatives of the correct construction have been identified these would be transferred to SM10λpir for introduction to recipient strains by conjugation.

Construction of Suicide Vector pJCB12

Figure 13:
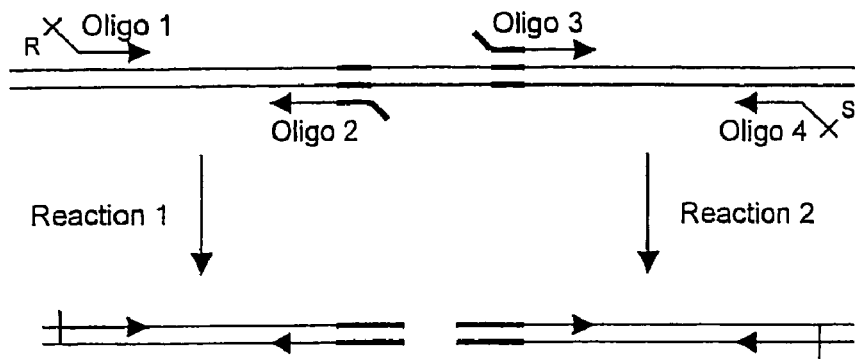
FIG. 13 Diagram of method used to create specific gene deletion constructs by overlap extension PCR. Step 1=PCR amplification of two DNA fragments. Step 2=overlap extension PCR using DNA products from reaction 1 and reaction 2 of step 1 and amplification of the overlap PCR product. R and S stand for restriction enzyme sites.
Figure 13:
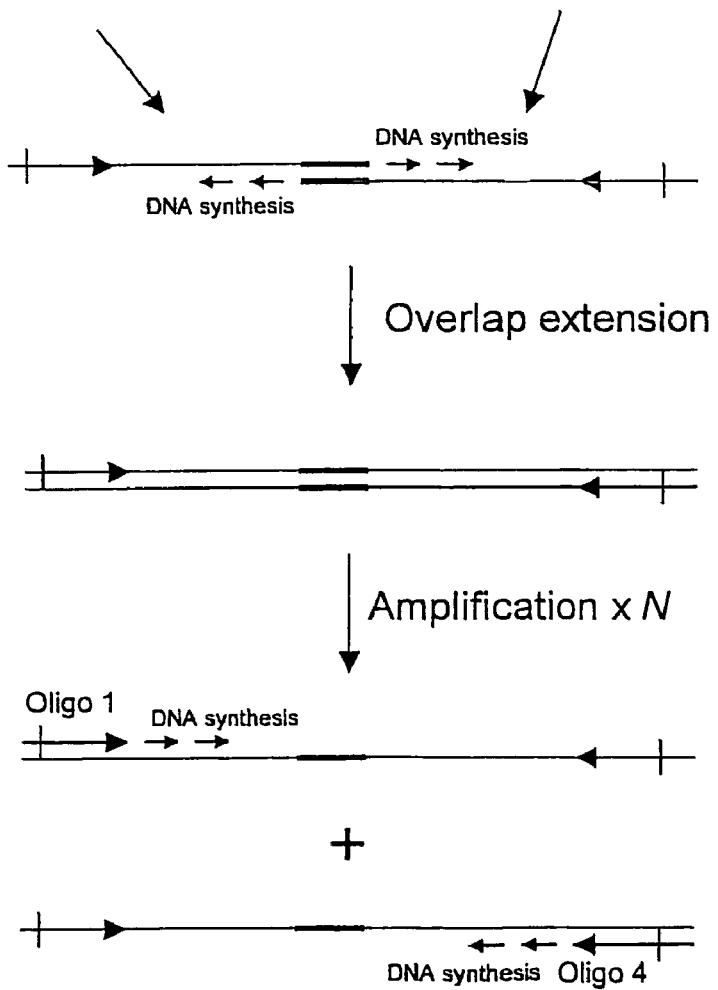

Suicide vector pJCB12 was constructed by several rounds of overlap extension PCR (30, FIG. 13) using pDM4 plasmid DNA as template. Initially, four fragments were amplified from pDM4 by PCR using the high fidelity DNA polymerase, Pfu Turbo™. These were the oriR6K fragment, amplified using oligonucleotides 4714 and 4715; the mobRP4 fragment amplified using oligonucleotides 4716 and 4717; and the cat gene that was amplified in two parts using oligonucleotides 4718 with 4719 and 4720 with 4721. This was done in order to remove an EcoRI restriction enzyme site within the cat gene. The oriR6K fragment and the mobRP4 were then joined in an overlap extension PCR reaction using oligonucleotides 4714 and 4717. Likewise, the cat fragments were joined using oligonucleotides 4718 and 4721. These two resulting fragments were then joined in a final overlap extension PCR reaction using oligonucleotides 4717 and 4718. The resulting PCR product was ligated and transformed into SY327λpir cells and transformants were selected on L-agar supplemented with chloramphenicol at 20 mg/ml. Transformants harbouring plasmids of the correct size were obtained and one of these, called pDM4A7, was chosen for further manipulation.

At this stage, clearly the oriR6K and cat components of the plasmid pDM4A7 are functional. However, in order to confirm that the mobRP4 locus was functional plasmid pDM4A7 was transformed into strain SM10λpir. These transformants were picked onto L-agar supplemented with chloramphenicol at 15 mg/ml and naladixic acid at 5 mg/ml. This L-agar was cross-streaked with cells of strain SY327λpir. While chloramphenicol selects those bacterial cells which harbour pDM4A7, nalidixic acid selects for SY327λpir. After overnight incubation, many colonies grew where the strains were cross-streaked, but none grew elsewhere on the plate, confirming that pDM4A7 is mobilisable from strain SM10λpir and that the mobRP4 locus is functional.

Plasmid pDM4A7 was then digested with EcoRI, treated with Pfu Turbo™ DNA polymerase and ligated in order to remove the EcoRI restriction enzyme site to generate plasmid pDM4A7DEcoRI. A short HindIII fragment from pDM4 which includes the multiple cloning site was then ligated into pDM4A7DEcoRI digested with HindIII. The ligation reaction was transformed into SY327λpir and transformants selected on L-agar supplemented with 20 mg/ml chloramphenicol.

Oligonucleotide R6K-01 hybridises within the short HindIII fragment from pDM4 which includes the multiple cloning site. Therefore, transformants were screened by PCR using oligonucleotides R6K-01 and 4720 in order to identify those harbouring the desired plasmid construct. A number of such transformants were identified, and one of these, called pDM4A7DE, was chosen for further manipulation.

Plasmid pDM4A7DE carries three EcoRI sites very close together on the short HindIII fragment from pDM4 which includes the multiple cloning site. The two very short EcoRI fragments of pDM4A7DE were therefore removed by digestion with EcoRI followed by ligation. This resulted in a pDM4A7DE derivative that possess only one EcoRI site which was called pJCB10. The region of pJCB10 that includes oriR6K and the MCS was amplified using oligonucleotides 4715 and 4917 and nucleotide sequence determinations for part of this fragment were performed using oligonucleotide 4917. This presented us with the nucleotide sequence across the MCS which was previously unknown.

The sacB gene was then amplified using Pfu DNA polymerase and oligonucleotides 4722 and 4723. The 1.6 kb product was ligated with the plasmid vector pPCR-Script™ (Stratagene) and transformed into $E.\ coli$ XL10 Gold™ cells (Stratagene). Transformants were obtained and the functionality of the sacB gene was confirmed by plating the clones onto L-agar and 5% sucrose agar. One construct gave good growth on L-agar, and none on 5% sucrose agar, and so was chosen as the source of the sacB gene. The sacB gene was then digested from this clone using the restriction enzyme PstI, sites for which were incorporated into oligonucleotides 4722 and 4723 for this purpose, and ligated with pJCB10 also digested with PstI. Colonies were checked by PCR using oligonucleotides 4716 and 4766, yielding a product of the expected size (~1700 bp). Again the functionality of the gene was confirmed by plating the clones onto L-agar and 5% sucrose agar. One construct grew on L-agar, but not on 5% sucrose agar. Sequencing of this construct using oligonucleotides 4716 and 4766 respectively indicated the orientation of the sacB gene. This construct was called pJCB12.

Principle of Use of pJCB12

Once a defined genetic construct has been ligated into pJCB12 to give a pJCB12-derivative, the plasmid is transferred into a recipient strain such as an ETEC strain. This may be done according to methods well known in the art, either by conjugation from the pJCB12 host strain SM10λpir, or by transformation of the purified pJCB12-derivative directly into the recipient strain.

Transconjugants or transformants are selected on bacteriological growth medium supplemented with the antibiotic chloramphenicol. Since the suicide vector pJCB12 is unable to replicate in the absence of the pir gene, any transconjugants or transformants that grow will generally have resulted from fusion of the pJCB12-derivative with another replicon by homologous recombination.

Figure 14:
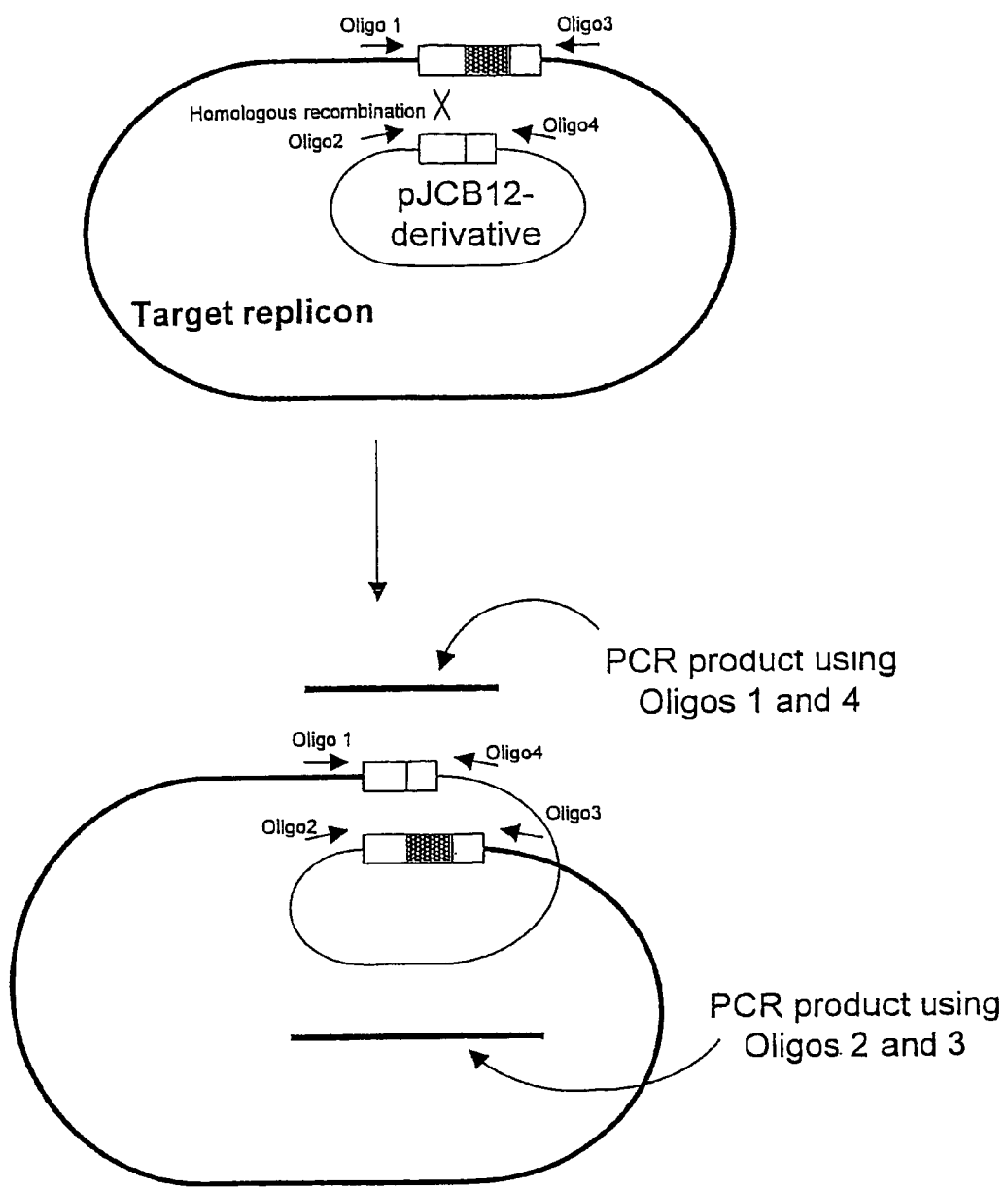
FIG. 14 Diagram of method used to demonstrate correct integration of suicide vector into targeted locus by linkage PCR.

In order to optimise fully the defined mutation process, a novel approach may be taken to screen transformants or transconjugants using PCR to identify those in which the pJCB12-derivative has targeted the desired region of the genome. For this, one oligonucleotide is designed which hybridises within the pJCB12 nucleotide sequences adjacent to the MCS where the defined genetic construct has been inserted. The other oligonucleotide is designed to hybridise to the region of the genome to be targeted, adjacent to but outside of the defined genetic construct. Transformants or transconjugants that are positive using this PCR will have the pJCB12-derivative targeted to the correct region of the genome (see FIG. 14).

Once the correct recombinants have been identified, derivatives need to be isolated in which the pJCB12 vector has been lost. Such derivatives may be selected by supplementing the bacteriological growth medium with 5% sucrose. This sucrose selection may be made more efficient using a modified L-medium in which the NaCl ingredient is absent and supplemented with 5% sucrose. Under these conditions the sacB gene of pJCB12 is toxic, and only derivatives where the sacB gene has been lost will grow. This event again occurs by homologous recombination and has a number of outcomes. Firstly, a reversion event will result in the targeted region remaining as it was. Secondly, homologous recombination may result in the defined genetic construct being swapped with the targeted region resulting in the defined construct being incorporated at the target region. In addition, if the targeted region is part of a plasmid, such as many of the toxin genes of ETEC strains, then two additional events may occur. These are, thirdly, an undefined spontaneous deletion event, resulting in the loss of a part of the targeted region which may extend beyond the boundaries of the defined genetic construct, and, fourthly, the loss of the whole plasmid, an event which may be termed "specific plasmid curing".

Testing of sucrose resistant derivatives by PCR can identify the desired recombinants. For this, oligonucleotides that hybridise at each end of the targeted region and outside of the defined genetic construct are used. If the PCR product is the same size as prior to introduction of the pJCB12-derivative construct, then a reversion event has occurred. If, for example the genetically defined construct is a deletion mutation, then the PCR product should be smaller than previously and of a predictable size. Specific plasmid curing and undefined spontaneous deletion will normally result in no PCR product or non-specific products of unexpected size in this type of PCR reaction.

In summary, vector pJCB12 (or another similar vector of the invention) may be used in a method for producing a bacterial cell in which a target gene (e.g. a toxin gene such as ST, LT or EAST1 or a chromosomal gene such as an omp or aro gene) is deleted, inactivated or replaced, which method comprises transferring the vector into a bacterial cell containing the target gene and selecting for a cell in which the target gene has been deleted, inactivated or replaced. The selection may be carried out using a multi-stage procedure along the following lines:

Selecting for a colony of cells which contains the selectable marker. If the cell into which the vector is transferred is one that does not support replication of the vector from the origin of replication in the vector, selecting for such a colony of cells identifies cells in which the vector has become incorporated into a cellular replicon;

Carrying out PCR to select for a cell in which the vector has correctly targeted to the target gene, wherein one of the primers used in the PCR hybridizes to vector sequence adjacent to the cloning site and the other hybridizes to a site in the cellular DNA adjacent to the target gene. A positive PCR indicates that the vector has targeted to the target gene.

Selecting for a cell from which vector sequence has been lost by growing the cell under conditions which make effective the gene encoding a product that is toxic to the cells when grown under defined conditions. Survival of a cell indicates that vector sequence has been lost. Where the gene encoding the toxic product is sacB, the cell may be grown in medium supplemented with sucrose and from which NaCl is absent; the product of sacB is toxic when the cells are grown in this medium.

Finally, PCR may be carried out using primers which hybridize at positions outside, and adjacent to each end of, the target gene, wherein a PCR product smaller than the product obtained from a wild-type cell indicates a deletion mutation.

For example, in the present study, in general:

Bacterial Conjugations were performed by mixing donor and recipient ETEC strains on L-agar and incubating at 37° C. for 3 to 18 h. Bacterial growth was scraped off into L-broth and plated onto L-agar plates supplemented with chloramphenicol and another appropriate antibiotic to select ETEC strains (streptomycin for strain B, tetracycline for other ETEC strains) that had incorporated the pJCB12-derivative. For identification of correctly targeted recombinants, transconjugants or transformants obtained by growth on L-agar supplemented with chloramphenicol following introduction of pJCB12-derivative constructs were tested by PCR in order to identify those in which the desired genetic locus had been targeted. For this, one of the oligonucleotides hybridised within the pJCB12 nucleotide sequences adjacent to the multiple cloning site (MCS) where the defined genetic construct had been inserted. The other oligonucleotide hybridised to the genome, adjacent to but outside of the defined genetic construct. In such a PCR, the generation of a fragment indicated that the binding sites for the respective oligonucleotides had become linked, which could occur only if the pJCB12-derivative had targeted the correct region of the genome.

pJCB12 was excised from transconjugants by growth in the presence of 5% sucrose. Transconjugants or transformants having the pJCB12-derivative targeted to the correct region of the genome were then streaked onto fresh L-agar supplemented with chloramphenicol and another appropriate antibiotic to select ETEC strains (see above), and incubated at 37° C. to allow colonies to grow. L-broth cultures inoculated from these fresh plates were then grown. Cells from these cultures were harvested, resuspended in 5% sucrose broth, and incubated overnight prior to plating serial dilutions on 5% sucrose agar in order to select recombinants in which the pJCB12-derivative had excised. The inoculated sucrose agar plates were then incubated overnight and the resulting colonies tested by PCR using relevant oligonucleotides in order to identify mutants.

TABLE 1

STRAIN CHARACTERISTICS

| Strain | Parent Strain | Accession Number | LPS:flagellin | Antibiotic Resistance | CS Proteins | Regulator | Toxin Genes |
|---|---|---|---|---|---|---|---|
| E1392/75-2A | E1392/75 | N/A | 06:H16 | Strep | CS1 CS3 | ms | None |
| PTL003 | E1392/75-2A | 01090302 (submitted as ACM 2005) | 06:H16 | Strep | CS1 CS3 | ms | None |
| ACAM2008 | PTL003 | 02082965 | 06:H16 | None | CS1 CS3 | ms | None |
| WS-2773E | N/A | N/A | 039:H12 | None | CS5 CS6 | ?csvR | ST EAST LT |
| WS-2773E-Tox minus | WS-2773E | 01090305 (submitted as ACM2002) | 039:H12 | None | CS5 CS6 | ?csvR | None |
| ACAM2006 | WS-2773E-Tox minus | N/A | 039:H12 | None | CS5 CS6 | ?csvR | None |
| ACAM2012* | ACAM2006 | 02082968 | 039:H12 | None | CS5 CS6 | ?csvR | None |
| WS-3504D | N/A | N/A | 0141:H5 | Amp | CS2 CS3 | ms | EAST |
| WS-3504D-Tox minus | WS-3504D | 01090304 (submitted as ACM 2003) | 0141:H5 | Amp | CS2 CS3 | ms | None |
| ACAM2007 | WS-3504D-Tox minus | 02082964 | 0141:H5 | None | CS2 CS3 | ms | None |
| WS-1858B | N/A | N/A | 071:H- | Amp/Tmp/Smz | CFA/1 | ms | ST EAST |
| WS-1858B-Tox minus | WS-1858B | N/A | 071:H- | Amp/Tmp/Smz | CFA/1 | ms | None |
| ACAM2010 | WS-1858B-Tox minus | 02082967 | 071:H- | None | CFA/1 | ms | None |
| WS-2252A | N/A | N/A | 015:H18 | None | CS4 CS6 | cfaD | ST EAST LT |
| WS-2252A-Tox minus | WS-2252A | 01090306 (submitted as ACM2004) | 015:H18 | None | CS4 CS6 | cfaD | None |
| ACAM2009 | WS-2252A-Tox minus | 02082966 | 015:H18 | None | CS4 CS6 | cfaD | None |
| WS-2511A | N/A | N/A | 04:H- | None | CS4 CS6 | cfaD | ST EAST X 2 |
| Strain K | WS-2511A-Tox minus | N/A | 04:H- | None | CS6 | cfaD | ST EAST X 2 |

*ACAM2006 contains a lysogenic phage in its chromosome. ACAM2012 is a derivative of ACAM2006 from which a large part of the genome, including genes critical for phage assembly, have been deleted.

TABLE 2

| Strain | CS Antigen Expression | Accession No | Date of Deposit |
|---|---|---|---|
| PTL003 or ACM 2005 | CS1, CS3 | 01090302 | 3 Sep. 2001 |
| WS-4437A-Tox minus or ACM 2001 | CFA/I | 01090303 | 3 Sep. 2001 |
| WS-3504D-Tox minus or ACM 2003 | CS2, CS3 | 01090304 | 3 Sep. 2001 |
| WS-2773E-Tox minus or ACM 2002 | CS5, CS6 | 01090305 | 3 Sep. 2001 |
| WS-2252A-Tox minus or ACM 2004 | CS4, CS6 | 01090306 | 3 Sep. 2001 |
| ACAM 2007 | CS2, CS3 | 02082964 | 29 Aug. 2002 |
| ACAM 2008 | CS1, CS3 | 02082965 | 29 Aug. 2002 |
| ACAM 2009 | CS4, CS6 | 02082966 | 29 Aug. 2002 |
| ACAM 2010 | CFA/I | 02082967 | 29 Aug. 2002 |
| ACAM 2012 | CS5, CS6 | 02082968 | 29 Aug. 2002 |
| ACAM 2013 | CS4, CS5, CS6 | 02082969 | 29 Aug. 2002 |

Each of the strains listed in Table 2 was deposited with the European Collection of Cell Cultures (ECACC), CAMR, Salisbury, Wiltshire, SP4 0JG, United Kingdom in accordance with the Budapest Treaty on the date shown therein.

TABLE 3

| Strain | Code | Phenotype | CFA | LT | ST | EAST1 |
|---|---|---|---|---|---|---|
| WS-1858B | A | O71:H— | CFA/I | − | + | + |
| WS-4437A | B | O128:H12 | CFA/I | − | + | − |
| WS-6117A | C | O153:H45 | CFA/I | − | + | + |

TABLE 3-continued

| Strain | Code | Phenotype | CFA | LT | ST | EAST1 |
|---|---|---|---|---|---|---|
| WS-2560B | D | O25:H— | CS4, CS6 | + | + | + |
| WS-2773E | E | O39:H12 | CS5, CS6 | + | + | + |
| WS-4150D | F | O6:H16 | CS2, CS3 | + | − | ? |
| WS-6170A | G | O17:H18 | CS2, CS3 | − | + | ? |
| WS-3504D | H | O141:H5 | CS2, CS3 | + | + | + |
| WS-3517A | I | O6:H— | CS2, CS3 | − | + | + |
| WS-2252A | J | O15:H18 | CS4, CS6 | + | + | + |
| WS-2511A | K | O4:H— | CS4, CS6 | − | + | + |
| WS-2556A | L | O6:H1 | CS4, CS6 | − | + | + |
| WS-4046A | M | O39:H— | None identified | + | − | N.D. |

TABLE 4

OLIGONUCLEOTIDES USED

| Name | Nucleotide sequence | Target locus; use |
|---|---|---|
| 47151 | 5' CCGGTCGACCTTATTGAGGAATATCGG (SEQ IN NO: 12) | Cloning csaA (up to Bglll site). Binds 200 bp upstream. |
| 47152 | 5' GGCGCATGCAGATCTGATTAGAGC (SEQ IN NO: 13) | Cloning csaA (up to Bglll site). Includes Bglll & Sphl sites. |
| 47150 | 5' GGCGCATGCCGGAATTCCATTTGAGACTCCC (SEQ IN NO: 14) | Checking orientation of 3' region of CS4 operon in plasmid pACYC-CS4. |
| RNS-03 | 5' ACATCATAGCGATGGCATCAA (SEQ IN NO: 15) | Cloning the rns gene from E1392/75-2A. Binds upstream of the gene |
| RNS-04 | 5' TATTTCAATTCAGTTCGCATCGC (SEQ IN NO: 16) | Cloning the rns gene from E1392/75-2A. Binds downstream of the gene. |
| 47173 | 5' GACGGATCCGAATGCGAGGCATCCGGTTG (SEQ IN NO: 17) | Forward primer for amplifying upstream region of ompC. Includes BamHI site. |
| 47174 | 5' TTCCTCAATAAGCTCTGTTATATGCCTTTAT TTGC (SEQ IN NO: 18) | Reverse primer for amplifying upstream region of ompC. Includes csaA overlap. |
| 47177 | 5' TCTAATCAGATCTCGACAACCAGTTCACTCGTG (SEQ IN NO: 21) | Forward primer for amplifying downstream region of ompC. Includes csaA overlap. |
| 47178 | 5' GGTGGATCCGTTAAAGCGCATCAGCGCGG (SEQ IN NO: 22) | Reverse primer for amplifying downstream region of ompC. Includes BamHI site. |
| 47175 | 5' TATAACAGAGCTTATTGAGGAATATCGGTGTC (SEQ IN NO: 19) | Forward primer for amplifying csaA. Includes ompC overlap. |
| 47176 | 5' TGGTTGTCGAGATCTGATTAGAGCCGCATA (SEQ IN NO: 20) | Reverse primer for amplifying csaA. Includes ompC overlap. |
| 47180 | 5' CCGTCCTGTGGATCCTCTACGCCGG (SEQ IN NO: 23) | Construction of pACYC Xmal. Binds across the BamHI site. |
| 47182 | 5' ATCGGTCGACGCTCTCCCGGGTGCGACTCC (SEQ IN NO: 24) | Construction of pACYC Xmal. Binds across the Sall site. Introduces Xmal. |
| 4732 | 5' GTACAAATAACCTACAAAAAGCCC (SEQ IN NO: 25) | CS4 chromosome linkage/CS4 retained in ompC locus. |
| 47105 | 5' TAACGCCTGCTCTAACATTCCC (SEQ IN NO: 26) | CS4 chromosome linkage/CS4 retained in ompC locus. |
| 47168 | 5' CGTTATGCAGGAATAATTACG (SEQ IN NO: 27) | Confirm presence of CS5 in pACYC-CS5. |
| 47167 | 5' CGTATTTTTATCAACCTTAGC (SEQ IN NO: 28) | Confirm presence of CS5 in pACYC-CS5. |
| 4714 | 5' TTCAACCTTAAAAGCTTTAAAAGCCT (SEQ IN NO: 29) | oriR6K; construction of pJCB12 |
| 4715 | 5' CTACACGAACTCTGAAGATCAGCAGTTCAACC (SEQ IN NO: 30) | oriR6K; construction of pJCB12 |
| 4716 | 5' GATCTTCAGAGTTCGTGTAGACTTTCCTTGG (SEQ IN NO: 31) | mobRP4; construction of pJCB12 |
| 4717 | 5' GCCACTGCAGCCTCGCAGAGCAGGATTC (SEQ IN NO: 32) | mobRP4; construction of pJCB12 |
| 4718 | 5' GGCACTGCAGGCGTAGCACCAGGCGTTT (SEQ IN NO: 33) | cat; construction of pJCB12 |
| 4719 | 5' TCATCCGGAGTTCCGTATGGCAAT (SEQ IN NO: 34) | cat; construction of pJCB12 |
| 4720 | 5' TGCCATACGGAACTCCGGATGAG (SEQ IN NO: 35) | cat; construction of pJCB12 |
| 4721 | 5' GCTTTTAAAGCTTTTAAGGTTGAATTCGATCGGCACGTAAGAGGTTC (SEQ IN NO: 36) | cat; construction of pJCB12 |
| 4722 | 5' GGCCTGCAGGCAAGACCTAAAATGTG | sacB; construction of pJCB12 |

TABLE 4-continued

OLIGONUCLEOTIDES USED

| Name | Nucleotide sequence | Target locus; use |
|---|---|---|
| | (SEQ IN NO: 37) | |
| 4723 | 5' GCGCTGCAGCTTTATGTTGATAAGAAA<br>(SEQ IN NO: 38) | sacB; construction of pJCB12 |
| 4766 | 5' CAACAGTACTGCGATGAGTGG<br>(SEQ IN NO: 39) | cat; nucleotide sequence determinations into sacB |
| 4917 | 5' ATCAACGGTGGTATATCCAGT<br>(SEQ IN NO: 40) | cat of pJCB12; confirmation of linkage. |
| R6K-01 | 5' GTGACACAGGAACACTTAACGGC<br>(SEQ IN NO: 41) | oriR6K; confirmation of linkage |

The sequences shown in Table 4 are SEQ ID NOS: 12 to 41, respectively.

TABLE 5

GENBANK ACCESSION NUMBERS FOR SEQUENCE DATA

| | |
|---|---|
| EAST1 (astA) | AF143819 |
| ST (estA) | M18346 |
| LT-A (eltA) | V00275 |
| LT-B (eltB) | M17874 |
| CFA/I operon | M55661 |
| CS1 operon | M58550 |
| | X62495 |
| | X76908 |
| CS2 operon | Z47800 |
| CS3 operon | X16944 |
| CS4 operon | AF296132 |
| CS5 operon | AJ224079 |
| CS6 operon | U04844 |
| cfaD | M55609 |
| csvR | X60106 |
| rns | J04166 |
| parDE RK2 | L05507 |
| sacB | X02730 |
| oriR6K | M65025 |
| mobRP4 | X54459 |
| cat | V00622 |

REFERENCES

1. Aitken and Hirst (1993) Vaccine 11(2), 227-233.
2. Ausubel et al; *Current Protocols in Molecular Biology.* 1995: John Wiley & Sons Inc.
3. Burkardt, H. J., G. Riess, and A. Puhler, *Relationship of group P1 plasmids revealed by heteroduplex experiments: RP1, RP4, R68 and RK2 are identical.* J Gen Microbiol, 1979. 114(2): p. 341-8.
4. Chatfield WO 99/49026
5. Chang A. C. and Cohen S. N. (1978) Journal of Bacteriology 134(3): 1141-1156
6. Charles WO92/15689
7. Chong et al (1998) Vaccine 16, 732-740.
8. Cieplak et al (1995) Journal of Biol. Chem. 270(51), 30545-30550.
9. Clements (1990) Infect. & Immun. 58(5), 1159-1166.
10. Cravioto, A. 1980, PhD Thesis, University of London, London, United Kingdom.
11. de Haan L. A., Willshaw, G. A., Van der Zeijst B. A. and Gaastra W. (1991) FEMS Microbiol Lett 67 (3): 341-346
12. Donnenberg, M. S. and J. B. Kaper, *Construction of an eae deletion mutant of enteropathogenic Escherichia coli by using a positive-selection suicide vector.* Infect Immun, 1991. 59(12): p. 4310-7.
13. Dunstan, S., Simmons, C. and Strugnell, R. *Use of in-vivo regulated promoters to deliver antigens from attenuated Salmonella typhimurium.* Infection and Immunity (1999) 67, 5133-5141.
14. Duthy T. G., Staendner L. H., Manning P. A. and Heuzenroeder M. W., (1999) Journal of Bacteriology 181 (18): 5847-5851.
15. Duthy et al (2001) Microbial Pathogenesis 31: p 115-129
16. Everest, P., et al., *Expression of LacZ from the htrA, nirB and groE promoters in a Salmonella vaccine strain: influence of growth in mammalian cells.* FEMS Microbiol Lett, 1995. 126(1): p. 97-101.
17. Froehlich, B. J., A. Karakashian, H. Sakellario and J. R. Scott, *Genes for CS2 Pili of Enterotoxigenic Escherichia coli and their Interchangeability with those for CS1 Pili.* Infection and Immunity, 1995 63(12): p. 4849-4856.
18. Gerdes, K., P. B. Rasmussen, and S. Molin, *Unique type of plasmid maintenance function: post segregational killing of plasmid-free cells.* Proc Natl Acad Sci USA, 1986. 83(10): p. 3116-20.
19. Gerdes, K., et al., *The hok killer gene family in gram-negative bacteria.* New Biol, 1990. 2(11): p. 946-56.
20. Jalajakumari M. B. et al (1989) Molecular Microbiology 3(12): 1685-1695.
21. Kolter R. et al (1978) Cell 15: 1199-1208.
22. Laemmli, U. K., *Cleavage of structural proteins during the assembly of the head of bacteriophage T4.* Nature, 1970. 227(259): p. 680-5.
23. Miller, V. L. and J. J. Mekalanos, *Synthesis of cholera toxin is positively regulated at the transcriptional level by toxR.* Proc Natl Acad Sci USA, 1984. 81(11): p. 3471-5.
24. Milton, D. L., et al., *Flagellin A is essential for the virulence of Vibrio anguillarum.* J Bacteriol, 1996. 178(5): p. 1310-9.
25. Roberts, R. C., A. R. Strom, and D. R. Helinski, *The parDE operon of the broad-host-range plasmid RK2 specifies growth inhibition associated with plasmid loss.* J Mol Biol, 1994. 237(1): p. 35-51.
26. Sambrook, J., E. F. Fritsch; and T. Maniatis, *Molecular cloning: a laboratory manual.* 2nd ed. 1989: Cold Spring Harbor Laboratory Press, Cold Spring Harbor, N.Y.
27. Scott J. R. et al (1992) Molecular Microbiology 6(3): 293-300
28. Simon, R., U. Priefer, and A. Puhler, *A broad host range mobilisation system for in vivo genetic engineering: transposon mutagenesis in Gram negative bacteria.* Bio/Technology, 1983. 1: p. 784-791.
29. Summers et al, Mol. Genet. Genes., 201(2): 334-338.

30. Tao, B. Y. and K. C. P. Lee, *Mutagenesis by PCR*, in *PCR Technology: current innovations*, H. G. Griffin and A. M. Griffin, Editors. 1994, CRC Press, Inc.: Boca Raton, Fla. p. 69-83.

31. Turner, A. K., et al., *Construction and characterization of genetically defined aro omp mutants of enterotoxigenic Escherichia coli and preliminary studies of safety and immunogenicity in humans.* Infect. Immun., 2001. 69(8): p. 4969-79.

32. Valdivia, R. and Falkow, S. *Fluorescence-based isolation of bacterial genes expressed within host cells.* Science (1997), 277, 2007-2011.

33. Willshaw G. A. et al (1988) Fems Microbiol Lett 49: 473-478

34. Wolf, M. K. *Occurrence, Distribution and Association of O and H Serogroups, Colonisation Factor Antigens and Toxins of Enterotoxigenic Escherichia coli.* Clinical Microbiology Reviews, 1997 10 (4): p 569-584.

35. Wolf M. K. et al (1997) Fems Microbiol Lett 148(1): 35-42.

The invention claimed is:

1. An essentially purified and isolated enterotoxigenic *E. coli* (ETEC) cell which expresses coli surface antigens CS1, CS2 and CS3 and is attenuated by deletion or inactivation of ompC.

2. An ETEC cell according to claim 1 which is further attenuated by deletion or inactivation of each of aroC and ompF.

3. An ETEC cell according to claim 1 which does not express one or more of heat stable toxin (ST), heat labile toxin (LT) and EAST 1.

4. An ETEC cell according to claim 3 which is obtainable by a method comprising site-directed deletion of the whole of the LT gene and/or the whole of the EAST 1 gene.

5. An ETEC cell according to claim 1 which does not express an antibiotic resistance gene.

6. An ETEC cell according to claim 1 which further expresses a heterologous antigen in addition to the CS antigens.

7. An ETEC cell according to claim 6 wherein the heterologous antigen is an *E. coli* antigen.

8. An ETEC cell according to claim 6 wherein the heterologous antigen is a non-toxic component or form of LT.

9. An ETEC cell according to claim 8 wherein the non-toxic component of LT is the B subunit.

10. An ETEC cell according to claim 1 which is obtainable by a method comprising introduction of a polynucleotide encoding a heterologous CS1 antigen into an ETEC cell that expresses CS2 and CS3.

11. An ETEC cell according to claim 10 wherein the polynucleotide comprises the operon of the heterologous CS1 antigen.

12. An ETEC cell according to claim 10 wherein the heterologous CS1 antigen coding sequence is carried on a stable plasmid in the cell.

13. An ETEC cell according to claim 10 wherein the heterologous CS1 antigen coding sequence is inserted in the bacterial chromosome of the cell.

14. A method for making an ETEC cell according to claim 1, which comprises introducing a polynucleotide encoding ETEC CS1 antigen into a CS2- and CS3-expressing ETEC cell.

15. A method according to claim 14 wherein the polynucleotide comprises the operon of the CS1 antigen.

* * * * *

SEQUENCE LISTING

<160> NUMBER OF SEQ ID NOS: 41

<210> SEQ ID NO 1
<211> LENGTH: 703
<212> TYPE: DNA
<213> ORGANISM: Escherichia coli
<220> FEATURE:
<221> NAME/KEY: gene
<222> LOCATION: (114)..(629)
<223> OTHER INFORMATION: cooA

<400> SEQUENCE: 1

```
atcgatagtg ttgatggaag cgcgggcaag caaggaaagc gaatgctaat aagcattcat      60
tgagtattac ttgggtatct taattttcca taataaaaca taatggagtt tatatgaaac     120
taaagaaaac aattggcgca atggctctgg cgacattatt tgcaactatg ggagcatctg     180
cggtcgagaa gaccattagc gttacggcga gtgttgaccc gactgttgac cttctgcaat     240
ctgatggctc tgcgctgccg aactctgtcg cattaaccta ttctccggct gtaaataatt     300
ttgaagctca caccatcaac accgttgttc atacaaatga ctcagataaa ggtgttgttg     360
tgaagctgtc agcagatcca gtcctgtcca atgttctgaa tccaaccctg caaattcctg     420
tttctgtgaa tttcgcagga aaaccactga gcacaacagg cattaccatc gactccaatg     480
atctgaactt tgcttcgagt ggtgttaata agtttcttc tacgcagaaa ctttcaatcc      540
atgcagatgc tactcgggta actggcggcg cactaacagc tggtcaatat cagggactcg     600
tatcaattat cctgactaag tcaacgtaat tattcagaat tacaacggaa gtcttttaag     660
ccagagcagc ggtgtgatgc tgctctgttt ctgtttgtct aga                       703
```

<210> SEQ ID NO 2
<211> LENGTH: 1714
<212> TYPE: DNA
<213> ORGANISM: Escherichia coli
<220> FEATURE:
<221> NAME/KEY: gene
<222> LOCATION: (1001)..(1714)
<223> OTHER INFORMATION: cooB

<400> SEQUENCE: 2

```
gttgtacgca gacttatggt ggaggaacag cttgtcgtca gccgtaaccg tcgtcgcgct      60
acagctcata ttgcggagaa atcggaccgg ctccggataa ccttatcgcc agagatttta     120
aggcggagca acctaatcag aaatggctgc cagatatcac ggagttccag ttccctgcag     180
gtaaagtctg gctatcaccg gtggtggact gcttcgatgg aaaagttgtg agctggtctc     240
tcagtacacg ccccgatgct gaactggtca acactatgct ggatagcgct gtcgaaacgt     300
taaatgctgg cgaacaaccg gtgatacaca gtgacagagg tgggcattat cgctggccag     360
gctggctgga aagagtgaat gcagcaggtc ttattcgctc aatgtcccgt aaaggatgtt     420
```

-continued

```
cacctgataa tgccgcatgc gaaggctttt tcggcagact gaaacggaaa tgtattatgg    480
gcgtaaatgg tcggcatcac gccagaaaag ttcatgcagc aagtggatgc ttacatcaga    540
tggtataacg agcggcgtat aaaattatcg ctgggtgccg tcagcaccaa aatgtaccgc    600
caataatgtg gactggcata taaaagccgt ccaggaaatt atccagatcc cccccacag    660 tgagtcataa tcatcctgac tttccagaac catatggatc gcccgctgac ggacttcggg    720
ggagaagtgc gtattttat tcatcttgtt tacctctttc tctgggagtt tagtcaccaa    780
gaactcgggg cagttcaaaa tggttgtcgg aatataactg tgaatgccaa catgaatcac    840
tgaacaacat gatgtcgcag gaataaatcg atatttaaat gtcaccaagg gcaagcgcca    900
ttggctgctt taatatttgt tgtaatggtt gctgtgtgtt atttatttat ttgattgttg    960
attgctgttt gtttaaagtg gccaagtgtt aggaggggt atgcgaaaat tatttttaag   1020
tttgcttatg attcccttg ttgcgaaggc gaacttatg atctatccaa tatcaaaaga   1080
aatcaaagga ggcagtagtg aacttattcg tatatattct aaatcaaaag atacacaata   1140
tataaaagtg tatactaaaa aagttttaaa tccggggaca aaggaagaat acgaggtaga   1200 cacccaaat tgggagggag ggttggttac tacgccgtcc aaagtaatct taccgggtgg   1260
gggcagtaag tccgttcggt taagtcagtt aaaggacatc agtagcgaag atgtctacag   1320
agtgtatttt gaatcaatta aaccagaaaa acaggatggt ttatcgaaaa ataaatcgct   1380
gaaaacagac ctatctgtca acattatata tgcggcatta ataagagtgc tccccaagga   1440
tgggaaaagt gatatgagag catcattatc acccaagagc agtcttctta taagaacac   1500 aggaaatgtg cgggtcggaa taaagatgc tttttttgt aaaaaacaa gcattaacaa   1560 tgatgactgc ataagaaaa catacaacaa gaatatctat cccggttcat catttgatac   1620
aggggttata caaaatggat tctcgcatat ttttatcgat agtgttgatg gaagcgcggg   1680
caagcaagga aagcgaatgc taataagcat tcat                             1714
```

```
<210> SEQ ID NO 3
<211> LENGTH: 5336
<212> TYPE: DNA
<213> ORGANISM: Escherichia coli
<220> FEATURE:
<221> NAME/KEY: gene
<222> LOCATION: (85)..(2703)
<223> OTHER INFORMATION: cooC
<220> FEATURE:
<221> NAME/KEY: gene
<222> LOCATION: (2700)..(3791)
<223> OTHER INFORMATION: cooD

<400> SEQUENCE: 3
```

```
taattattca gaattacaac ggaagtcttt taagccagag cagcggtgtg atgctgctct     60
gtttctgttt gtctagagga atatatgatt ggtggaaagt cgagcaaggt ggtcattgtg    120
ttatccgttc ttattggatc ttcttccgga tttgccagca aatacaacct tgttgatatt    180
ccggagtctt ttcgtgattt atggggagag caggacgaat tactcgaagt cagactttat    240
gggcaatctc ttggcgttca tcgtattaag tccactccta ctactgtggc atttgagtct    300
ccggataatt tattagataa aattgagatt aataaggaa aggaagctga cttaagagta    360
cttatgcgag gttcattcca acggaatgga atatgagtt gccagggata tacgggacag    420
aacaactgca attacattaa aacaaacaca gttcggtta tcgtagatga tgttgaaaat    480
gtacttaatc ttttttatagg aaatgagttt cttgcttccg gagagaatga cagtgattat    540
tatcagccat ccaagaacac aaaaaaagca ttcatacata gccagacaat taatttatct    600
```

```
gataccggta attatgaaaa cttgtccatt gtcgggacgg gttcgcttgg gataacagat    660
aacagttatg ctattttggg ttgggcagca aattataatc ggtataaatc ttacaattac    720
aatgaacagt cgattaacag cctgtatttc agacatgatt ttgaaaaaaa tttttactat    780
cagttgggac ggatagacag atccgactta tcgcaaagta gtggcggaaa ctttaacttc    840
gatctacttc ctgtacctga tatttatggt atgagagccg gaacgactca gtcatatatc    900
aagaatacgg gaaagtcagt tgcatctccg gtcacaatta tgctgaccca cttttcccgt    960
gtagaagcat atcgaaatgg gcaattactg ggagtttggt atttagatgc aggtatcagt   1020
gagttagata cggagcgttt acctgacgga aattacgatc tgaaattaaa aatatttgag   1080
caggagcaac ttgtccgtga agaaattgta ccttttaaca aatcaggttc ttcaattggt   1140
gacacgcatt gggatgtttt cgtgcaggca ggcgatatta taaatgataa tggccgatat   1200
gttgaaaaac agaaaaacca taaatcagcc attaatagtg gattacgttt accgttaaca   1260
aggaatcttg cagtacagct ggggggggct gttattgata taaaaaatta ttacgagact   1320
gggattctgt ggaactcagg actccttgat ggttctctca atagcaaatt cactttcctt   1380
tttggtgacg acacacatgg aaactatcag aatgtttcct atactgatgg tttcagctta   1440
tcgttctatc ataatgataa gcgagttgat gattgtggta aagattacaa tatgggctgg   1500
agtggatgtt atgagtctta ttcagcgtct ttaagtatcc ctgtgaaagg gtggaatagc   1560
actcttgcat acagtaatac gtacagtacg tctgtataca gatatgatgc tgtttctgaa   1620
tatgttcctt attactatta taaggaagaa actaaaagat ggcaacttac tgcttctacg   1680
gtggtaagat gggggggacta taacattatg ccaacaatag gagtatataa tagtgaacag   1740
aaacaatggg ctgataaagg aggctattta tccttaacgc ttactcgagt tgatggtggc   1800
aagtccttga atgctggtta ttcctataac tactcccggg gtaattatac ttctaatgat   1860
gcatttgttg aggggcatct ggtttcagat acaaatgtca gttatcgtga actaagtgca   1920
cgcgtcagtg gtaatagata ttacactgag ggaggagttt cagggcgcat taacaataga   1980
tttggtgatc tgaatgggac acttaatgtt aataaaaaca gaaaatcaca tgatacaact   2040
cactctctga cagctggtta cagttcgtca tttgctctta cgaccgatgg catctactgg   2100
ggaggaagcg catccgggct gacgaattta tccggaggaa ttgtaagagt aaaatcaaat   2160
gaggatgaga gtgaactatt gaatgtgaaa ggctcatcat atggtcatta ttccctgggc   2220
agcaatgata gtttatttat acctgtacct gccctgatgc aagccagcct tactattgaa   2280
gagaatacaa ataaatctaa aaatattgat gtgctcgcac caacaaaaaa cactttttt   2340 atgttacctg gaagtgttta tcctattgat gtttcagcca atgttagttt tacttacgtt   2400
ggacgtggag ttgatgttaa gggacgacct ttatctggtg catatatttt gaatgcgcaa   2460
aatattgtgt tggatgaaaa tggtggattt tcttttgaga gttcagagaa tgagaaggaa   2520
ctctttttat taaagataaa aacaatttat tcctgttcat tagacagaag cgaaatgcgc   2580
aatggtattg cttcgttgg tgaggttgca tgcaattcta ccatcaaaga acttcttcct   2640
gaaaaattgg ttacaaattc tcgcattcat gatttattag cttacaatca ggatactgaa   2700
tgaaaaagat atttattttt ttgtctatca tattttctgc ggtggtcagt gccgggcgat   2760
acccggaaac tacagtaggt aatctgacga agagttttca agcccctcgt ctggatagaa   2820
gcgtacaatc accaatatat aacatcttta cgaatcatgt ggctggatat agtttgagtc   2880
atagcttata tgacaggatt gttttttttat gtacatcctg tcgaatccg gttaatggtg   2940 cttgcccaac cattggaaca tctggagttc aatacggtac tacaaccata accttgcagt   3000
```

```
ttacagaaaa aagaagtctg ataaaaagaa atattaatct tgcaggtaat aagaaaccaa    3060
tatgggagaa tcagagttgc gactttagca atctaatggt gttgaattcg aagtcttgga    3120
gctgtggggc tcacggaaat gctaacggaa cacttctaaa tctgtatatc cctgcaggag    3180
aaatcaacaa attgcctttt ggagggatat gggaggcaac tctgatctta cgcttatcaa    3240
gatatggcga agtcagtagc acccattacg gcaattatac cgtaaatatt acggttgatt    3300
taactgataa aggtaatatt caggtatggc ttccagggtt tcacagcaac ccgcgtgtag    3360
acctgaatct gcgccctatc ggtaattata aatatagtgg tagtaattca ctcgacatgt    3420
gtttctatga tggatatagt acaaacagtg atagcatggt aataaagttc caggatgata    3480
atcctaccaa ttcatctgaa tataatcttt ataagatagg gggcactgaa aaattaccat    3540
atgctgtttc actgcttatg ggagaaaaaa tattttatcc agtgaatggt caatcattta    3600
ctatcaatga cagtagtgta ctcgaaacaa actggaatcg agtaaccgca gttgctatgc    3660
cggaagttaa tgttccagta tatgctggc cagcaagatt gctattaaat gctgatgtaa    3720
atgctcccga tgcaggacag tattcaggac agatatatat aacatttaca cccagtgtcg    3780
aaaatttatg acaaatatgc atatttggca agaaaaatc tgacactggg cattgtatgt    3840
ggcgatggga ggtaactctg ataaatcggg ataggaactg ttctcacgat tccgactcat    3900
cccactgtac cgtacatacg gggtcgtata cggcggtttg gttatgttga ttgtcgcctg    3960
cctatatttc aggcaggatc agtctggtga acagattata gagtacaggt gtcttgtatg    4020
ataacgcgat ggcggagagc atcaatagtc ttgacaaagc gagggcttta agtgctttgt    4080
cgaaatcgaa gggctgggac atgtgtcatt cctttttgat tgtatattat ggaatgacac    4140
agaatttcta acactctcga gctgacaccc taagttcaca gataaaatat tctctaggat    4200
actcggggcg gttcatttcc cgttatgttc agcacttcat tcagcattct gaacagataa    4260
atatcgaata tttccgtaca gtatggtctt attggtaaat atacgtcgtc tgttgggata    4320
aagttcatta acctagcttc taaggaatga ggtggtgagc gactcgggaa aaggcagaga    4380
tctactgtca cgtggagttc gggaagctga acgaaagtaa actgtccgat gaagcatcga    4440
aatcttagat gatgtcaaaa tggggctgga tttgccccta tatttccaga catctgttat    4500
cacttaaccc attacaagcc cgctgccgca gatattcccg tggcgagcga taacccagcg    4560
cactatgcgg atgccattcg ttataatgct cgaacgcctc tgcaaggttc tttgctgccg    4620
ttaacccgtc tggtttgggc atgatactga tgtagtcacg ctttatcgtt ttcacgaagc    4680
tctctgctat tccattactc tccggactcc gcaccgccgt gttcttcggt tcaagtccca    4740
acatccgggc gaactggcgt gtttcattag cccggtagca tgaaccatta tccgtcagcc    4800
actccactgg agacgacgga agatcgttgc cgaagcggcg ttccaccgct cccagcatga    4860
cgtcctgtac tgtttcactg ttgaagccgc cggtagtgac cgcccagtgc agtgcctcac    4920
gatcacagca gtccagcgcg aacgtgacac gcagtctctc tccgttatca cagcagaact    4980
cgaacccgtc agagcaccat cgctgattgc tttctttcac ggccactctg cctgtatgtg    5040
cccgtttcga tggcggtaca gcaggttttc gctcaagcaa cagcgcattc tggcgcatga    5100
tccggtaaac acgtttggca ttgatcgcag gcataccatc aagttctgcc tgtctgcgaa    5160
gcagcgccca tacccgacga taaccatacg tgggcagctc tccgataaca tggtgtatac    5220
ggagaagcac atccgtatca tcagtgtgac gactgcggcg ccatccatc cagtcatcgg    5280 ttcgtctgag aatgacgtgc aactgcgcac gcgacacccg gagacaacgg ctgact        5336
```

<210> SEQ ID NO 4
<211> LENGTH: 2116
<212> TYPE: DNA
<213> ORGANISM: Escherichia coli
<220> FEATURE:
<221> NAME/KEY: gene
<222> LOCATION: (559)..(1356)
<223> OTHER INFORMATION: cfaD

<400> SEQUENCE: 4

| | | | | | | |
|---|---|---|---|---|---|---|
| aattcctatc | gatgaacagc | tatgcatata | tctcacaata | caacaaccat | taagcataag | 60 |
| tgcgtttaat | ataatattca | ttagcagtat | tatgatgcta | ctatttaaca | ctcaacaaaa | 120 |
| tataattcgt | caaagatatg | tcatgcataa | ccattacaat | atcattttt | gtttggattt | 180 |
| cggccaagaa | aatgcttcac | aaaacgttcc | tctatttatg | caccattcta | tattttcagc | 240 |
| attttacac | aaaagtgatg | cttgtttcca | aagttcaaag | gcagaaacta | atccatgtt | 300 |
| ttttctgcc | agcgcggcct | ttttttgat | agacatgaaa | acactcttct | tttactttca | 360 |
| ttgaaagatt | gtctctggta | aaatattagc | tgcacacaag | tgtatatcac | agcaaggcac | 420 |
| caagagata | aaataataat | aataataaaa | agcaaaaaaa | gttgaaaaaa | catatctttc | 480 |
| ttttagcgaa | agttaggcca | atcttgcgaa | aggtgattgt | acaagcaaat | caaacctctt | 540 |
| gcctttgta | ggtataagat | ggatttaaa | tacactgaag | aaaaagaaat | gataaaaatt | 600 |
| aataatatta | tgattcataa | atacactgta | ttatatacat | caaattgtat | tatggatata | 660 |
| tattcagaag | aagagaaaat | cacatgtttt | agtaacagac | ttgtatttct | tgaaagagga | 720 |
| gtaaatatat | ctgtaagaat | acagaagaaa | attttatcag | aaaggccata | tgttgcattc | 780 |
| agattgaacg | gagatatact | aaggcattta | agaatgcat | tgatgataat | atatggcatg | 840 |
| tcaaaagtag | ataccaatga | ttgtagaggc | atgtcaagaa | aaataatgac | aacagaggtg | 900 |
| aataaaacct | tgttggatga | attaaaaaat | ataaacagcc | atgatgactc | agcttttata | 960 |
| tctagcttaa | tatatttgat | ttcaaaaatt | gagaataatg | aaaaaataat | agaatcaatt | 1020 |
| tatatatcat | ctgtgagttt | tttttctgac | aaggtcagaa | atgttatcga | aaaagatcta | 1080 |
| tccagaaaat | ggacgctggg | tattattgca | gatgcattta | atgtatcaga | ataaccatc | 1140 |
| agaaaaagac | tagaatctga | gaacactaat | tttaatcaga | ttttaatgca | attaagaatg | 1200 |
| agcaaggctg | cgttattact | acttgaaaat | tcataccaga | tatctcagat | atcaaatatg | 1260 |
| attggaattt | ccagtgcgtc | ttatttat | agggttttta | ataaacatta | tggtgttaca | 1320 |
| ccaaagcagt | ttttactta | ttttaaaggt | ggataaaaac | aatcttattt | tgaatgtgtt | 1380 |
| gcataatact | atgctgtata | aaaatgtatc | tagtagagat | ttattgcgat | gcaaactgaa | 1440 |
| ttgaaataaa | attttttgtt | aacaaacaga | ttaatccttt | acaatattgg | cgcgtaatag | 1500 |
| cgcaatattg | ttgttatcta | gagtgtttga | ctacttgatc | gataggaatt | aaaaccccaa | 1560 |
| aagattaaaa | aaacaccaca | aaacggatat | ttcttcaaca | tcacttttgc | tccatatgaa | 1620 |
| cggaaccgac | gattaaactg | gatggctctg | attgattcag | ggtatgaatg | gcggttttt | 1680 |
| gctccgtttc | cctcaaaatg | gacgcaactt | cccctctgcg | gctctcagcc | gaccaccgca | 1740 |
| ttccgggcca | acgctcatg | catcaggacc | agctctgcca | ggacggtagc | ccgcttcagc | 1800 |
| accgtaaaac | gcatctgact | cccgcacagc | acgcacttca | gcgggtcaac | cttcagtaac | 1860 |
| ctctgataca | tccctctcca | ggtgatttgc | atcgccgttt | ttctcactgt | ctccgttatg | 1920 |
| gtgtacacca | cttcttccag | taaccgccgt | ttcgccggac | tgaagtggtc | aacaaaaact | 1980 |
| ggccaccgag | ttagagtttt | tccagtatcg | attttccgat | tcgtttgggg | gtaacccacc | 2040 |
| gttatattcg | tgcggtctta | gtgcgctgta | atatccaacg | atatagtccg | ttatggcgtg | 2100 |

```
agctgccatc gctgaa                                                      2116

<210> SEQ ID NO 5
<211> LENGTH: 5798
<212> TYPE: DNA
<213> ORGANISM: Escherichia coli
<220> FEATURE:
<221> NAME/KEY: gene
<222> LOCATION: (499)..(1215)
<223> OTHER INFORMATION: cotB
<220> FEATURE:
<221> NAME/KEY: gene
<222> LOCATION: (1255)..(1767)
<223> OTHER INFORMATION: cotA
<220> FEATURE:
<221> NAME/KEY: gene
<222> LOCATION: (1836)..(4436)
<223> OTHER INFORMATION: cotC
<220> FEATURE:
<221> NAME/KEY: gene
<222> LOCATION: (4451)..(5545)
<223> OTHER INFORMATION: cotD

<400> SEQUENCE: 5
ctgcagatgg cgctgtggcg gcgtaagagg ccccggaacg ttatcgttca cacggaccgt    60
ggaggccagt actgttcagc agattatcag gcgcaactga agcggcataa tctgcgtgga   120
agtatgagcg caaaaggttg ctgctacgat aatgcctgcg tggaaagctt ctttcattcg   180
ctgaaagtgg aatgtatcca tggagaacac tttatgagcc gggaaataag tcgggcaacg   240
gtgtttaatt atatcgaatg tgattacaat cggtggcggc ggcacagttg gtgtggcggc   300
ctcagtccgg aacaatttga aaacaagaac ctcgcttagg cctgtgtcca tattacgtgg   360
gtaggatcaa aacactatca ataagttgga gtcattaccg gcattcttga aagcctcatg   420
cgtgacaggg tgtgtgttgt atttttatca tattttaacg cctgctttct gataatgttt   480
aggaaagggg tgatatgtat gaagatattg ttatttgtta ttctgttttt taatgttttt   540
gctgccagtg caaattttat ggtatatccg atctcaaagg atatacagag tggtggcagc   600
gaaactataa agtttttttc aaaatctaaa gatgttcagt atataaagat atatacgaaa   660
agggttatta atccaggaac aaaagaagag caagaggttg atataaaaaa ttgggatgga   720
ggtctgattg taactccggc aaaagttgtt ttgccagctg gagcaagtaa gtcaatacga   780
cttactgaga taaataaaaa agagcaggag gaagtctatc gtgtgtattt tgaatctgta   840
aaaccgggac agcaagatga tatagaggaa aaaatgggc gtgtaaatac tgatttatca   900
gtaaacataa tctatgccgc tctcataaga accagccctg agaacccaca gaggaaactt   960
gatgtatcca tagaatcaaa caatgtatgg attaagaaca ctggaaatat taggctggga  1020
attaaggatg tattcttgtg tgatacaacc agcataaatg ataaatgtgc aaagtttttct  1080
tataatagaa atctatatcc agatatgtcg gtagatacta aattaggaaa aaaaggattt  1140
tcttatgctg tcattgatac aaaggatgac agaaatgaaa atagcggaga gttaattaac  1200
ataaagctcc cgtaagataa attgttcaat aaccactgta taagggtgta ataatgaaa  1260
ctcaataaga ttattggagc attagttctt tcatctacat ttgttagcat ggggcttct  1320
gctgccgaga aaaatatcac tgtaactgct agcgttgatc caactatcga tctgatgcaa  1380
tctgatggca cagcgttacc aagtgcagtt aatattgcat atcttccagg agagaaaaga  1440
tttgaatctg ctcgtatcaa tacccaagtt cataccaata taaaactaa gggtattcag  1500
ataaagctta ctaatgataa tgtggtaatg actaacttat ctgatccaag caagactatt  1560
cctttagagg tttcattcgc tggcactaag ctgagcacag ctgcaacatc tattactgcc  1620
```

```
gatcaattaa attttggcgc agctggtgta gagacagttt ctgcaactaa ggaactcgtt    1680
attaatgcag gaagcaccca gcaaactaat attgtagctg gtaactatca aggattggtg    1740
tcaattgtgc ttactcaaga accttaataa acattaagat atatcaacag ggttgctgat    1800
tttttagtca ccctgttatt aaagaaaata tatttatgcg agctttcaat aaaataactg    1860
ttttcatttt gtttattcct ggtttatgtt ttggaacgaa tggtttagag agtaaaaaaa    1920
atattcctga agaatttata gacttatgga tggaacagga tgaattactt gaagttaatt    1980
tatatgggcg ttctctaggt gttcatcgtg tattgacaac gcctactact gtgaaatttt    2040
catctgtaga ggaaattcta gaaagattaa tgtgaaaca agagaaaaaa gaagacctga    2100
gaagtcttct tcttcaatca tattcccgca acgggaatat gagttgtaat gggtttgatg    2160
aaaaggaata tagctgcaat tacattagaa ctgatacggt taatgttatt gtagatgaag    2220
aaaataatga gctaaatctt tttataggtg cgagttttct ttctgttcaa gctcaggata    2280
atatttatta tcaaaaaaat ataaactcag aaaaagcatt cattcacagt cagacaatta    2340
acttttctga atctgaaggg tataaaagtt tatctttgaa aggggttggt gcacaggggt    2400
taactgaaaa tagttatctt gttttttggtt gggatgccat atataatagt tctaggaaat    2460
acacatataa aaatcagtca atcaataata tatattacag atatgatttt gataaaaaat    2520
attattatca gttggggcga atggatcgtt cagatttatc aagtgcctct agtggtaatt    2580
ttaatttcaa tatgcttcct ttgcctgata ttgatggatt tcagataggt acgacccaat    2640
cctatattaa aaatatcgaa aaatcaatat catcgccagt aaccgttatg ttaacccgat    2700
tttctagggt tgaagccttt cgtaatgaag agttactggg agtatggtat ttgaattcag    2760
gaatcaatga tctcgataca agtcgtttgc ctgacggcag ttatgattta acgttgaaga    2820
tatttgagca ggacattctt gttcgtgaag agaaggtccc ttttaacaag ggaggagcct    2880
cttttgggga tatgcaatgg gatgtgtttg ctcaggctga taatattgtc aataataacg    2940
atagttatat tgagaagcaa actaataaaa aaacgggaat aaatgctggt atacgtacgc    3000
ctgtaaccag aaatttatcg ttcttacagg gcggtgctat aattgataat gataaatatt    3060
atgaggctgg tgttaactgg cgttcagggt ttcttgatgg ggtactaagt ggaaacttca    3120
gtttcctgta tggtgatggt gcaagaggaa attatcaaaa tatttcgtat accgatggtt    3180
ttaatctctc tttttatcgt aatgataaaa gcgttgataa ttgtagtcac aattacagtg    3240
cgggatggag tgggtgctat gagtcttatt ccttttcact aagtgttcct gtatctggct    3300
ggactactac tcttggctat aaccatacaa ataatgaggc tgtacataaa tatgattaca    3360
ccccggaata ttttttttagt aaaaaatata aggtgtcag taaagatgg caattgacat    3420 cttcttcgtc ctataaatgg atggattatc atgtgattcc gacgataggt gtatatcgta    3480
gtgatcagag tcgatggagt gagcagggag ggtattttc tttgagtttt acccgagtaa    3540
aggaaaatag tgccattaat gcaggatatt cttataatta tgtaaagcat aaaaatgcca    3600
cacatgaggc tttttttagat ggtcgtataa cgacaaatac ttttggctat agtgaattag    3660
gctctcgtat aaatacgaac aaaaataaca cagaagcagg tgttaccgga cgtgtaaaaa    3720
acaggtttgg agatctgaat ggttcattaa atgttaataa agtaaaaaca tccggtaaga    3780
tgactcactc aatgagtgca aactataact cctcatttgc aattactggt gattctgtct    3840 attgggggg agatgcctct ggtttaacga agctatctgg gggtgtggtg aatgtaagat    3900
cagatgataa atcaaaagag ctaataaaaa tatcaggttc ttcatatggt aattatatcc    3960
tcggcagtaa tgaccgttca tttatccctg taagtgcatt aatgccaagt aacctaacta    4020
```

```
tagaagagat tcagtcaaac gacaagaata ttactgttca ggcgttatca aaaaatgact    4080
tttttattct gcctggtaat gttttcccta ttgatgtaac tgctaatgtg acagtttctt    4140
atataggagg agctcttgat gataaaggaa atccattatc aaatgcccat atacttgatg    4200
ttcacggggt taggctggat gaggatggtg gttttcttt cgaaacttca gctcaaaaga    4260
aatctctttt cctgttaaaa gataaagata tttattcatg tgatgttaag aaatatgatt    4320
tacgtagtgg tgttttattt actggtgacc ttatatgtga acacagtggt atagaacgtc    4380
ttggaaaaga tttggttaac aatccaagag ttaagcaact gcttgcttat aaataaccaa    4440
gaggtgaact ttgaaaaaag tgattttgt tttatccatg tttctatgtt ctcaggttta    4500
cgggcaatca tggcatacga acgtagaggc tggttcaata aataaaacag agtcgatagg    4560
ccccatagac cgaagtgctg ctgcatcgta tcctgctcat tatatatttc atgaacatgt    4620
tgctggttac aataaagatc actctctttt tgacaggatg acgttttat gtatgtcatc    4680 aacagatgca tctaaaggtg catgtccgac aggagaaaac tccaaatcct ctcaaggga    4740 gactaatatt aagctaatat ttactgaaaa gaaaagtctg gccagaaaaa cattaaactt    4800
aaaaggatat aagagatttt tatatgaatc agatagatgc attcattatg tcgataaaat    4860
gaatctcaat tctcatactg ttaaatgtgt aggttcattc acaagaggag tagatttcac    4920
tttatatatc ccacaaggtg aaattgatgg gcttctaact ggaggtatat gggaggcaac    4980
actagagtta cgagtcaaaa ggcattacga ctataatcat ggtacttaca aagttaatat    5040
cacagttgat ttgacagaca aaggaaatat tcaggtctgg acaccaaagt ttcatagcga    5100
tcctagaatt gatctgaatt tacgtcctga aggtaatggt aaatattctg gtagtaacgt    5160
gcttgagatg tgtctctatg atggctatag tacacatagt caaagtatag aaatgaggtt    5220
tcaggatgac tcacaaacag gaaataatga atataatctt ataaaaactg gagagccatt    5280
aaaaaaattg ccatataaac tttctcttct tttaggagga cgagagtttt atccaaataa    5340
tggagaggct tttactatta atgatacttc gtcattgttt ataaactgga atcgtattaa    5400
gtctgtatcc ttaccacaga ttagtattcc agtactatgc tggccagcaa acttgacatt    5460
tatgtcagag ctaaataatc cagaagcggg tgagtattca ggaatactta acgtaacatt    5520
tactcctagt agttcaagtc tgtaaaaata gtatctttat aaattatgct atttgcggga    5580
gactttatca gctgggaatt agagtcgcaa tgatgtttat cggtaaacca gcaccatact    5640
tcggaaaatg ctggcaagct tacgccaatc ttttagatt gagttgttgg tattagatat    5700
catagtaaat ggttagcttg taaagttagc gctatcatga aatatttgat ttttataata    5760
ttaaaagagt ccctctgaag gtggactgca ccccaaaa                           5798
```

<210> SEQ ID NO 6
<211> LENGTH: 1187
<212> TYPE: DNA
<213> ORGANISM: Escherichia coli
<220> FEATURE:
<221> NAME/KEY: gene
<222> LOCATION: (245)..(1042)
<223> OTHER INFORMATION: rns

<400> SEQUENCE: 6

```
gcgcggcttt ttttgataaa acataaaaat gctcttttac tttcattgaa agattgcctc      60
tgataaaata tcagaggcat acaattgtac atcatagcga tggcatcaag gagataagat     120
aataacaaaa acaccagaag ctgaaaagct gaaaaacata tctttctttt agggggggatt    180 aagccaacct tgcaaaaagt gattgtacaa gcaactcaaa cctcttgtct tttgtaggta     240
```

```
taagatggac tttaaataca ctgaagaaaa agaaacaata aaaattaata atattatgat    300
tcataaatac actgtattat atacatcaaa ttgtattatg gatatatatt cggaagaaga    360
gaaaattaca tgttttagta acagacttgt atttcttgaa agagggtaa atatatctgt    420 aagaatgcag aagcaaattt tatcagaaaa gccgtatgtt gcattcagat tgaacggaga    480
tatgctaagg catttaaagg atgcattgat gataatatat ggcatgtcaa aaatagatac    540
caatgcttgt agaagcatgt caagaaaaat aatgacaaca gaggtgaata aaaccttgtt    600
ggatgaatta aaaaatataa acagccatga taactcagct tttatatcta gcttgatata    660
tttgatttca aaacttgaga ataatgaaaa aataatagaa tcaatttata tatcatctgt    720
gagttttttt tctgacaagg tcagaaatct tatcgaaaaa gatctatcca gaaaatggac    780
gctgggtatt attgcagatg cgtttaatgc atcagaaata accatcagaa aaagactaga    840
atctgagaat actaatttta atcagatatt aatgcaattg agaatgagta aggctgcgtt    900
attactactt gaaaattcat accagatatc tcagatatca aatatgattg gaatttccag    960
tgcatcttat tttattagga tttttaataa acattatggt gttacaccaa agcaattttt    1020
cacttatttt aaaggtggat aaaaacacct tattttgaat gcgttgcata atactatgct    1080
gtataaaaat gtatctagta gagatttatt gcgatgcgaa ctgaattgaa ataaaaattt    1140
ttgttaacac acagattaat cctttacaat attcggcaca atagcgc    1187

<210> SEQ ID NO 7
<211> LENGTH: 4746
<212> TYPE: DNA
<213> ORGANISM: Escherichia coli
<220> FEATURE:
<221> NAME/KEY: gene
<222> LOCATION: (378)..(1103)
<223> OTHER INFORMATION: cstA
<220> FEATURE:
<221> NAME/KEY: gene
<222> LOCATION: (1858)..(3579)
<223> OTHER INFORMATION: cstB
<220> FEATURE:
<221> NAME/KEY: gene
<222> LOCATION: (2266)..(3579)
<223> OTHER INFORMATION: cstC
<220> FEATURE:
<221> NAME/KEY: gene
<222> LOCATION: (2668)..(3579)
<223> OTHER INFORMATION: cstD
<220> FEATURE:
<221> NAME/KEY: gene
<222> LOCATION: (3031)..(3579)
<223> OTHER INFORMATION: cstE
<220> FEATURE:
<221> NAME/KEY: gene
<222> LOCATION: (3577)..(3579)
<223> OTHER INFORMATION: cstF
<220> FEATURE:
<221> NAME/KEY: gene
<222> LOCATION: (3580)..(4131)
<223> OTHER INFORMATION: cstG
<220> FEATURE:
<221> NAME/KEY: gene
<222> LOCATION: (4153)..(4659)
<223> OTHER INFORMATION: cstH

<400> SEQUENCE: 7
aagcttcacg acatagcggg gaggtttgct tctttgagag gcgggtttac gtttacgggg     60
tttagctgaa cgggccatat aaccacctga agacaatga catttcctgt ttttataacg    120
gtaattgcag accatgacaa gccacagccg tcaggctgtc tactcggcat tgttatctct    180
ttaaaacatt gaggtgaagc tatgctgaca caggaggtaa ttacccaatc tgaataagaa    240
```

```
ttattgggtg atctcctccc atgaaaatac gcacgcgaga agtgatatag atggaatgtt      300
gtgttttttt atcaaaatta tatttgttta tggagtatta taacaataag ttattgacgc      360
ttatgctagg agaaagaatg acacctatta agctaatttt tgcagctctg tctttatttc      420
catgcagtaa catttatgca aacaatataa ccactcagaa attcgaagct atattgggtg      480
caacaagagt aatttaccac ctagatggta atggtgaaag tctaagagtt aaaaatccgc      540
agattagtcc aattctaatt caatctaaag taatggacga gggtagtaaa gataatgcgg      600
attttattgt taccccccct cttttagac tagatgcaaa aagagaaact gacattcgta      660
tagttatggt gaatggctta tacccaaaag acagggaatc tctaaagacc ctctgtgtgc      720
gaggaattcc accaaaacaa ggagatttat gggctaacaa tgaaaagaa tttgttggaa      780 tgaaacttaa cgtttcaatt aacacatgta ttaaattaat attaagacca cataatcttc      840
ctaaacttga tattaattcc gaagggcaga tagaatgggg gataagggat ggtaatttag      900
tagcaaagaa taaaacacct tactatttta ctatagtaaa tgcatcgttt aatggaaagg      960
cactcaaaac accggggacg ctagggccgt atgagcaaaa actttacacg ctacctagta     1020
aaatttctgt atctggactg gtaaagtggg aaattattgg tgatctaggt gagagcagtg     1080
aaacaaagaa attcaatatt tgaagaatta aaagtgtact aaaaactgtc gagctaaact     1140
attcgtacta ttatttttat gtgattctgt taatgcagaa aaatatatat ttgagcgaga     1200
tttccttgct gattctgaaa aaattgattt aacattattg gagtcaagtg cctacccctc     1260
tggtcgttat tatgttagtt tgtatttgaa tggggaatac attacaaaag aatgatgatg     1320
tactttgacg ctggagaaag tgaggatttt tgtattcagt actctgtact acaggatata     1380
ggtgtaactg tgagtgggaa tcaggatgaa tgtgcaaatc ttgatgatga attaaactta     1440
agaaccaggt ttgatttta ctcgaaaaga atggatattt ttgtatcacc aaagtttgtt     1500
ccacgaaaaa aaacggtct tgcgccaatt aaactttggg atgagggtga aaatgcgcta     1560
ttcacaagtt acaactttag tgaggattat taccatttta aaggtgacgc aagagatagt     1620
tattcacaat acgctaacat tcaaccacgc ttaaatatag gaccatggag aataagaact     1680
caagccatat ggaataaaaa taataacaca aaaggggagt ggagtaataa ttacctgtat     1740
gccgaaagag gctaggaaa tataaagagt agactataca ttggggatgg atattttcca     1800
ttaaaaaact ttaattcgtt caaatttaaa ggaggggtgc taaaaactga tgagaatatg     1860
tatccctatt cagaaaaaac ttattcacca atagttaaag gctcggcaaa aactcaagca     1920
aaagttgaat tttttcagga tggtgtaaaa atttatagct caatcgtccc tccagggat     1980 ttttctatct cagattatat tttatcaggc tcaaatagtg atctttatgt caaagttata     2040
gaggaaaatg gctcaattca ggaatttatc gttccattta cctatcctgc agttgcggtc     2100
cgggaaggat ttacctatta tgaaatcgct atgggagaga ctcagcagtc gaatgattat     2160
tttacacagt tatcatttac tcgtgggctt ccatatgact ttaccgtact tacatcttta     2220
gaatattctg gcttctacag atctcttgaa attgggttag gaaaatgct tgggaatttg     2280 ggcgcattat cgttaatcta tggacagtca aactttagta aaagtgataa tagtaaaaat     2340 aaaaatggg atatcagata taataaaaat attccggacc taaatacata tttgagtttt     2400
tctgctgtta gccaaactag agggggtat tcttcactca gggatgcttt ggactatgag     2460
atcggagaat atacttttaa ctcaaaaaac tcctatacag cctcaataaa ccactcatta     2520
ggagagcttg gtagtttaaa ctttagtgga acatggcgaa actactggga gaataagaac     2580
caaaccagat cttacaattt atcatattct acacaaatct ttaatggaaa ggcctacttg     2640
```

-continued

```
tcaggaagtt tgattagaag tgaacttatg aattttaata ataagataag tgatactatt    2700
ttaaatatcg gtgttaatat tcccttggc ctttctcgtg gcattcaatc tgtaagttat     2760
aacaccagtt cagtgaaagg ggggaggagt actcatcagt tagggataag tggttctgaa    2820
tttgacaata aattgtactg gcatgtaaat cagggttact cagataatta cagtaatacc    2880
tctatgtatg gttattataa agctaagtat gctcaggtta atgccggata ctcagtttct    2940
gagagataca atcatgctta tggaggtata gagggaggaa ttctggtata tgacggtgga    3000
attattttag gtcgcaatct tggtgataca atgtcaatta ttgaagctcc aggtgcggaa    3060
aatacaaaga ttagaggatg gggatcgatt gaaactgatt ggaggggag ggcttttatt     3120 ggttatcttt caccttacca aaataatgat atatcccttg acccatcatc attaccatta    3180
gactcctctt tagatatcac aacaaattcg gttattccaa caactggtgc aattgttaaa    3240
acgacatata atgttaaaaa aggaaaaaaa gtaatgctta ctttaaaaaa gtcaaatggt    3300
gatgcagttc catttggagc aattgtgaca gttatggatg gcgatcaaaa tacaagcatt    3360
gtgggcgata atgggcaatt gtatttaggt tcctcaatgg atacaggaag gctaaaagtt    3420
atatggggaa atggcgaaga taaaaaatgt gttgttgact acatagtagg tgacaataaa    3480
aatatagcgg gtatttatat aggcagtgcc gaacatgtat ttagctcaat gctcctttat    3540
ggcaaaaaaa tatcttttt atccgcttct gtttggtagg ttataggtgt tgttaaagcg     3600
tttctgacaa ctctgcaatc caataacgaa tggagaacac acagtgaaaa aaatgatttt    3660
agcattgact ttgatgtcgg tgtggggagg tcgtttgccg cagtgggccc aacgaaagat    3720
atgagtttag gtgcaaattt aacttcagag cctacattag ctattgattt tacgcctatt    3780
gaaaatattt atgtaggtgc caattatggt aaagatattg gaaccttgt tttcacaaca    3840 aatgatttaa cagatattac attgatgtca tctcgcagcg ttgttgatgg tcgccagact    3900 ggtttttta ccttcatgga ctcatcagcc acttacaaaa ttagtacaaa actgggatca    3960
tcgaatgatg taaacattca agaaattact caaggagcta aaattactcc tgttagtgga    4020
gagaaaactt tgcctaaaaa attcactctt aagctacatg cacacaggag tagcagtaca    4080
gttccagata cgtatactgt tggtcttaac gtaaccagta atgttattta aagtgaatgt    4140
atgagggatt cgatgttaaa aataaaatac ttattaatag gtctttcact gtcagctatg    4200
agttcatact cactagctgc agcggggccc actctaacca aagaactggc attaaatgtg    4260
ctttctcctg cagctctgga tgcaacttgg gctcctcagg ataattaac attatccaat    4320 actggcgttt ctaatacttt ggtgggtgtt ttgactcttt caaataccag tattgataca    4380
gttagcattg cgagtacaaa tgtttctgat acatctaaga atggtacagt aacttttgca    4440
catgagacaa ataactctgc tagctttgcc accaccattt caacagataa tgccaacatt    4500
acgttggata aaaatgctgg aaatacgatt gttaaaacta caaatgggag tcagttgcca    4560
actaatttac cacttaagtt tattaccact gaaggtaacg aacatttagt ttcaggtaat    4620
taccgtgcaa atataacaat tacttcgaca attaaataat tatataatag acgtagcctt    4680
cgaaataaag gctacgttgc tatctttatg tttgtgattt ataggcatca ttaaatagtc    4740
aagctt                                                              4746
```

<210> SEQ ID NO 8
<211> LENGTH: 7239
<212> TYPE: DNA
<213> ORGANISM: Escherichia coli
<220> FEATURE:
<221> NAME/KEY: gene
<222> LOCATION: (283)..(999)
<223> OTHER INFORMATION: csaA
<220> FEATURE:
<221> NAME/KEY: gene
<222> LOCATION: (1028)..(1531)
<223> OTHER INFORMATION: csaB
<220> FEATURE:
<221> NAME/KEY: gene
<222> LOCATION: (1589)..(4192)
<223> OTHER INFORMATION: csaC
<220> FEATURE:
<221> NAME/KEY: gene
<222> LOCATION: (4196)..(5281)
<223> OTHER INFORMATION: csaE
<220> FEATURE:
<221> NAME/KEY: gene
<222> LOCATION: (6346)..(6849)
<223> OTHER INFORMATION: IS1 sequence

<400> SEQUENCE: 8

```
atatatctta ttgaggaata tcggtgtcat tgagtaccgt taacttaaga taaagaatct    60
gtctggaaat cgcaggacca agaactctca gtacatctgt ggcgataata ttatcgcttc   120
ttatacattc caatatgcag ttcttgtggg tatttgtttg gacatcgcag cattaaatat   180
aaaaatagca caggaggcat aattatttgt ttttactgtc ttattttttt atcccatttt   240
tttttgtttt gatttatctt tgatgaaagc tcaggaggga atatgcataa attattttgt   300
ttactaagtt tactcataac tccatttgtt gcaaatgcaa actttatgat atatccaata   360
tcaaaagatt taagaatgg aaatagcgag ttaattcgtg tttattcaaa atcaaaagag   420
atacaatata taaaaatata tacaaaaaag attattaatc ccggcacaac tgaagaacat   480
gaagttgata tgcccaattg ggatggtggg tttgtagtta ctcctcaaaa agttattctt   540
cctgcaggag ggagtaaatc aatacgttta actcaattta gaataccaaa aaagaggaa   600
atttatagag tatattttga ggcggtaaaa ccagatagca agaaaatgt aattgataat   660
aaaaaactaa caacagagct atctgttaat ataatttatg cggctctaat cagatcttta   720
ccaagtgaac aaaacatatc actaaacatt tctagaaatg caagaaaaaa tataattatt   780
tataataatg ggaatgttag agcaggtgtt aaagatattt attttttgtaa gtcatctaat   840
atcgatgata gctgtgtaaa aaaaacgcat aacaagaata tatatccaga aaagtcattt   900
gatacgctgg ttaataacaa ttttttcttat gttttcatta aattaaacca tgaagacata   960
gaaaaagagc aaggactaat acaattaaaa gttccttgat tactcatcta tatactaagg  1020
agttctaatg aaattaaaaa aaactattgg tgcaatggca ctgaccacaa tgtttgtagc  1080
tatgagtgct tctgcagtag agaaaaatat cactgtaaca gctagtgttg atcctacaat  1140
tgatattttg caagctgatg gtagtagttt acctactgct gtagaattaa cctattcacc  1200
tgcggcaagt cgttttgaaa attataaaat cgcaactaaa gttcatacaa atgttataaa  1260
taaaaatgta ctagttaagc ttgtaaatga tccaaaactt acaaatgttt tggattctac  1320
aaaacaactc cccattactg tatcatatgg aggaaagact ctatcaaccg cagatgtgac  1380
ttttgaacct gcagaattaa attttggaac gtcaggtgta actggtgtat cttcttccca  1440
agatttagtg attggtgcga ctacagcaca agcaccaacg gcgggaaatt atagtggggt  1500
cgtttctatc ttaatgacct tagcatcata atatttaa tatataaagg agcaggcaca  1560
ctgctcctta ttatatggca ataataaat gacaaaaaaa aatacattat atataacgat  1620
catcgcaatg ctaactccat attcagtttt ttccggagat atacccaact ctttccgtga  1680
tttatgggga gaacaagatg aattttatga agtaaaacta tatggacaaa ctctaggaat  1740
acatcgaatt aaaacaaccc caacacatat taagttttat tcacccgaaa gcattttaga  1800
```

```
taaaataaat gtaaaaaaag aaaaggaaaa gaaattgagt gttttgttca ctaattcttt    1860
ttcaagaaat ggcaatatga gttgtcaggg gaatgctact atacagtata actgcaatta    1920
cattaaaaca aaatcagtag atgtcatcgt tgatgatgtt gataatgttg ttaaccttt     1980 tataggtaat gaatttctgg attctgaagc acacaatgat gaatatcatc aattatcacg    2040
aaatgtaaaa aaagctttta tacaaagcca gacaattaat gtctcagatt ctgggaagta    2100
taaaagtttg tctgtttcag ggaatagcgc gctgggtatt acagatacaa gttatgctgt    2160
cttaaattgg tggatgaatt acaataaatt taatggttac agcaacaacg aaagaacaat    2220
caatagtttg tactttagac atgatttaga taagagatat tattatcaat ttggacgaat    2280
ggatcgtaca gatttgtcac aaagtattag cgggaacttt aattttaact tacttccttt    2340
acccgatatt gatggtataa ggacaggaac cacacaatct tatatcaaaa atacagataa    2400
gtttatcgca tcccctgtaa ctgttatgtt aactaattt tccagagtgg aagcttttcg     2460
caataatcaa ttattgggcg tatggtattt agattctgga gtaaatgaat tagatacagc    2520
tcgtttacct tatggtagtt acgatcttaa attaaaaatt tttgaaaata ctcagttagt    2580
tcgtgaagaa ataattcctt ttaataaagg gagaagttct attggtgata tgcaatggga    2640
cgttttcatt cagggaggga atattattaa tgacaaggat cgttacatag aaaaacaaaa    2700
taatcataag tcatcagtta atgctgggct acgtttacca attacgaaaa atatctctgt    2760
tcaacaagga gcatctgtta tagataataa aaattattat gaagggagtc tcaaatggaa    2820
ttccggcatt ctgtctggct cactaaatag tgagttcagt tttctttggg gagataatgc    2880
aaaaggtaat tatcaaagta tctcgtatac cgatggattt agtttatcat tttatcataa    2940
tgataagcgg gtcgataatt gtggaagaaa ttacaatgct ggttggagtg gatgctacga    3000
atcatattcg gcatctttaa gtattccttt attgggatgg acaagtactc tgggatatag    3060
tgacacttat agtgaatcag tttataaaaa ccatattctt tctgaatatg gtttttataa    3120
tcaaaacata tataagggaa gaacccaaag atggcaactg acttcgtcca cctctttaaa    3180
atggatggat tataatttta tgccagcaat tggaatatat aacagtgagc aaagacaact    3240
gactgataaa ggcggatata tatctgtaac tctcacccga gccagcagag aaaattcatt    3300
aaacgcaggg tattcttaca actattccag aggaaagtat tcttctaacg aattatttgt    3360
tgatggatat atgacatcaa caaataatgg tgactatcat gaggtaagaa tgcgttttaa    3420
taaaaataga cataatgcag aaggtagact ttcaggtcgt ataaacaatc gatttggaga    3480
tttaaatggt tcattcagca tgaataaaaa cagaaacacc aacagtagca atcattctct    3540
cactggtggt tataattcct catttgctct tacaagtgat ggattttact ggggaggaag    3600
tgcatctggt ttgacaaaac tagctggcgg tattatcaag gttaaatcaa acgatactaa    3660
aaaaaatctg gtaaagtga ctggggcatt gtacggtgat tattcgctag ggagcaacga    3720
taatgctttt attcctgtac cagcattaac tccagccagt ttaattattg aagataataa    3780
ttatggtgac aagaatattt ctgtacttgc accaacgaac aacgatatgt ttatattgcc    3840
gggtaatgtt tatcctgttg aaattgaaac caaagtaagt gtttcttata ttggtagagg    3900
ttttgacaaa aacggcacgc cactttctgg cgcacatgtt ttgaatgaac cacatgttat    3960
cctggatgag gacggtggat tttcgtttga atatacaggt aatgagaaaa cacttttttt    4020
attaaagggc agaactattt atacatgtca actggggaaa aataaagttc acaaaggcat    4080
tgttttcgtc ggagatgtta tatgtgatgt taatagcaca agttccttac cagatgaatt    4140
tgtaaagaac ccacgtgtgc aggatttgct ggcaaagaat gataaaggat aaacgatgaa    4200
```

```
taagatttta tttattttta cattgttttt ctcttcagta cttttacat ttgctgtatc   4260 ggcagataaa attcccggag atgaaagcat aactaatatt tttggcccgc gtgacaggaa   4320
cgaatcttcc cccaaacata atatattaaa taaccatatt acagcataca gtgaaagtca   4380
tactctgtat gataggatga ctttttttatg tttgtcttct cacaatacac ttaatggagc   4440
atgtccaacc agtgagaatc ctagcagttc atcggtcagc ggtgaaacaa atataacatt   4500
acaatttacg gaaaaaagaa gtttaataaa aagagagcta caaattaaag gctataaaca   4560
attattgttc aaaagtgtta actgcccatc cggcctaaca cttaactcag ctcattttaa   4620
ctgtaataaa aacgcggctt caggtgcaag tttatattta tatattcctg ctggcgaact   4680
aaaaaatttg cctttggtg gtatctggga tgctactctg aagttaagag taaaagacg    4740 atatagtgag acctatggaa cttacactat aaatatcact attaaattaa ctgataaggg   4800
aaatattcag atatggttac ctcagttcaa aagtgacgct cgcgtcgatc ttaacttgcg   4860
tccaactggt gggggcacat atattggaag aaattctgtt gatatgtgct tttatgatgg   4920
atatagtact aacagcagct ctttggagat aagatttcag gataacaatc ctaaatctga   4980
tgggaaattt tatctaagga aaataaatga tgacaccaaa gaaattgcat atactttgtc   5040
acttctcttg gcgggtaaaa gtttaactcc aacaaatgga acgtcattaa atattgctga   5100
cgcagcttct ctgaaaacaa actggaatag aattacagct gtcaccatgc cagaaatcag   5160
tgttccggtg ttgtgttggc ctggacgttt gcaattggat gcaaaagtgg aaaatcccga   5220
ggctggacaa tatatgggta atattaatgt tactttcaca ccaagtagtc aaacactcta   5280
gataacaaca atattggcgc tattgcgcgc caatattgta aagggtaat ctgtttgtta    5340 acaaacatt ttgtttcaat tcagtttgca tcgcaataaa tctctactag agacatttt     5400 atacagcata gtattataca acacattcaa aataaggata ttttatcca ccttaaaat    5460 aagtaaaaaa ctgctttggt ataacaccat aatgtttatt aaaaacccta ataaataag    5520 atgtactgga aattccaatc atatttgata tctgagatat ctggtatgaa ttttcaagta   5580
gtaataacgc tgccttgctc attctcaatt gcattaagaa ctggttaaaa ttagtattct   5640
cagattctag tcttttctg atggttattt ctgattcatt aaacatatct gcaatgatag    5700
ccagtgtcca ttttctggat agatcttttt cgataatatt tctgaccttg tcagaaaaaa   5760
attcacagat gatatataaa ttgattctat tatttttat tattctcgat ctttgaaatt    5820
aaatatatca aattagatat aaaagctgag tcatcatagc tattatt ttttaataca      5880 tccagtaagg ttttatccac ttctgtttc attattttcc ttgacatatt tctacaatca    5940
ttggtatcta tttttgacat accatatatt atcatcaatg catcctttaa atgtcttagt   6000
atgtctccgt tcaatctgaa tgcaacatat ggttttctg ataaaatttg cttctgtatt    6060
cttacagata tattcacccc tctttcaaga aatacaggtg atgctgccaa cttactgatt   6120
tagtgtatga tggtgttttt gaggtgctcc agtggcttct gtttctatca gctgtccctc   6180
ctgttcagct actgacgggg tggtgcgtaa cggcaaaagc actgccggac atcagcgcta   6240
tctctgctct cactgccgta aaacatggca actgcagttc acttacactg cttctcaacc   6300
cggtacgcac cagaaaatca ttgatatggc catgaatggc gttggatgcc gggcaacagc   6360
ccgcattatg ggcgttggcc tcaacacgat tttacgtcac ttaaaaaact caggccgcag   6420
tcggtaacct cgcgcataca gccgggcagt gacgtcatcg tctgcgcgga aatggacgaa   6480
cagtggggct atgtcgggc taatcgcgc cagcgctgg tgttttacgc gtatgacagg     6540
ctccggaaga cggttgttgc gcacgtattc ggtgaacgca ctatggcgac gctggggcgt   6600
```

-continued

| | |
|---|---|
| cttatgagcc tgctgtcacc ctttgacgtg gtgatatgga tgacggatgg ctggccgctg | 6660 |
| tatgaatccc gcctgaaggg aaagctgcac gtaatcagca agcgatatac gcagcgaatt | 6720 |
| gagcggcata acctgaatct gaggcagcac ctggcacggc tggacggaa gtcgctgtcg | 6780 |
| ttctcaaaat cggtggagct gcatgacaaa gtcatcgggc attatctgaa cataaaacac | 6840 |
| tatcaataag ttagagtcat tacctggttc acgtattatt atccgtgact ctttcctggt | 6900 |
| aactcccgca taataacctc acttttccag tattccagaa gatgatgttt tttcctcgat | 6960 |
| aataaaaatg tgccaatatg gaaataagaa atcggatttt ttatcagcat acgcaaattt | 7020 |
| tcagataaca atgaatacag atgtattta tatacacaga taaaaccgcg caacagacat | 7080 |
| aaatatgaca gtagcatgaa aaagcagaga gagacagggt gatacagaaa agtaactatt | 7140 |
| tttttagcta tagtattatt ggtttacct attttcgtga ttgtgtttct gtatatttga | 7200 |
| caatgagtct ctcagaatcg gtttctcgaa gtgacgagc | 7239 |

<210> SEQ ID NO 9
<211> LENGTH: 9935
<212> TYPE: DNA
<213> ORGANISM: Escherichia coli
<220> FEATURE:
<221> NAME/KEY: gene
<222> LOCATION: (1427)..(2038)
<223> OTHER INFORMATION: csfA
<220> FEATURE:
<221> NAME/KEY: gene
<222> LOCATION: (2096)..(2770)
<223> OTHER INFORMATION: csfB
<220> FEATURE:
<221> NAME/KEY: gene
<222> LOCATION: (2767)..(5211)
<223> OTHER INFORMATION: csfC
<220> FEATURE:
<221> NAME/KEY: gene
<222> LOCATION: (5227)..(5838)
<223> OTHER INFORMATION: csfE
<220> FEATURE:
<221> NAME/KEY: gene
<222> LOCATION: (5852)..(6526)
<223> OTHER INFORMATION: csfF
<220> FEATURE:
<221> NAME/KEY: gene
<222> LOCATION: (6523)..(7644)
<223> OTHER INFORMATION: csfD

<400> SEQUENCE: 9

| | |
|---|---|
| ggtgatgctg ccaacttact gatttagtgt atgatggtgt ttttgaggtg ctccagtggc | 60 |
| ttctgtttct atcagctgtc cctcctgttc agctactgac ggggtggtgc gtaacggcaa | 120 |
| aagccccgcc ggacatcagc gctatctctg ctctcactgc cgtaaaacat ggcaactgca | 180 |
| gttcacttac accgcttctc aacccggtac gcaccagaaa atcattgata tggccatgaa | 240 |
| tggcgttgga tgccgggcaa ctgcccgcat tatgggcgtt ggcctcaaca cgattttacg | 300 |
| tcacttaaaa aactcaggcc gcagtcggta acctcgcgca tacagccggg cagtgacgtc | 360 |
| atcgtctgcg cggaaatgga cgaacagtgg ggctatgtcg gggctaaatc gcgccagcgc | 420 |
| tggctgtttt acgcgtatga cagtctccgg aagacggttg ttgcgcaagt attcggtgaa | 480 |
| cgcactatgg cgacgctggg gcgtcttatg agcctgctgt cacccttga cgtggtgata | 540 |
| tggatgacgg atggctggcc gctgtatgaa tcccgcctga agggaaagct gcacgtaatc | 600 |
| agcaagcgat atacgcagcg aattgagcgg cataacctga atctgaggca gcacctggca | 660 |
| cggctgggac ggaagtcgct gtcgttctca aaatcggtg agctgcatga caaagtcatc | 720 |
| gggcattatc tgaacataaa acactatcaa taagttggag tcattaccaa cggtttcagc | 780 |

```
ttaaccattt tgtggcgggt ctttctggct ggcggttcag ggtatttaag gtagcgtctg    840
accgtccagc tctcagtaca cgtcccgacg ctgaactggt caatacaatg ctggataatg    900
ctgtcgaaac gttaaattct ggagaacgac cggtgataca cagtgacaga tgtaggcatt    960
atcgctggcc aggctggctg aaagagtgaa tgcagcaggt cttattcgct caatgtcccg   1020
taaaggatgt tcacctgata atgccgcatg cgaaggcttt ttcggcggat tgaagactga   1080
aatgtattat gggcgtaaat ggtcgggtat catgccagaa aagttcatgc agcaagtaga   1140
tgcctacatc agatggtata acgatcggcg tataaaatta tcgctgggta catttcatgg   1200
ctgtacagca tcttattaaa caatcattat actatattga cagcatgcaa tatctacatg   1260
tttgacgtta ttttactttt cttgttattg tattatcgta ttgtgtatct gtattttgt    1320 agtatatgaa aaacactat agcaaaacaa gcttacttga aaaagttata agtgttttca    1380
caaataaatt cgtgtttatt gtaagacaaa gaaggatgag aataaaatga agaaaaattt    1440
actgataact tcagtgttgg caatggcaac cgtatcaggt tctgttttgg ctgctgttac    1500
aaatggccaa ctcacattta attggcaggg agtggttcct tccgctcccg ttactcagag    1560
cagctgggct tttgtgaacg gattggatat accgtttact cctggtactg aacagttgaa    1620
tatcacccct gattcaaata aagatatcac ggcccgttcg gttaagcctt atgattttt     1680 cattgttcca gttctggaa acgtaactcc tggagcgccg gttacgcgtg acacgtcagc     1740
taatataaac agtgtgaacg cttttctatc aagtgtaccc gtttctaatg gttttgttgg    1800
caacaagcag ttaaccctga gtaccgcagt agaagcagct aagggggaag tcgcaatcac    1860
tttaaatggt caagcgctta aagtggggag cgctagtcca acagttgtta ctgtggctag    1920
taataaaaaa gagtctcata tttctattga tatgaatgcc aaggcagctg ctgcggatgt    1980
ggcagagggg gcagctatta actttgtagc tccggtaaca tttgctgttg atatttaatc    2040
tgcattattt ttataccaaa ggaggggggg gccctccttt gccggaatag tttttatgaa    2100
gattctgtat tcttttttgt tgttaccttt tttttcttgc gccttcagtg ttgattcaat    2160
gataaagttt tcaggcgaag atgacttttt tcttgtaaat ggaaatagca aggaaagaga    2220
gtatatctat gtaacgcttt ctgaactaat tagcgagaaa acaataggc gcgatgaaat     2280 attttacaac gcagacaatg tgcctctatg gcctatatct gcagaacctg cagatattat    2340
tatttcatct ggcgaacaag tcaaaataaa aatcaacaaa aattatactc ctgtcggcgg    2400
agatcgaatt tttggtatta atttcagccc agatacactg aatgataatg atagaaatca    2460
gtataacata ccgtttggtt ataaagcatg gctgattgtt cccggaacag aatctgaatc    2520
tggtacagta gatgttagca aagtttcgga aaaaacaaa tatatcatta aaaacaacac     2580
aaataaagta atggatgttt gggcagatta ttgtggaagt tataataata ataaatgcag    2640 agtcagctt attactcgac cgtattcaga aaaaagata gagatagata gtaacaataa      2700
tccaattgaa tttacttttt ctatttatat cggacgcgaa cgaaaactga taaaaagaaa    2760
gattttatga ctctaaaaga caccttattt tttttatcta tcagtattta ttgcagtcaa    2820
tctctagctg ataaaagtga gctggctata ctcagtccta ataaatcaac cacgatttg     2880 gttctggcag gaggaattaa cctgaacgtt tcccgttatg caggaataat tacgcctgaa    2940
tctggtacag tcaaggtgct ttttgatgga gtaactgaga gcactctgaa tgccaaaata    3000
tccttggata cagtgcagtt tcaagacaat gtacagtttg aatcatttct gaaaaatgtc    3060
ggtattcgtg agaaatatat tgaaaaaatc ttgaaccaga atacccgagt cggtttcgtc    3120
cattcccaag ggtgtcaggg acctcgaagt gaatgtattg tagttagtaa aggaattgac    3180
```

```
tttgtcgtgg attactataa ccaaacaatt cgactgtttg ttgcgccaga attgttaggg    3240
aagagcgttg gagagaattc atatctcacg cttaatggcg aacttgggat tattaataac    3300
ctatcaggtt actattacga aacttttggt cgctatgacc cgacatacta tattcgtgat    3360
caaggggtgg ttggggcagg tgcgggattt attcgctata atatttaccg ttcagattat    3420
cagaataatg tggatgaact ctattacagc cgtgccttga tagccgataa taaaatactg    3480
gttggcagga cgcaaagtaa cggtaacttt aatccatcca gcgctcagtc tatttttttct   3540 gatatttcag tcactgggat acgatttgga acagccgagg agttggttga tcgcagttat    3600
ggaaagaaaa catttagtta ttacagcccg tcaactggaa tagtggaagt aagtaaagat    3660
aatattctgg tgtacgctat tgctacgcag gcaggatatg gcgaaatcaa tttagcaaat    3720
ttgccttatg ggcagtataa tgctttggtt caggtaaaat cgtcttccgg aatagttgtc    3780
tcatcgcaga atgtgctgat taacaataca ggttcattca acagtgactt ctcttggcat    3840
ctctttgtag ggaatagtgg ttcttctgac aatgaatttg tcagaaaaaa taccgaagtt    3900
attgagagcg gtgttcaact tcctgtaaat acacttactg ctctttacgt aggaggtgct    3960
aaggttgata aaaatacgat ttacagtact ggtttaatgt tccagaaaga accgatttct    4020
gtttcactaa aaatgggggg ggggcaggga tttagacatt acgaaatgaa aagttatctt    4080
gaaagactgt cactctcatg gaaaaagaca gtacaggta aaaactggaa tggcctaaaa     4140
tccagcacag ataatactac actatcagcc ggctataact tcaatgtgat gtcgaatgtg    4200
tctgctaatg ttgatatat atattcctcg agcatgaggc cagattactt ttacgctaat     4260
actgaccatt tgggtatgga gtcagagttc agatataaaa aaaacaacta ttcaaacaag    4320
aatctttatg ccaatatgta ttacaatttt cctggaggca atagtttata tctaaacacc    4380
tacaaggaat taagaggaaa tgattacagc gtttctttgg ggatgaatat atctttgggt    4440
aaaaactcac gttttaacag ctcattctat aaaaacggag cagatataac aaatagtagc    4500
actgtggatt atgcaaaaag gctttctgat aactggtcac actcagtatc agtaggaaga    4560 tattttttcta atgatagtta taattctgcc acatacagtc tctcccataa tagcaatgaa    4620 gtgaggggg caggttatta ctatgctact gataatggac agagtcaact tacgttgaca    4680
gcagatagca ctcagattat taacagtaat gggatatatt ttacttcgtc ttcatggaag    4740
gataatgctt ttattattcg aggaaaggac gccaaatatg atatttccgt caggaatatg    4800
actgataata ccacgcgtta ttttgattcc gacacaaata ttatcagtgt gcctgtatat    4860
aataaagtaa tggtgaacag tgacacatct gggtcaaact tgattttttga aaattatcag    4920 accaagaaaa gtcgtagttt tgcgcttgta ccagggtcaa cggtaatggt ttcagacaaa    4980
actatcagcg cgaactccgt cattgtcaca ctgaaaaaaca gtaataatca gtatgcccga    5040
acggcatttt gcaacggaga cagttgtata gcagtttctc gcctgaatca gggagtattt    5100
cgagtgaaat atacgggga ttcactcacg ctgcgttcgg aggggagca gtgttcgaca     5160 tctgaaatta ataaaaggaa atatgtaagc attacctgtc aaaaaatata agagaagagt    5220
atctggatga aaataaaaaa attcaaactt gtcttctata tggtaatttt ttatgtaatc    5280
agtctgcaag aagtgctatc agccagcacg tctgtgatta ctaataacgg acaaacgata    5340
actcttacgc ttcctgtgag ggcaaccatt acagcagata gtattctacg tgacactata    5400
ttggttaagc ccttgtcatc cctttatgat gttgttacat gggattcgga gaataacaga    5460
tttaaaaatc atgaattcct tgttagggtg attaaagaaa cagctgtacc tatttcattt    5520
gaggttatta atgatcaata tacctgtagt tataataacc ctgacaggat gtctcccctg    5580
```

```
ccgacagata ttgccatcgc gaactctgat tataaataca gtgtttcatg gtcaggtgga    5640
tatgttgata tgggaaaggg acgcgcagct actgtaaatg acagtcactc gtggctatct    5700
tctgtcaatg gtgttgacag atatttagac ttaacgctaa atataaactt tcctgatatg    5760
actccatata ctcagttgct aaatcgtgga ggactatgta gggggagtat aactatgctg    5820
ctaagtaata aattataaag agatgaacct aatgttttt tttagagcga ttttaatcgt     5880 ttttttatc ggatcagatg ttcaagcttt tcagatagat acgttaacca aggtgataga    5940
taaagacacc caatacattg aaataacggg ggaatacgaa cgggaatata tttatacaca    6000
attaacacaa cttcttactg ataaaaaaca tggactccgt gagattcctt ttaatccgga    6060
ggatatatct tcatggccta ttattgtaga acctggagaa attgtgcttg ataaggcgga    6120
taaaatcaga gttaaaatca tccgaaacgg tccgcaacag gatgaggatc gcgtgtcagg    6180
tctagcattt atacccgaaa aggtgcgcag gaagaaaatc caagattcag gccttcaaat    6240
atcggtagga tataaggtat ggctgtttat acccggcaaa tctcctttaa agggacagat    6300
aaaagcctcc aaaaaagtg gaaatataac aattgaaaat atgaccaata aaatattaag    6360
aattgttcct gatgattgtt caggaaaaaa taaatctgaa tgtgccggag cggtaattct    6420
attaccatat actagtaagc agattgatga ctcagagcat gtacagacgc ttagtattta    6480
tctaattaat gatttacata aaaaaataaa ggtaatcaca ttatgaaaaa caacctatt    6540 gtattaactc taggctttt ttcctttatg gttcaggctg ctacaacagt tacttcagaa     6600
tttgaaatta ctaataaaac tatcgaaaaa tatacaatat caagtacaga tagtactatg    6660
acatatactg atgtatcagg gagtggttta tataaaatat cagaccagta ttcagatgcc    6720
aatgtcaata ttagaaatta cggcaatcat cagtttggat tgctcagaaa taacagcact    6780
gttaatatta tcatgaaggg cgtaaactta ggccacactt ttactgtaca aggaaaatat    6840
gccaattcag ccgtgtcagt tcccaatcct caaaaatatt ttaccgttag aagtaataat    6900
ggatgctcaa gtgtatcttc tgcatatcta ggtaatgcga gttatacgct atacgaaata    6960
agatctagta atgatgttac acggaactgt tccggacaaa cggatcagta cactcatatg    7020
ccaaataata gtggtcaggt aaatgttaca ggaatttaca gagatttcta cttggatatt    7080
ggtcgactgc aatcagacgc tgagtatagg aaagcacctc ctgataccta tataggaaca    7140
gggacattcg ctggagaggt tttaaagaat cgagtaggtt ctggttatac tccgacttat    7200
acaaacaaaa taacaattac aaaaaaacca tattttgaaa gtgtgacatt gcccacggta    7260
gataatatct tcgatactcg tactatcggc agacagattc aggggaatct tgtaattcca    7320
tttgtgatta atgggcattt cacaccatac aatactattt cgttgcaggt catttcacta    7380
aatgggttta agttacaaag tgagaatgtt ggttcctcag caaccattcc ttattcgcta    7440
aatatgacga taggtagtga acgacgttat tccttggcca caaatgggaa tggtttggga    7500
aatgttacaa taaataacct cgaatctgat ggctattcca ttcaaggacg cttcaatgca    7560 gatttttga tcgataaaaa tacagctgtg acaggagatt atgccgatac attgacagca    7620
atatttcaga tttcgctact ataaattata gtacgaacaa ttacctcctg tagtggtcag    7680
tagcatattg tcttgcattg aggcggttaa ttaacgttac tattttcgtg gattaatttt    7740
tgagtgagaa gatgatcagg ccaaatgtag tggaaatat cattgcccgc caacttgaag    7800
cttcaggtct ctggcgcagg gcatctgcgt gttggctggt tgttatgggg tattccagat    7860
atacagatga agatcgggag tagttattgc agcatcgaga atattgcttg gcgcagatat    7920
cgccttcgtc actaccggaa agactggata ttagtgaggt ggcaagggcg aatgatgcaa    7980
```

```
caccgaaacg tatgggggt ggcaatgcag agagtgaact gtccgataaa acgcggtatc    8040
gcgggacccc gggggcttc ctgcatgtta acgggaaaat actgcgaata tccgccgctg    8100
taccgtcaga gtgaaatctt tgtccgtcag ggtgtcgaac tgagctaggt attactctcc    8160
aactggattg atgcgtgctg ccagttgatg gttccgccaa atgatgccct atacaactat    8220
gtgatgaaca cccgcaatgt tcacactggc gacacaccag taaaagtgct gacaccgggc    8280 agaaaaagc aaaacaggc cgcatctgga cgtatgtccg ggatacacgt tcagcgcatt    8340
ccactgtttc agcaggtata cgaacgctga agtggctgaa gtggcacact gaatttggcc    8400
acctgaacag aggtgatatg ctcacctcag aacaacacag gtgctccaat gaaaaaaga    8460 aattttagcg cagagtttaa acgcgaatcc gctcaactgg ttgttgacct gaaatacacg    8520
gtggcagatg ccgccaaagc tatggatgtt ggccttttcca caatgatcaa gatgggtcaa    8580
acaactacgt gatgagcgtc agggcaaaac acctaaagcc tctccgataa caccagaaca    8640
aatcgaaata cgtaagctga ggaaaaagct acaacgcatt gaaatggaga atgaaatatt    8700 aaaaaggct gttgtagatt caattggtca acgcaacagt tatgtgaaaa catggggttg    8760
cggaggtttt ttgaatgaga cgaacattta cagcagagga aaaagcctct gttttttgaac    8820 tatggaagaa cggaacaggc ttcagtgaaa tagcgaatat cctgggttca aaacccggaa    8880
cgatcttcac tatgttaagg gatactggcg gcataaaacc ccatgagcgt aagcgggctg    8940
tagctcagct cacctgacac tgtctgagcg cgaggagata cgagctggtt tgtcagccaa    9000
aatgagcatt cgtgcgatag ctactgcgct gaatcgcagt ccttcgacga tctcacgtga    9060
agttcagcgt aatcggggca gacgctatta caaagctgtt gatgctaata accgagccaa    9120
cagaatggcg aaaaggccaa aaccgtgctt actggatcaa aatttaccat tgcgaaagct    9180
tgttctggaa aagctggaga tgaaatggtc tccagagcaa atatcaggat ggttaaggcg    9240
aacaaaacca cgtcaaaaaa cgctgcgaat atcacctgag acaatttata aaacgctgta    9300
ctttcgtagc cgtgaagcgc tacaccacct gaatatacag catctgcggc ggtcgcatag    9360
ccttcgccat ggcaggcgtc ataccccgcaa aggcgaaaga ggcacgatta acatatgaac    9420
ggaacaccaa ttcacgaagt tcccgaaata tcgataacag acgctctcta gggcattggg    9480
agggcgattt agtctcaggt acaaaaaact ctcatatagc cacacttgta gaccgaaaat    9540
cacgttatac gatcatcctt agactcaggg gcaaagattc tgtctcagta aatcaggctc    9600
ttaccgacaa attcctgagt ttaccgtcag aactcagaaa atcactgaca tgggacagag    9660
gaatggaact ggccagacat ctagaattta ctgtcagcac cggcgttaaa gtttacttct    9720
gcgatcctca gagtccttgg cagcggggaa caaatgagaa cacaaatggg ctaattcggc    9780
agtactttcc taaaaagaca tgtcttgccc aatatactca acatgaacta gatctggttg    9840
ctgctcagct aaacaacaga ccgagaaaga cactgaagtt caaaacaccg aaagagataa    9900
ttgaaagggg tgttgcattg acagattgaa tctac                              9935
```

<210> SEQ ID NO 10
<211> LENGTH: 4689
<212> TYPE: DNA
<213> ORGANISM: Escherichia coli
<220> FEATURE:
<221> NAME/KEY: gene
<222> LOCATION: (1742)..(2647)
<223> OTHER INFORMATION: csvR

<400> SEQUENCE: 10

```
aagcttcttt cattcgctga aagtggaatg tatccatgga gaacacttta tcagctggga      60
```

```
aataatgcgg gcaacggtat ttaattatat cgaatgtgat tacaatcggt ggcggcggca    120
cagttggtgt ggcggcctca gtccggaaca atttgaaaac cagaacctcg cttaggcctg    180
tgtccatatt acgtgggtag gatcatatcg cctacattga cacgttttaaa aggagaaacg    240 taacgagttt caccttctc ggatatgact tcaaagtgcg tacgctgaag aatttcaaag     300
gcgaactgta ccgaaagtgc atgccgggtg cgtcaaatgc agcaatgcgc aaaataacag    360
aaacaatcaa gaagtggcgt atacatcgct caacaggtga gagtttgctg gattttgcga    420
gtcgctacaa tgcgatagtg agaggctgga gcgggtacta cggaaagttc tggtccagaa    480
atttcaacta tcgactgtgg agtgcaatgc agtcacgtct gctcaagtgg atgcagtcta    540
aatacagact ttcgaaccgg aaggctcagt gaaagctgac gctggtaagg aaggagtatc    600
cgaagctatt tgtcctctgg tatttcctgc gtgcatcgaa tgagtggtca agagccgtat    660
gacgcgagag tgtcacgtac gattccgtga gcagccgggg agtgaaattc tctccggctg    720
actcgactcg cgggttccga cagcggtggc gaacatgcgg cggtgttgta ctcgctgatc    780
ggcacatgcc gtctgaacaa tgtggagcca gaaaaatggc tgcgttacgt cattgagcat    840
atccaggact ggccggcaaa ccgggacgtg atctgttgcc ttggaaagtg atctgagctc    900
tcagtaaata tcaattcggt tctgacgagc cgcttacgca acagctgaaa aaggttcatt    960 atttatgga aaccgtgagc ccattccccg gtgataaaca tgggctggta aaagagtagc    1020
ggtattagat gtagctatct aagaaaatat cataaatatg tcttaattta ggcatatgtg    1080
aaacctcaaa agtgcacatt tagctaacac ttgtcatttt ttttctttaa aatatcactt    1140
tcccttacat ctgagtgatt tattaacttg ccaattggat gattttttgag ttgtgttttt    1200 atttcaatct actgtttata gagaaatatac ccttagaata aaggataatt ttttgtaaa    1260 ctcacaaaaa caatataagt ataaaatata ccgatgagtg actgttttgc attcaataaa    1320
acatataact atatattttg atttttttctt tttgagtttc gattaatgaa cgcttcacaa    1380
aacattgctc tatctatgca ccactttata ttatcaggca ctttacacaa aagtgatgct    1440
tgcttccata gttcaaaggc cgaaaccata tctgtttttc tttctgctaa agcagcttct    1500
tgagataaag agtgaaaaga atcttttgcc ataaaagtac attacttaag caggtatatt    1560
ggattttgtc agtatacaat acgaatattc cgtcaagatg ataaaaaaat gtagggctaa    1620
gaaaatctgg gtgcggaaga gagggttaaa aaaatatcgc tttgtttgca ggtggagagg    1680
caagattaca aaggcagatt aagcaagaaa atcaagccac ctaattttta tggatagcga    1740
gatggacttt aaatatacag aagaaaaaga gttaataaaa ataaataatg taatgattca    1800
taagtatact atattatata catcgaattg tattttggat atatcttttg gtgaagataa    1860
gattacatgt ttcaataata ggcttgtgtt tcttgagaga ggggtaaata tctctgtgag    1920
aatccaaaaa caaaaattaa cagaaaaacc atatgtcgca ttcagattga atgaaaatgt    1980
gcttagacat ttaaaaaaca cgttaatgat aatatatgga atgtcaaaaa tagactcctg    2040
tgagtgtagg ggagtatcga gaaaaataat gacaactgaa gtagataaaa tgttattgaa    2100
tgtgttaaga gagatgatgg ggcatcataa tgatgattca tcttttatat ctgcactaat    2160
atatctaatt tcgaaaatca aatgcaatga taaaataata gaatcgcttt acatgtcttc    2220
tataaccttt tttactgaca aagtcagagg tgttatcgaa aaagacctat caagaaaatg    2280
gactttggct ataattgcag atgtatttaa tgtatcagaa ataactatca gaaaaagatt    2340
agaatctgaa gacactaatt tcaaccagat cttaatgcaa tcaagaatga gcaaagcggc    2400
attgttattg cttgaaaaatt catatcagat atctcagata tctaatatga ttgggatttc    2460
```

```
tagcgcatct tattttatta ggattttcaa taaacatttt ggcgttacgc gaagcagttt    2520
tttaattatt ttaaaggagg atgaaaatgt ttttgctacg cgccaaggca atagttctct    2580
gacccagttg acttgcgagt tcaaacacat aagtggaggt aaccgtctaa atcgctgcac    2640
ggaataagtt ctccacggct ttgttgaata aatcgaattg ttgctgagtt gaaggatcag    2700
acacacatcc cctgacaaca caggcattcc tgtggcaaag cagcagttca gaatcaccaa    2760
ttggcacagg gcaggtatga gtcagcaacc ccttcatcac gggaacctca gcgctattct    2820
gacctcgcta tcaccactgt tctggtgatt gattacatcg gctgaaagt tttcggtgac     2880
ggtgagtgga aagtcaaaaa acatggcaaa gaacggcgtc gtacttggcg gaacgtacga    2940
tggtcaggtt actgaggcac tggctatcgc gccctgaaca aaatgacgaa ggcgggtatg    3000
ccagaaagcg tgcaaacttc ctgaaaaccc aactggatac agagcgtctc acctgaaact    3060
gggtgatgcc tctaattggt tgaattgaag tataatgctc gcttttgagg ttttctcatg    3120
gccatcgtta ctgtccattg tccccgttgt cagtctgctc aggtttaccg ccatggtcag    3180
aaccctaaag gccgtgccgg tttcgctgcc gtgactgcca tcgtgtattt ctgctcacct    3240
acacctatga agcccgtaag cccggcgtca agagcaaat caccgaaatg gcgttcaacg     3300
gagcagggg ccgcgatacc gcaaggacac tcaaaattgg tataaatacc gtcatccgca     3360
cttaaaaaa ttcgcgccaa agagaataac gcccctccg gtcgctcatg cagatgtcgc      3420
gctcatctgc gagcccgatg aacagtggag ctttgtcggc agcaaggccc gacagcactg    3480
gctctggtat gcctgcaaca ccaaaacagg tggtgttctt gcttatacgt tcggtccacg    3540
aacggatgaa actgtcgtga gctgctggct ctgctcaccc cgtttaatat cggcatgata    3600
acgagcgacg actggggaag ttatgccaga gaagtcgcga aggaaaagca tctgaccggc    3660
aaactattca ctcagcgcat tgagcgtaac aatctgacgc tgagaacccg catcaagcgt    3720
ctggcccgca aaacaatctg cttttcacgc tcaattgagc tacatgaaaa ggttatcggg    3780
gccttaattg aaaaatacat gttctactaa ttggaagcat cacctggaaa ctgacttatc    3840
caacaaagca acttaatatt gtatatacaa aaccctctaa aaattagaat aattaaaact    3900
tctatcaaat tcaattctaa tgatgaatga aaatttttctt acgtttaatg gcattataca   3960
acataagaag gaagtcaata aaatatttcg ataaaaacat caaccatcac tccagttta    4020
tgtaagttat tatttttag ctccgagaga agtgcggatg ttttaaaatc agtgaggtag     4080
taatacatct gcaaatgtaa ggaaatacaa ataaaaagaa ttatactttc tctttctgta    4140
atttttgtt ctcattctgc tttagcaggc agcactgatt ggcagccatc agtagggcca     4200
ggacaatgta tagtatatgc agaaattggt gagacaggag ggtataaatg gaataatcag    4260
aatgaatgta acgaagttgt gcgcagagga tatgcaatag gagtaggtgt ctcgggtaaa    4320
gttatatatg aaggaaataa gccggggtat aatggggatt caattagcta ttcaggtatc    4380
gtcaccctg acagagatta taagcgacaa gcacctgccg tttataacgg aaagaaaaaa     4440
gtggctcatg gcgatagtta tacgtactgg gcaaatagt aatcagcaat aaaacctcac     4500
tatagttaag tatagcgcaa aagctaatgt tatgctacct tgtgatttca aggtagcata    4560
tttataaaaa taatttaaaa atattatccc gatgataaat agtggacacg tttaatgatt    4620
cttccctcgt aatatatgat gaccattttt gttattctcc acaacgagtt agttcttctt    4680
tttggatcc                                                            4689
```

<210> SEQ ID NO 11
<211> LENGTH: 5113

```
<212> TYPE: DNA
<213> ORGANISM: Escherichia coli
<220> FEATURE:
<221> NAME/KEY: gene
<222> LOCATION: (649)..(1113)
<223> OTHER INFORMATION: cssA
<220> FEATURE:
<221> NAME/KEY: gene
<222> LOCATION: (1131)..(1634)
<223> OTHER INFORMATION: cssB
<220> FEATURE:
<221> NAME/KEY: gene
<222> LOCATION: (1687)..(2385)
<223> OTHER INFORMATION: cssC
<220> FEATURE:
<221> NAME/KEY: gene
<222> LOCATION: (2342)..(4801)
<223> OTHER INFORMATION: cssD

<400> SEQUENCE: 11
aagcttcacg acatagcggg gaagtttgct tctttgaggg gcaggttttc gtttacgggg      60
tttagctgaa ctggtcatat aactaactga aaaacaatga tattatctgt ttttataacg     120
gtaatttcag gccatgacaa gccgcagccg ccacggtcta ctcgagtggc taatcagcga    180
atgaccggga gtaatgcgcg gtggaaatgg acaacagatt acaaccgtcg ctcgatagcg    240
gaaacggcga tgtaccgggt aaaacagctg ttcgggggggg gggcactgac gctgcgtgac   300
tacgatggtc aggttgcgga ggctatggcc ctggtacgag cgctgaacaa aatgacgaaa    360
gcaggtatgc ctgaaagcgt gcgtattgcc tgaaaacaca acccgctacg ggggagactt    420
acccgaaatc tgatttattc aacaaaccgt cacggctggg aatctctctc cggcagcctt    480
caggaagaaa ttccatcaag acggctgctt aaaaagaac aaatggtagt gtccgctatt     540
gccagtacac ctcactcacc aataaaagcg tcaatacggt gctccgtcga cacattacga    600
atgttatgta tacaataaaa atgattatag caatagtaat ggtgttatat gaagaaaaca    660
attggtttaa ttctaattct tgcttcattc ggcagccatg ccagaacaga aatagcgact    720
aaaaacttcc cagtatcaac gactattca aaaagttttt ttgcgcctga accacaaatc    780
cagccttctt ttggtaaaaa tgttggaaag gaaggaggtt tattatttag tgtgagctta    840
actgttcctg aaaatgtatc ccaggtaacg gtctaccctg tttatgatga agattatggg   900
ttaggacgac tcgtaaatac cgctgatgat tcccaatcaa taatctacca gattgttgat    960
gataaaggga gaaaaatgtt aaaagatcat ggtgcagagg ttacgcctaa tcaacaaata   1020
acttttagag cgctgaatta tactagcgga gataaagaaa tacctcctgg gatatataac   1080
gatcaggtta tggttggtta ctatgtaaac taaatactgg aagtatgatt atgttgaaaa   1140
aaattattcc ggctattgta ttaattgcag gaacttccgg agtggtaaat gcaggaaact   1200
ggcaatataa atctctggat gtaaatgtaa atattgagca aaatttatt ccagatattg    1260
attccgctgt tcgtataata cctgttaatt acgattcgga tccgaaactg aattcacagt   1320
tatatacggt tgagatgacg atccctgcag gtgtaagcgc agttaaaatc gtaccaacag   1380
atagtctgac atcttctgga cagcagatcg gaaagctggt taatgtaaac aatccagatc   1440
aaaatatgaa ttattatatc agaaaggatt ctggcgctgg taagtttatg gcagggcaaa   1500
aaggctcctt ttctgtcaaa gagaatacgt catacacatt ctcagcaatt tatactggtg   1560
gcgaatacc taatagcgga tattcgtctg gtacttatga aggacatttg actgtatcat    1620
tttacagcaa ttaaaaaag gccgcattat tgattgcggc cattgacgat actgccaggc   1680
aaaaatatga aatcaaagtt aattatatta ttgatgttag tgccattttc atctttttca   1740
acagaaaata attttgaaat aaataagaca cgagtaattt actctgacag cacaccatca   1800
```

```
gttcaaatat caaataataa agcatatcct ttaattgttc aaagcaatat atgggatgaa    1860
aacaataata aaaatcatga ctttatagca acaccaccga tttttaaaat ggaaagtgaa    1920
agcaggaaca taataaaaat aatcaaaaca aatattaaat tgccggactc tcaggaaagt    1980
atgagatggt tatgtattga atcaatgcca ccaacagaaa aaagtactaa aataaacaga    2040
aaagaaggaa ggacagacag tattaatatc agcattcggg gatgcattaa actgatatat    2100
cagcctgcca gtgttccgtc tcctgttttt aataatatag tggaaaaatt aaaatggcat    2160
aaaaatggaa agtatcttgt attaaaaaat aatcacccct attacattag cttttctgag    2220
gttttttttg attcagataa agtaaacaat gcaaagata ttttatatgt aaaaccatac     2280
tcagagaaga aaatagatat cagcaacaga ataataaaaa aaatcaaatg ggcaatgatt    2340
gatgatgctg gcgcaaaaac aaaactttat gaatcaattt tataaaaaat atcattatag    2400
tatacaaaaa tatcagatta cagacttgct tttttttcta tttctatatc cttttcaac    2460 ctcatatgga aatgaacaat ttagttttga ctcacgattc ctaccatcag gttataatta    2520 ctcttttaaat agtaacttac ctcctgaagg tgagtatctg gttgatattt atattaacaa   2580
aataaaaaag gagtccgcga ttattccttt ttatataaaa ggaaataaac ttgtaccatg    2640
tttatcaaaa gaaaaacttt catctttggg tatcaacatt aataataacg acaacgcaga    2700
gtgtgcagaa acaagtaagg caggtattag taatatcagc tttgagttta gctcccttcg    2760
tttgtttatt gctgtaccaa aaaatcttct gtctgagatt gataaaatat catcaaagga    2820
tatagataac gggatccatg ctttatttt taattatcaa gtaaatacaa ggctagctaa     2880
taataaaaat cgttatgatt acatttctgt ttcaccaaat ataaattatt tttcatggcg    2940
gttgcgtaat cgttttgaat ttaaccaaaa caacgataaa aaaacatggg aaagaaacta    3000
cacttatcta gaaaaaagtt tttatgataa aaagctaaac ttaatcgttg gtgaaagtta    3060
tacgagttca aatgtttata ataactactc ttttactggt atttcagttt ctacagatac    3120
agatatgtat acgccaagtg aaatcgatta tacaccagaa attcatggag tggctgattc    3180
agactctcag attattgtta ggcaaggcaa caccattatc attaatgaaa gtgttccagc    3240
cggaccgttc tcatttccaa taaccaatct catgtatact gggggcaac ttaatgtgga     3300 gataacagat atttatggaa ataaaaaaca atatactgtc agtaattcct ctcttcctgt    3360
tatgagaaaa gcgggactaa tggtatataa ttttatatct ggaaaattaa caaaaaaaaa    3420
tagtgaagat ggtgattttt ttgcccaagg tgatattaac tacggtactc actataacag    3480
cacactattc ggtgggtatc agtttagtaa aaattatttt aacttatcta ctggtatagg    3540
cactgatctg ggattttctg gagcatggct actaaacgtt agcagaagta attttaagga    3600
taaaaatgga tataatatta atctacaaca aaacactcag ttaagaccat tcaatgccgg    3660
ggttaatttc gattacatat acagaaaaaa agggtatgtg gaactttccg gcattggctg    3720
gcatggtaat ttatataatc aacttaaaaa tagtttttct ttatctttgt caaaatcatt    3780 ggataaaatac ggaaatttct cacttgatta taacaaaata aaatactggg ataatgcgta   3840
tgatagtaac tcaatgtcga ttcgttattt ttttaaattc atgcgagcaa tgattacaac    3900
aaattattct ttaaataaat atcaatctta tgaaaaaaaa gataaaagat ttagtattaa    3960
tatatcattg cctttaacca aagattacgg gcacatatct tcaaactatt cattttccaa    4020
tgcaaataca ggaacggcaa ccagttctgt aggtgtaaac ggtagttttt ttaatgacgc    4080
aagattaaac tggaacattc agcagaacag aacgacccgt aacaatggat atactgataa    4140
taccagttac atagcaacca gctatgcctc tccctatggc gttttactg gttcatattc      4200
```

```
aggatcgaac aagtattcaa gccagttcta ttccgcattg ggaggtattg ttttgcatag    4260
cgatggcgta gcttttactc aaaaagccgg agatacctct gctcttgtcc gtattgataa    4320
tatttctgat ataaaaattg gtaacactcc tggtgtttat actgggtata atggttttgc    4380
tttaattcct catcttcagc cgttcaaaaa aaacaccatt ttaattaatg ataaaggaat    4440
tccagacgat attgctcttg ctaatataaa aaaacaagtt atcccatcac gaggagctat    4500
tgttaaagta aaatttgatg ctaaaaaagg caataacatt ttgtttaagc ttacaactaa    4560
agatggaaaa acgcccccat taggagctat agcccatgaa aaaaatggaa aacagattaa    4620
tacgggtatc gttgacgatg atggcatgct ttatatgtct ggattatcag gggcagggat    4680
tattaatgta acatggaatg gaaaagtctg ttcatttcct ttttcagaaa aagatatatc    4740
tagcaaacaa ttatctgttg taaataaaca atgtaaccgc cccgaaaatt ctggagacta    4800
aacttcctga gaagaggta aacaggatga ctaaaaatac tcgttttttcc ccgaaatccg    4860 tcaacgggca gttcaaaagg attatctggc tgaagtggc aattacagta acgaccgctg    4920
ggaagcaccg caacgtgcct cacgcctagc tgctagcgta atgaggtagc ctgaatttaa    4980
cggacactcc ttcctgaaat agaatgacat cagaaggagt taatcatgac cagaaaacct    5040
caaagttact ctaaagaatt taaagccgaa gcggtcagaa ctgttcacgt ataggaaatg    5100
gctttgtgaa gtg                                                       5113

<210> SEQ ID NO 12
<211> LENGTH: 27
<212> TYPE: DNA
<213> ORGANISM: Artificial Sequence
<220> FEATURE:
<223> OTHER INFORMATION: synthetic primer 47151

<400> SEQUENCE: 12
ccggtcgacc ttattgagga atatcgg                                        27

<210> SEQ ID NO 13
<211> LENGTH: 24
<212> TYPE: DNA
<213> ORGANISM: Artificial Sequence
<220> FEATURE:
<223> OTHER INFORMATION: synthetic primer 47152

<400> SEQUENCE: 13
ggcgcatgca gatctgatta gagc                                           24

<210> SEQ ID NO 14
<211> LENGTH: 31
<212> TYPE: DNA
<213> ORGANISM: Artificial Sequence
<220> FEATURE:
<223> OTHER INFORMATION: synthetic primer 47150

<400> SEQUENCE: 14
ggcgcatgcc ggaattccat ttgagactcc c                                   31

<210> SEQ ID NO 15
<211> LENGTH: 21
<212> TYPE: DNA
<213> ORGANISM: Artificial Sequence
<220> FEATURE:
<223> OTHER INFORMATION: synthetic primer RNS-03

<400> SEQUENCE: 15
acatcatagc gatggcatca a                                              21
```

-continued

<210> SEQ ID NO 16
<211> LENGTH: 23
<212> TYPE: DNA
<213> ORGANISM: Artificial Sequence
<220> FEATURE:
<223> OTHER INFORMATION: synthetic primer RNS-04

<400> SEQUENCE: 16
tatttcaatt cagttcgcat cgc                                             23

<210> SEQ ID NO 17
<211> LENGTH: 29
<212> TYPE: DNA
<213> ORGANISM: Artificial Sequence
<220> FEATURE:
<223> OTHER INFORMATION: synthetic primer 47173

<400> SEQUENCE: 17
gacggatccg aatgcgaggc atccggttg                                       29

<210> SEQ ID NO 18
<211> LENGTH: 35
<212> TYPE: DNA
<213> ORGANISM: Artificial Sequence
<220> FEATURE:
<223> OTHER INFORMATION: synthetic primer 47174

<400> SEQUENCE: 18
ttcctcaata agctctgtta tatgccttta tttgc                                35

<210> SEQ ID NO 19
<211> LENGTH: 32
<212> TYPE: DNA
<213> ORGANISM: Artificial Sequence
<220> FEATURE:
<223> OTHER INFORMATION: synthetic primer 47175

<400> SEQUENCE: 19
tataacagag cttattgagg aatatcggtg tc                                   32

<210> SEQ ID NO 20
<211> LENGTH: 30
<212> TYPE: DNA
<213> ORGANISM: Artificial Sequence
<220> FEATURE:
<223> OTHER INFORMATION: synthetic primer 47176

<400> SEQUENCE: 20
tggttgtcga gatctgatta gagccgcata                                      30

<210> SEQ ID NO 21
<211> LENGTH: 33
<212> TYPE: DNA
<213> ORGANISM: Artificial Sequence
<220> FEATURE:
<223> OTHER INFORMATION: synthetic primer 47177

<400> SEQUENCE: 21
tctaatcaga tctcgacaac cagttcactc gtg                                  33

<210> SEQ ID NO 22
<211> LENGTH: 29
<212> TYPE: DNA
<213> ORGANISM: Artificial Sequence
<220> FEATURE:
<223> OTHER INFORMATION: synthetic primer 47178

```
<400> SEQUENCE: 22
ggtggatccg ttaaagcgca tcagcgcgg                                              29

<210> SEQ ID NO 23
<211> LENGTH: 25
<212> TYPE: DNA
<213> ORGANISM: Artificial Sequence
<220> FEATURE:
<223> OTHER INFORMATION: synthetic primer 47180

<400> SEQUENCE: 23
ccgtcctgtg gatcctctac gccgg                                                  25

<210> SEQ ID NO 24
<211> LENGTH: 23
<212> TYPE: DNA
<213> ORGANISM: Artificial Sequence
<220> FEATURE:
<223> OTHER INFORMATION: synthetic primer 47182

<400> SEQUENCE: 24
atcggtcgac gctctcccgg tcc                                                    23

<210> SEQ ID NO 25
<211> LENGTH: 24
<212> TYPE: DNA
<213> ORGANISM: Artificial Sequence
<220> FEATURE:
<223> OTHER INFORMATION: synthetic primer 4732

<400> SEQUENCE: 25
gtacaaataa cctacaaaaa gccc                                                   24

<210> SEQ ID NO 26
<211> LENGTH: 22
<212> TYPE: DNA
<213> ORGANISM: Artificial Sequence
<220> FEATURE:
<223> OTHER INFORMATION: synthetic primer 47105

<400> SEQUENCE: 26
taacgcctgc tctaacattc cc                                                     22

<210> SEQ ID NO 27
<211> LENGTH: 21
<212> TYPE: DNA
<213> ORGANISM: Artificial Sequence
<220> FEATURE:
<223> OTHER INFORMATION: synthetic primer 47168

<400> SEQUENCE: 27
cgttatgcag gaataattac g                                                      21

<210> SEQ ID NO 28
<211> LENGTH: 21
<212> TYPE: DNA
<213> ORGANISM: Artificial Sequence
<220> FEATURE:
<223> OTHER INFORMATION: synthetic primer 47167

<400> SEQUENCE: 28
cgtattttta tcaaccttag c                                                      21

<210> SEQ ID NO 29
<211> LENGTH: 26
```

<212> TYPE: DNA
<213> ORGANISM: Artificial Sequence
<220> FEATURE:
<223> OTHER INFORMATION: synthetic primer 4714

<400> SEQUENCE: 29
ttcaacctta aaagctttaa aagcct         26

<210> SEQ ID NO 30
<211> LENGTH: 32
<212> TYPE: DNA
<213> ORGANISM: Artificial Sequence
<220> FEATURE:
<223> OTHER INFORMATION: synthetic primer 4715

<400> SEQUENCE: 30
ctacacgaac tctgaagatc agcagttcaa cc         32

<210> SEQ ID NO 31
<211> LENGTH: 31
<212> TYPE: DNA
<213> ORGANISM: Artificial Sequence
<220> FEATURE:
<223> OTHER INFORMATION: synthetic primer 4716

<400> SEQUENCE: 31
gatcttcaga gttcgtgtag actttccttg g         31

<210> SEQ ID NO 32
<211> LENGTH: 28
<212> TYPE: DNA
<213> ORGANISM: Artificial Sequence
<220> FEATURE:
<223> OTHER INFORMATION: synthetic primer 4717

<400> SEQUENCE: 32
gccactgcag cctcgcagag caggattc         28

<210> SEQ ID NO 33
<211> LENGTH: 28
<212> TYPE: DNA
<213> ORGANISM: Artificial Sequence
<220> FEATURE:
<223> OTHER INFORMATION: synthetic primer 4718

<400> SEQUENCE: 33
ggcactgcag gcgtagcacc aggcgttt         28

<210> SEQ ID NO 34
<211> LENGTH: 24
<212> TYPE: DNA
<213> ORGANISM: Artificial Sequence
<220> FEATURE:
<223> OTHER INFORMATION: synthetic primer 4719

<400> SEQUENCE: 34
tcatccggag ttccgtatgg caat         24

<210> SEQ ID NO 35
<211> LENGTH: 23
<212> TYPE: DNA
<213> ORGANISM: Artificial Sequence
<220> FEATURE:
<223> OTHER INFORMATION: synthetic primer 4720

<400> SEQUENCE: 35
tgccatacgg aactccggat gag         23

```
<210> SEQ ID NO 36
<211> LENGTH: 47
<212> TYPE: DNA
<213> ORGANISM: Artificial Sequence
<220> FEATURE:
<223> OTHER INFORMATION: synthetic primer 4721

<400> SEQUENCE: 36
gcttttaaag cttttaaggt tgaattcgat cggcacgtaa gaggttc                47

<210> SEQ ID NO 37
<211> LENGTH: 26
<212> TYPE: DNA
<213> ORGANISM: Artificial Sequence
<220> FEATURE:
<223> OTHER INFORMATION: synthetic primer 4722

<400> SEQUENCE: 37
ggcctgcagg caagacctaa aatgtg                                        26

<210> SEQ ID NO 38
<211> LENGTH: 27
<212> TYPE: DNA
<213> ORGANISM: Artificial Sequence
<220> FEATURE:
<223> OTHER INFORMATION: synthetic primer 4723

<400> SEQUENCE: 38
gcgctgcagc tttatgttga taagaaa                                       27

<210> SEQ ID NO 39
<211> LENGTH: 21
<212> TYPE: DNA
<213> ORGANISM: Artificial Sequence
<220> FEATURE:
<223> OTHER INFORMATION: synthetic primer 4766

<400> SEQUENCE: 39
caacagtact gcgatgagtg g                                             21

<210> SEQ ID NO 40
<211> LENGTH: 21
<212> TYPE: DNA
<213> ORGANISM: Artificial Sequence
<220> FEATURE:
<223> OTHER INFORMATION: synthetic primer 4917

<400> SEQUENCE: 40
atcaacggtg gtatatccag t                                             21

<210> SEQ ID NO 41
<211> LENGTH: 23
<212> TYPE: DNA
<213> ORGANISM: Artificial Sequence
<220> FEATURE:
<223> OTHER INFORMATION: synthetic primer R6K-01

<400> SEQUENCE: 41
gtgacacagg aacacttaac ggc                                           23
```